United States Patent
Courtney et al.

(10) Patent No.: US 8,592,430 B2
(45) Date of Patent: Nov. 26, 2013

(54) QUINAZOLIN-OXIME DERIVATIVES AS HSP90 INHIBITORS

(75) Inventors: Stephen Martin Courtney, Oxfordshire (GB); Mark Whittaker, Oxfordshire (GB); Owen Clifford Mather, Oxfordshire (GB); Christopher John Yarnold, Oxfordshire (GB); Oliver Robin Barker, Oxfordshire (GB); Christian Aldo Georges Napoleon Montalbetti, Oxfordshire (GB); Thomas Hesterkamp, Hamburg (DE); Mihaly Daniel Gardiner, Oxfordshire (GB)

(73) Assignee: DAC SLR, Milan (IT)

( * ) Notice: Subject to any disclaimer, the term of this patent is extended or adjusted under 35 U.S.C. 154(b) by 436 days.

(21) Appl. No.: 12/599,116

(22) PCT Filed: May 15, 2008

(86) PCT No.: PCT/IT2008/000326
§ 371 (c)(1),
(2), (4) Date: Dec. 15, 2010

(87) PCT Pub. No.: WO2008/142720
PCT Pub. Date: Nov. 27, 2008

(65) Prior Publication Data
US 2011/0118258 A1    May 19, 2011

(30) Foreign Application Priority Data
May 17, 2007  (GB) .................................. 0709534.2

(51) Int. Cl.
*A61K 31/517* (2006.01)
*A61K 31/519* (2006.01)
*C07D 239/84* (2006.01)

(52) U.S. Cl.
USPC ........................................ 514/258.1; 544/242

(58) Field of Classification Search
USPC ........................................ 544/242; 514/258.1
See application file for complete search history.

(56) References Cited

U.S. PATENT DOCUMENTS 5,536,725 A  *  7/1996  Cullen et al. ............. 514/266.22

FOREIGN PATENT DOCUMENTS

WO    WO 2009/097578    *  8/2009

OTHER PUBLICATIONS

STN database, File CAPLUS, Accession No. 1990:216843, Strakov et al. Latvijas PSR Zinatnu Akademijas Vestis, Kimijas Serija (1989), (5), 579-83 (abstract only).*
International Search Report issued by the International Searching Authority (ISA/EP) on Nov. 18, 2008 in connection with International Application No. PCT/IT2008/000326.
WO 2006/113498 A1 (Chiron Corporation) Oct. 26, 2006.
WO 2007/041362 A (Novartis AG) Apr. 12, 2007.
WO 2008/045529 A (Serenex Inc.) Apr. 17, 2008.
Strakov, A. et al., "2-Amino-5-oxo-5,6,7, 8-tetrahydroquinazolines", Latvijas Psr Zinatnu Akademijas Vestit, Kimijas Serija, No. 5, 1989, pp. 579-583.

* cited by examiner

*Primary Examiner* — Rebecca Anderson
(74) *Attorney, Agent, or Firm* — Gary J. Gershik; Cooper & Dunham LLP

(57) ABSTRACT

Compounds of general formula (I); or a stereoisomers, tautomers, pharmaceutically acceptable salts, or prodrugs thereof, wherein R1, R2, R3, R4, R5, R6, R8 and R9 are as defined herein, are useful for the treatment of diseases and conditions which are mediated by excessive or inappropriate Hsp90 activity such as cancers, viral infection and inflammatory diseases or conditions.

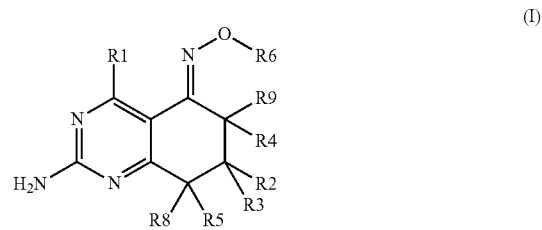

(I)

21 Claims, No Drawings

QUINAZOLIN-OXIME DERIVATIVES AS HSP90 INHIBITORS

This application is a §371 national stage of PCT International Application No. PCT/IT2008/000326, filed May 15, 2008, and claims priority of Great Britain Patent Application No. GB 070 9534.2, filed May 17, 2007, the contents of all of which are hereby incorporated by reference into this application.

FIELD OF THE INVENTION

The present invention relates to new compounds having Hsp90 inhibitory activity and to the use of these compounds in medicine, in particular for the treatment of diseases and conditions which are mediated by excessive or inappropriate Hsp90 activity such as cancers, viral infection and inflammatory diseases or conditions. The invention also relates to pharmaceutical compositions containing the compounds. In particular, the invention relates to 2-amino-7,8-dihydro-6H-quinazolin-5-one oximes and stereoisomers, tautomers, pharmaceutically acceptable salts or prodrugs thereof.

BACKGROUND OF THE INVENTION

The chaperone heat shock protein 90 (Hsp90) is an emerging target in cancer treatment due to its important roles in regulating key proteins in cell growth, survival, and differentiation pathways. Hsp90 inhibitors may have further medical use in the treatment of viral infections and inflammatory conditions. Hsp90 assists the folding, maturation, stability, and trafficking of a specific group of proteins called client proteins.

Hsp90 function is regulated by a pocket in the N-terminal region of the protein that binds and hydrolyzes ATP. Occupancy of this pocket by high affinity ligands prevents the Hsp90 client proteins from achieving their mature functional conformation. Protein clients of Hsp90 are mostly kinases, steroid receptors, and transcriptional factors involved in driving multistep malignancy and, in addition, mutated oncogenic proteins required for the transformed phenotype. Examples include Her2, Raf-1, Akt, Cdk4, cMet, mutant p53, ER, AR, mutant BRaf, Bcr-Abl, Flt-3, Polo-1 kinase, HIF-1 alpha, and hTERT (see Therapeutic and diagnostic implications of Hsp90 activation. *Trends Mol. Med.* 2004, 10, 283-290; Hsp90 inhibitors as novel cancer chemotherapeutic agents. *Trends Mol. Med.* 2002, 8, S55-S61; and Hsp90 as a new therapeutic target for cancer therapy: the story unfolds. *Expert Opin. Biol. Ther.* 2002, 2, 3-24).

The past few years have witnessed a tremendous growth in the discovery of Hsp90-specific inhibitors belonging to several distinct chemical classes, which include benzoquinone ansamycins (e.g. geldanamycin derivatives), radicicol derivatives, purine-scaffold-based inhibitors, dihydroxyphenylpyrazoles, and small peptides. Among them, 17-AAG and 17-dimethylaminoethylamino-17-demethoxygeldanamycin (17-DMAG), derivatives of the natural product geldanamycin, are currently under evaluation in multiple clinical trials. 17-AAG inhibits Hsp90 by binding competitively to its N-terminal ATP binding site. This site is highly conserved among Hsp90 family proteins, whose human members include cytoplasmic Hsp90α and Hsp90β, ER-resident Grp94, and mitochondrial tumour necrosis factor receptor-associated protein 1 (Trap1). The Hsp90 chaperone complex facilitates the folding of client proteins through coupled cycles of ATP hydrolysis. Thus, inhibition of the ATPase activity results in misfolding and degradation of client proteins via the ubiquitin-proteasome pathway and in turn leads to growth arrest or apoptosis in cancer cells (see *J. Med. Chem.* 2006, 49, 4606-4615).

Hsp90 is over expressed (about 2-20 fold) in multiple tumour types as a result of oncogenic transformation (e.g. accumulation of mutated proteins) and cellular stress (e.g. low pH and lack of nutrients). Cancer cells are very adaptive to hostile microenvironments and are capable of acquiring drug resistance, in part due to their inherent genetic instability and plasticity. Hence, a need exists for inhibitors of Hsp90 to combat a variety of hard-to-treat tumours by disrupting concurrently a wide range of oncogenic pathways.

More recently it became apparent that Hsp90 function is also required to sustain viral infections caused for instance by vesicular stomatitis virus, paramyxovirus SV5, HPIV-2, HPIV-3, SV41 and LaCrosse bunyavirus (Antiviral activity and RNA polymerase degradation following Hsp90 inhibition in a range of negative strand viruses. *Virology* 2007, Epub ahead of print). The Hsp90 inhibitors geldanamycin and radicicol were previously shown to block the replication of human cytomegalovirus (HCMV) and herpes simplex virus type 1 in relevant cell culture systems (Geldanamycin, a potent and specific inhibitor of Hsp90, inhibits gene expression and replication of human cytomegalovirus. *Antivir. Chem. Chemother.* 2005, 16, 135-146; Geldanamycin, a ligand of heat shock protein 90, inhibits the replication of herpes simplex virus type 1 in vitro. *Antimicrob. Agents Chemother.* 2004, 48, 867-872). Geldanamycin and radicicol treated cells fail to mount a NFkappaB-dependent anti-viral response and Hsp90 function has been shown to be required for proper NFkappaB signalling (Requirement of Hsp90 activity for IkappaB kinase (IKK) biosynthesis and for constitutive and inducible IKK and NFkappaB activation. *Oncogene* 2004, 23, 5378-5386). The NFkappaB signalling pathway is likewise operative in inflammatory conditions and the reported anti-inflammatory activity of geldanamycin is potentially explained by the failure of function as a transcription factor of NFkappaB in absence of Hsp90 chaperone function (Disruption of Hsp90 function results in degradation of the death domain kinase, receptor-interacting protein (RIP), and blockage of tumor-necrosis factor induced nuclear factor-κB activation. *J. Biol. Chem.* 2000, 275, 10519-10526; Geldanamycin inhibits NFkappaB activation and interleukin-8 gene expression in cultured human respiratory epithelium. *Am. J. Respir. Cell Mol. Biol.* 2001, 25, 92-97). Alternatively the anti-inflammatory function of the Hsp90 inhibitor may be related to the fact that the glucocorticoid receptor is a client protein for Hsp90 that does not function properly as a transcriptional regulator of pro- and anti-inflammatory genes in absence of Hsp90 function (Isolation of Hsp90 mutants by screening for decreased steroid receptor function. *Proc. Natl. Acad. Sci. U.S.A.* 1993, 90, 11424-11428; Geldanamycin, an inhibitor of heat shock protein 90 (Hsp90) mediated signal transduction has anti-inflammatory effects and interacts with glucocorticoid receptor in vivo. *Br. J. Pharmacol.* 2000, 131, 13-16).

In summary, due to its pleiotropic effect on central regulatory molecules like kinases, transcription factors and hormone receptors, novel Hsp90 inhibitors may have medical utility not only in cancer but also for the treatment of viral infections and inflammatory disease states like rheumatoid arthritis, Crohn's disease, etc.

WO 2006/113498 and WO 2007/041362 relate respectively to 2-aminoquinazolin-5-one and 2-amino-7,8-dihydro-6H-pyrido[4,3-d]pyrimidin-5-one compounds which are Hsp90 inhibitors. The present inventors have devised alternative Hsp90 inhibitors and have, surprisingly, found that the ketone group in these prior art compounds can be replaced by a group with increased bulk and functionality without loss of activity and, in some cases, with increased activity.

Therefore, in a first aspect of the present invention, there is provided a compound of general formula (I):

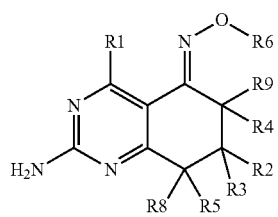

(I)

or a stereoisomer, tautomer, pharmaceutically acceptable salt, or prodrug thereof, wherein:

R1 is selected from hydrogen, halogen, hydroxyl, amino, thiol, $C_1$-$C_6$ alkoxy, $C_1$-$C_6$ alkylthiol, $C_1$-$C_{10}$ alkyl, $C_1$-$C_6$ alkylamino, arylamino, aryl($C_{1-6}$ alkyl)amino, aryl, heteroaryl, $C_3$-$C_7$ cycloalkyl, or $C_3$-$C_7$ heterocyclyl, any of which may optionally be substituted;

R2 and R3 are each independently hydrogen, halogen, $C_1$-$C_{10}$ alkyl, $C_2$-$C_{10}$ alkenyl, $C_2$-$C_{10}$ alkynyl, $C_3$-$C_7$ cycloalkyl, $C_5$-$C_7$ cycloalkenyl, aryl, heteroaryl, or $C_3$-$C_7$ heterocyclyl, any of which may optionally be substituted; R2 and R3 may also form a 3 to 6 membered Spiro ring system, optionally fused with an aryl or heteroaryl ring;

R4, R5, R8 and R9 are each independently selected from hydrogen, halogen, $C_1$-$C_6$ alkyl, —OR7, —SR7, —NR7R7', —OC(O)R7', —N(R7)C(O)R7', or —N(R7)SO$_2$R7'; R4 and R9 and/or R5 and R8 may also form a 3 to 6 membered Spiro ring system, optionally fused with an aryl or heteroaryl ring;

R7 and R7' are each independently hydrogen, $C_1$-$C_6$ alkyl, $C_2$-$C_5$ alkenyl, $C_2$-$C_5$ alkynyl, $C_3$-$C_7$ cycloalkyl, $C_5$-$C_7$ cycloalkenyl, aryl, heteroaryl, or $C_3$-$C_7$ heterocyclyl, any of which may optionally be substituted; or, when R4, R5, R8 or R9 is —OC(O)R7', —N(R7)C(O)R7', or —N(R7)SO$_2$R7', R7' may additionally be NR10R11, where R10 and R11 are each independently hydrogen or $C_1$-$C_6$ alkyl;

and

R6 is hydrogen, halogen, $C_1$-$C_6$ alkyl, $C_2$-$C_6$ alkenyl, $C_2$-$C_6$ alkynyl, (CH$_2$)$_n$C(O)R12, C1-C6 alkylN(R14)$_2$, $C_3$-$C_7$ cycloalkyl, $C_5$-$C_7$ cycloalkenyl, aryl, heteroaryl, or $C_3$-$C_7$ heterocyclyl, any of which may optionally be substituted;

n is 0 to 4;

R12 is $C_1$-$C_6$ alkyl, OH, O($C_1$-$C_6$ alkyl) or N(R13)$_2$;

where:

each R13 is independently hydrogen, methyl or ethyl, or the two R13 groups together with the nitrogen atom to which they are attached form a 5 to 7 membered heterocyclic ring optionally substituted and optionally containing a further hetero atom, selected from N optionally substituted, O or S;

each R14 is independently hydrogen, C1-C6 alkyl, or the two R14 groups together with the nitrogen atom to which they are attached form a 5 to 7 membered heterocyclic ring optionally substituted and optionally containing a further hetero atom, selected from N optionally substituted, O or S.

The compounds of the invention have Hsp90 inhibitory activity and are therefore useful for the treatment of diseases and conditions which are mediated by excessive or inappropriate Hsp90 activity such as cancers, viral infection and inflammatory diseases or conditions.

In the context of the present specification, the term "$C_1$-$C_6$ alkyl" refers to a fully saturated straight or branched saturated hydrocarbon chain having one to six carbon atoms. Examples include methyl, ethyl, n-propyl, isopropyl, t-butyl, n-hexyl, methylenecyclopropyl, methylenecyclobutyl and methylenecyclopentyl. "$C_1$-$C_3$ alkyl" and "$C_1$-$C_{10}$ alkyl" have similar meanings except that they contain from one to three and from one to ten carbon atoms respectively.

The term "$C_2$-$C_{10}$ alkenyl" refers to a straight or branched hydrocarbon chain having from two to ten carbon atoms and at least one carbon-carbon double bond. Examples include ethenyl, 2-propenyl and isobutenyl. "$C_2$-$C_5$ alkenyl" and "$C_2$-$C_6$ alkenyl" have similar meanings except that they contain from two to five and from two to six carbon atoms respectively.

The term "$C_2$-$C_{10}$ alkynyl" refers to a straight or branched hydrocarbon chain having from two to ten carbon atoms and at least one carbon-carbon triple bond. Examples include ethynyl, 2-propynyl and isobutynyl. "$C_2$-$C_5$ alkynyl" and "$C_2$-$C_6$ alkynyl" have similar meanings except that they contain from two to five and from two to six carbon atoms respectively.

When alkyl, alkenyl and alkynyl groups are substituted, suitable substituents include one or more halo, OH, SH, O($C_1$-$C_6$ alkyl), S($C_1$-$C_6$ alkyl), nitro, NH$_2$, NH($C_1$-$C_6$ alkyl), N($C_1$-$C_6$ alkyl)$_2$, $C_3$-$C_7$ cycloalkyl, $C_3$-$C_7$ heterocyclyl, aryl, heteroaryl, —O($C_3$-$C_7$ cycloalkyl), —O($C_3$-$C_7$ heterocyclyl), —O(aryl) or —O(heteroaryl) groups.

"$C_3$-$C_7$ cycloalkyl" refers to a saturated 3 to 7 membered carbocyclic ring. Examples of such groups include cyclopropyl, cyclobutyl, cyclopentyl, cyclohexyl and cycloheptyl. "$C_3$-$C_{11}$ cycloalkyl" has similar meanings except that it contains from 3 to 11 membered carbocyclic ring.

"$C_5$-$C_7$ cycloalkenyl" refers to a 5 to 7 membered carbocyclic ring having at least one ring carbon-carbon double bond. "$C_5$-$C_{11}$ cycloalkenyl" has similar meanings except that it contains from 5 to 11 membered carbocyclic ring.

"$C_3$-$C_7$ heterocyclyl" refers to a 3 to 7 membered ring system having at least one heteroatom chosen from N, O or S and optionally being partially unsaturated. Examples of such groups include morpholino, pyrrolidino, piperidinyl, piperazinyl, tetrahydrofuranyl. "$C_3$-$C_{11}$ heterocyclyl" has similar meanings except that it contains from 3 to 11 membered ring system.

In the present specification, "halo" or "halogen" refer to fluoro, chloro, bromo or iodo.

The term "aryl" in the context of the present specification refers to a ring system having from 5 to 14 ring carbon atoms and containing up to three rings, at least one of which has aromatic character. Examples of aryl groups are benzene, biphenyl and naphthalene.

The term "heteroaryl" in the context of the present specification refers to a ring system having from 5 to 14 ring atoms, one or more of which is a heteroatom selected from N, O and S and containing up to three rings, at least one of which has aromatic character. Examples of heteroaryl groups include pyridyl, pyrazinyl, pyrimidinyl, pyridazinyl, pyrazolyl, oxazolyl, furanyl, thienyl, quinolinyl, isoquinolyl, quinazolyl, thiazolyl, benzothiazolyl, benzoxazolyl, benzimidazolyl, indolyl, indazolyl, imidazolyl, benzimidazolinyl and benzodioxolyl ring systems.

When cycloalkyl, heterocyclyl, aryl and heteroaryl groups are substituted, there may be one or more substituents selected from:

(i) $C_1$-$C_{10}$ alkyl, $C_2$-$C_{10}$ alkenyl or $C_2$-$C_{10}$ alkynyl, any of which may be substituted as defined above; or (ii) $C_3$-$C_7$ cycloalkyl, $C_5$-$C_7$ cycloalkenyl, aryl, heteroaryl, $C_3$-$C_7$ heterocyclyl, any of which may, in turn, be substituted with one or more substituents selected from halogen, —OR10, —SR10, —NR10R10', —C(O)R10, —CO$_2$R10, —C(O)NR10R10', —S(O)R10, —SO$_2$R10, —SO$_2$NR10R10', —OC(O)R10', —N(R10)C(O)R10', —N(R10)SO$_2$R10', —CN, or —NO$_2$; wherein R10 and R10' are each independently hydrogen, $C_1$-$C_6$ alkyl, $C_2$-$C_5$ alkenyl or $C_2$-$C_5$ alkynyl; or (iii) —OR11, —SR11, —NR11R11', —C(O)R11, —CO$_2$R11, —C(O)NR11R11', —S(O)R11, —SO$_2$R11, or —SO$_2$NR11R11', —OC(O)R11', —N(R11)C(O)R11', or —N(R11)SO$_2$R11', halogen, —CN, or —NO$_2$; wherein R11 and R11' are each independently hydrogen, $C_1$-$C_6$ alkyl, $C_2$-$C_5$ alkenyl, $C_2$-$C_5$ alkynyl, $C_3$-$C_{11}$ cycloalkyl, $C_5$-$C_{11}$ cycloalkenyl, aryl, heteroaryl, or $C_3$-$C_{11}$ heterocyclyl.

The term "$C_1$-$C_6$ alkoxy" refers to the group $C_1$-$C_6$ alkyl-O—.

The term "$C_1$-$C_6$ alkylthiol" refers to the group $C_1$-$C_6$ alkyl-S—.

The term "$C_1$-$C_6$ alkylamino" refers to the group $C_1$-$C_6$ alkyl attached to an amino moiety.

Appropriate pharmaceutically and veterinarily acceptable salts of the compounds of general formulae (I) and (II) include basic addition salts such as sodium, potassium, calcium, aluminium, zinc, magnesium and other metal salts as well as choline, diethanolamine, ethanolamine, ethyl diamine and other well known basic addition salts.

Where appropriate, pharmaceutically or veterinarily acceptable salts may also include salts of organic acids, especially carboxylic acids, including but not limited to acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, pamoate, pectinate, 3-phenylpropionate, picrate, pivalate, proprionate, tartrate, lactobionate, pivolate, camphorate, undecanoate and succinate; organic sulfonic acids such as methanesulfonate, ethanesulfonate, 2-hydroxyethane sulfonate, camphorsulfonate, 2-naphthalenesulfonate, benzenesulfonate, p-chlorobenzenesulfonate and p-toluenesulfonate; and inorganic acids such as hydrochloride, hydrobromide, hydroiodide, sulfate, bisulfate, hemisulfate, thiocyanate, persulfate, phosphoric and sulfonic acids.

Salts which are not pharmaceutically or veterinarily acceptable may still be valuable as intermediates.

Prodrugs are any covalently bonded compounds which release the active parent drug according to general formula (I) in vivo.

In the compounds of the first aspect of the invention, it is greatly preferred that, independently or in any combination:
R8 is H; and
R9 is H.

Other preferred compounds include those in which R1 is hydrogen or $C_1$-$C_6$ alkyl, which may optionally be substituted with halo. It is more preferred that R1 is hydrogen or $C_1$-$C_3$ alkyl, but particularly useful compounds are those in which R1 is hydrogen, methyl or ethyl.

More active compounds of general formula (I) include those in which, in addition to R8 and R9, R4 and R5 are also hydrogen.

In other preferred compounds of general formula (I), one or both of R2 and R3 is aryl, heteroaryl, $C_3$-$C_7$ cycloalkyl, $C_3$-$C_7$ heterocyclyl or $C_1$-$C_6$ alkyl, any of which may optionally be substituted with one or more substituents chosen from halogen, OH, $C_1$-$C_6$ alkoxy, O—$C_3$-$C_7$ cycloalkyl, aryl, heteroaryl, $C_3$-$C_7$ heterocyclyl, O—$C_3$-$C_7$ heterocyclyl, O-aryl, O-heteroaryl moieties, or, except when R2 or R3 is alkyl, $C_1$-$C_6$ alkyl, any of which may be substituted with methyl or halo.

It is more preferred that one of R2 and R3 is as defined above and that the other of R2 and R3 is hydrogen.

Particularly useful compounds include those in which R2 is hydrogen and R3 is furanyl, thienyl, phenyl or benzo[1,3]dioxolyl, any of which may be substituted by one or more halo, methyl, methoxy, hydroxyl or phenyl, pyridyl, pyrazole, indolyl, methylpyrazole, morpholino groups, any of which may optionally be substituted Especially preferred R3 groups include 2-methoxyphenyl, 2-fluorophenyl, 2-bromophenyl, 2-bromo-4-fluorophenyl, 4-methylphenyl, 3-fluorophenyl, 4-fluorophenyl, 4-chlorophenyl, phenyl, 2,6-dimethoxyphenyl, 2,6-difluorophenyl, 2,4-difluorophenyl, 2-morpholinophenyl, 1-(2-phenoxyethanol), 4-benzo[1,3]dioxolyl, biphenyl, pyridylphenyl, for example 2-pyridylphenyl such as 2-(2-pyridyl)phenyl, 2-(3-pyridyl)phenyl and 2-(4-pyridyl)phenyl, 4-fluoro-2-pyridylphenyl, indolylphenyl, for example 2-(1H-indol-7-yl)-phenyl, 2-(1H-indol-4-yl)-phenyl, 2(1-methylpyrazol-4-yl)phenyl and 4-fluoro-2(1-methylpyrazol-4-yl)phenyl.

In other preferred compounds of general formula (I), R6 is hydrogen, optionally substituted $C_1$-$C_6$ alkyl, optionally substituted $C_2$-$C_6$ alkenyl, optionally substituted $C_2$-$C_6$ alkynyl, optionally substituted aryl; or R6 is C(O)C$_1$-C$_6$ alkyl, (CH$_2$)$_n$C(O)OH, (CH$_2$)$_n$C(O)O(C$_1$-C$_2$ alkyl), (CH$_2$)$_n$C(O)-morpholino or C1-C6 alkylN(R14)$_2$, where R14 and n are as defined above.

In particular, R6 is hydrogen, methyl, ethyl, propyl, butyl, hexynyl, phenyl, —C$_1$-C$_3$ alkylN(C$_1$-C$_2$ alkyl)$_2$, morpholino (C$_1$-C$_3$ piperazinyl(C$_1$-C$_3$ alkyl)-, 4-methylpiperazinyl(C$_1$-C$_3$ pyrrolidino(C$_1$-C$_3$ alkyl), —C(O)methyl, —(CH$_2$)$_{1-3}$C(O)OH, —(CH$_2$)$_{1-3}$C(O)O(C$_1$-C$_2$ alkyl) or —CH$_2$C(O)-morpholino.

In one embodiment of the invention, the compound 2-amino-7,7-dimethyl-7,8-dihydro-6H-quinazolin-5-one oxime (i.e. a compound of formula (I) in which R1, R4, R5, R6, R8 and R9 are all hydrogen and R2 and R3 are both methyl) is specifically excluded from the scope of the compounds of the invention.

In a preferred embodiment, the compounds of general formula (I) have an IC$_{50}$ value for inhibiting Hsp90 activity less than or equal to 100 µM. In more preferred embodiments, the IC$_{50}$ value is less than or equal to 50 µM, even more preferred with an IC$_{50}$ value less than or equal to 25 µM. Still more preferred embodiment have IC$_{50}$ values less than or equal to 10 µM, and even more preferred embodiments have IC$_{50}$ values less than or equal to 1 µM, A representative assay for determining Hsp90 inhibitory activity is described in Example 7.

Particularly preferred compounds of general formula (I) include:
1. 2-Amino-7-(4-chloro-phenyl)-7,8-dihydro-6H-quinazolin-5-one oxime
2. 2-Amino-7-(4-chloro-phenyl)-7,8-dihydro-6H-quinazolin-5-one O-methyl-oxime
3. 2-Amino-7-phenyl-7,8-dihydro-6H-quinazolin-5-one oxime
4. 2-Amino-7-phenyl-7,8-dihydro-6H-quinazolin-5-one O-methyl-oxime
5. 2-Amino-7-phenyl-7,8-dihydro-6H-quinazolin-5-one oxime-O-acetyl
6. 2-Amino-7-(4-fluoro-phenyl)-7,8-dihydro-6H-quinazolin-5-one oxime 7. 2-Amino-7-(4-fluoro-phenyl)-7,8-dihydro-6H-quinazolin-5-one O-methyl-oxime
8. 2-Amino-7-(4-fluoro-phenyl)-7,8-dihydro-6H-quinazolin-5-one O-ethyl-oxime
9. [2-Amino-7-(4-fluoro-phenyl)-7,8-dihydro-6H-quinazolin-5-ylideneaminooxy]-acetic acid
10. 2-Amino-7-(4-fluoro-phenyl)-7,8-dihydro-6H-quinazolin-5-one O-(2-morpholin-4-yl-2-oxo-ethyl)-oxime
11. 2-Amino-7-(4-fluoro-phenyl)-7,8-dihydro-6H-quinazolin-5-one O-propyl-oxime
12. 2-Amino-7-(4-fluoro-phenyl)-7,8-dihydro-6H-quinazolin-5-one O-butyl-oxime
13. 4-[2-Amino-7-(4-fluoro-phenyl)-7,8-dihydro-6H-quinazolin-5-ylideneaminooxy]-butyric acid ethyl ester
14. 4-[2-Amino-7-(4-fluoro-phenyl)-7,8-dihydro-6H-quinazolin-5-ylideneaminooxy]-butyric acid
15. 2-Amino-7-(4-fluoro-phenyl)-7,8-dihydro-6H-quinazolin-5-one O-(2-morpholin-4-yl-ethyl)-oxime
16. 2-Amino-7-(2-methoxy-phenyl)-7,8-dihydro-6H-quinazolin-5-one oxime
17. 2-Amino-7-(2-methoxy-phenyl)-7,8-dihydro-6H-quinazolin-5-one O-methyl-oxime
18. 2-Amino-7-thien-2-yl-7,8-dihydro-6H-quinazolin-5-one oxime
19. 2-Amino-7-thien-2-yl-7,8-dihydro-6H-quinazolin-5-one O-methyl-oxime
20. 2-Amino-7-(2-fluoro-phenyl)-7,8-dihydro-6H-quinazolin-5-one oxime
21. 2-Amino-7-(2-fluoro-phenyl)-7,8-dihydro-6H-quinazolin-5-one O-methyl-oxime
22. 2-Amino-7-p-tolyl-7,8-dihydro-6H-quinazolin-5-one oxime
23. 2-Amino-7-p-tolyl-7,8-dihydro-6H-quinazolin-5-one O-methyl-oxime
24. 2-Amino-7-(2-bromo-phenyl)-7,8-dihydro-6H-quinazolin-5-one oxime
25. 2-Amino-7-(2-bromo-4-fluoro-phenyl)-7,8-dihydro-6H-quinazolin-5-one oxime
26. 2-Amino-7-(2,4-difluoro-phenyl)-7,8-dihydro-6H-quinazolin-5-one oxime
27. 2-Amino-7-(2,6-dimethoxy-phenyl)-7,8-dihydro-6H-quinazolin-5-one oxime
28. 2-Amino-7-benzo[1,3]dioxol-4-yl-7,8-dihydro-6H-quinazolin-5-one oxime
29. 2-Amino-7-(2-morpholin-4-yl-phenyl)-7,8-dihydro-6H-quinazolin-5-one oxime
30. 2-Amino-7-(4-fluoro-phenyl)-4-methyl-7,8-dihydro-6H-quinazolin-5-one oxime
31. 2-Amino-7-(4-fluoro-phenyl)-4-methyl-7,8-dihydro-6H-quinazolin-5-one O-methyl-oxime
32. 2-Amino-7-(4-fluoro-phenyl)-4-methyl-7,8-dihydro-6H-quinazolin-5-one O-(2-dimethylamino-ethyl)-oxime
33. 2-Amino-7-furan-2-yl-4-methyl-7,8-dihydro-6H-quinazolin-5-one oxime
34. 2-Amino-7-furan-2-yl-4-methyl-7,8-dihydro-6H-quinazolin-5-one O-methyl-oxime
35. 2-Amino-7-furan-2-yl-4-methyl-7,8-dihydro-6H-quinazolin-5-one O-(2-dimethylamino-ethyl)-oxime
36. 2-Amino-4-methyl-7-phenyl-7,8-dihydro-6H-quinazolin-5-one oxime
37. 2-Amino 1-methyl-7-phenyl-7,8-dihydro-6H-quinazolin-5-one O-methyl-oxime
38. 2-Amino-7-thien-2-yl-4-methyl-7,8-dihydro-6H-quinazolin-5-one oxime
39. 2-Amino-7-thien-2-yl-4-methyl-7,8-dihydro-6H-quinazolin-5-one O-methyl-oxime
40. 2-Amino-4-methyl-7-p-tolyl-7,8-dihydro-6H-quinazolin-5-one oxime
41. 2-Amino-4-methyl-7-p-tolyl-7,8-dihydro-6H-quinazolin-5-one O-methyl-oxime
42. 2-Amino-7-(2-methoxy-phenyl)-4-methyl-7,8-dihydro-6H-quinazolin-5-one oxime
43. 2-Amino-7-(2-methoxy-phenyl)-4-methyl-7,8-dihydro-6H-quinazolin-5-one O-methyl-oxime
44. 2-Amino-7-(3-fluoro-phenyl)-4-methyl-7,8-dihydro-6H-quinazolin-5-one oxime
45. 2-Amino-7-(3-fluoro-phenyl)-4-methyl-7,8-dihydro-6H-quinazolin-5-one O-methyl-oxime
46. 2-Amino-7-(2-fluoro-phenyl)-4-methyl-7,8-dihydro-6H-quinazolin-5-one oxime
47. 2-Amino-7-(2-fluoro-phenyl)-4-methyl-7,8-dihydro-6H-quinazolin-5-one O-methyl-oxime
48. 2-Amino-7-(2-bromo-phenyl)-4-methyl-7,8-dihydro-6H-quinazolin-5-one oxime
49. 2-Amino-7-(2,6-dimethoxy-phenyl)-4-methyl-7,8-dihydro-6H-quinazolin-5-one oxime
50. 2-Amino-7-benzo[1,3]dioxol-4-yl-4-methyl-7,8-dihydro-6H-quinazolin-5-one oxime
51. 2-Amino-7-(4-fluoro-2-pyridin-3-yl-phenyl)-7,8-dihydro-6H-quinazolin-5-one oxime
52. 2-Amino-7-biphenyl-2-yl-7,8-dihydro-6H-quinazolin-5-one oxime
53. 2-Amino-7-biphenyl-2-yl-7,8-dihydro-6H-quinazolin-5-one O-methyl-oxime
54. (2-Amino-7-biphenyl-2-yl-7,8-dihydro-6H-quinazolin-5-ylideneaminooxy)-acetic acid
55. 2-Amino. 7-biphenyl-2-yl-7,8-dihydro-6H-quinazolin-5-one O-(2-morpholin-4-yl-2-oxo-ethyl)-oxime
56. 2-Amino-7-biphenyl-2-yl-7,8-dihydro-6H-quinazolin-5-one O-ethyl-oxime
57. 2-Amino-7-biphenyl-2-yl-7,8-dihydro-6H-quinazolin-5-one O-propyl-oxime
58. 2-Amino-7-biphenyl-2-yl-7,8-dihydro-6H-quinazolin-5-one O-butyl-oxime
59. 4-(2-Amino-7-biphenyl-2-yl-7,8-dihydro-6H-quinazolin-5-ylideneaminooxy)-butyric acid ethyl ester
60. 4-(2-Amino-7-biphenyl-2-yl-7,8-dihydro-6H-quinazolin-5-ylideneaminooxy)-butyric acid
61. 2-Amino-7-biphenyl-2-yl-7,8-dihydro-6H-quinazolin-5-one O-(2-morpholin-4-yl-ethyl)-oxime
62. 2-Amino-7-(2-pyridin-2-yl-phenyl)-7,8-dihydro-6H-quinazolin-5-one oxime
63. 2-Amino-7-(2-pyridin-3-yl-phenyl)-7,8-dihydro-6H-quinazolin-5-one oxime
64. 2-Amino-7-(2-pyridin-4-yl-phenyl)-7,8-dihydro-6H-quinazolin-5-one oxime
65. 2-Amino-7-[4-fluoro-2-(1-methyl-1H-pyrazol-4-yl)-phenyl]-7,8-dihydro-6H-quinazolin-5-one oxime
66. 2-Amino-7-biphenyl-2-yl-4-methyl-7,8-dihydro-6H-quinazolin-5-one oxime
67. 2-Amino-7-biphenyl-2-yl-4-methyl-7,8-dihydro-6H-quinazolin-5-one O-methyl-oxime
68. 2-Amino-7-biphenyl-2-yl-4-methyl-7,8-dihydro-6H-quinazolin-5-one O-ethyl-oxime
69. (2-Amino-7-biphenyl-2-yl-4-methyl-7,8-dihydro-6H-quinazolin-5-ylideneaminooxy)-acetic acid
70. 2-Amino-7-biphenyl-2-yl-4-methyl-7,8-dihydro-6H-quinazolin-5-one O-(2-morpholin-4-yl-2-oxo-ethyl)-oxime
71. 2-Amino-7-biphenyl-2-yl-4-methyl-7,8-dihydro-6H-quinazolin-5-one O-propyl-oxime
72. 2-Amino-7-biphenyl-2-yl-4-methyl-7,8-dihydro-6H-quinazolin-5-one O-butyl-oxime 73. 4-(2-Amino-7-biphenyl-2-yl-4-methyl-7,8-dihydro-6H-quinazolin-5-ylideneaminooxy)-butyric acid ethyl ester
74. 2-Amino-7-biphenyl-2-yl-4-methyl-7,8-dihydro-6H-quinazolin-5-one O-(3-morpholin-4-yl-propyl)-oxime
75. 2-Amino-7-biphenyl-2-yl-4-methyl-7,8-dihydro-6H-quinazolin-5-one O-[3-(4-methyl-piperazin-1-yl)-propyl]-oxime
76. 2-Amino-7-biphenyl-2-yl-4-methyl-7,8-dihydro-6H-quinazolin-5-one O-[2-(4-methyl-piperazin-1-yl)-ethyl]-oxime
77. 2-Amino-7-biphenyl-2-yl-4-methyl-7,8-dihydro-6H-quinazolin-5-one O-(3-dimethylamino-propyl)-oxime
78. 2-Amino-7-biphenyl-2-yl-4-methyl-7,8-dihydro-6H-quinazolin-5-one O-(2-pyrrolidin-1-yl-ethyl)-oxime
79. 2-Amino-7-biphenyl-2-yl-4-methyl-7,8-dihydro-6H-quinazolin-5-one O-(2-morpholin-4-yl-ethyl)-oxime
80. 2-Amino-7-biphenyl-2-yl-4-methyl-7,8-dihydro-6H-quinazolin-5-one O-(2-diethylamino-ethyl)-oxime
81. 2-Amino-7-biphenyl-2-yl-4-methyl-7,8-dihydro-6H-quinazolin-5-one O-(2-dimethylamino-ethyl)-oxime
82. 2-Amino-7-biphenyl-2-yl-4-methyl-7,8-dihydro-6H-quinazolin-5-one O-(3-piperazin-1-yl-propyl)-oxime
83. 2-Amino-7-biphenyl-2-yl-4-methyl-7,8-dihydro-6H-quinazolin-5-one O-hex-5-ynyl-oxime
84. 2-Amino-4-methyl-7-(2-pyridin-3-yl-phenyl)-7,8-dihydro-6H-quinazolin-5-one oxime
85. 2-Amino-4-methyl-7-(2-pyridin-4-yl-phenyl)-7,8-dihydro-6H-quinazolin-5-one oxime
86. 2-Amino-4-methyl-7-(2-pyridin-2-yl-phenyl)-7,8-dihydro-6H-quinazolin-5-one oxime
87. 2-Amino-7-(5-fluoro-biphenyl-2-yl)-4-methyl-7,8-dihydro-6H-quinazolin-5-one oxime
88. 2-Amino-7-(4-fluoro-biphenyl-2-yl)-4-methyl-7,8-dihydro-6H-quinazolin-5-one O-(3-dimethylamino-propyl)-oxime
89. 2-Amino-7-(4-fluoro-2-pyridin-3-yl-phenyl)-4-methyl-7,8-dihydro-6H-quinazolin-5-one oxime
90. 2-Amino-7-(4-fluoro-2-pyridin-3-yl-phenyl)-4-methyl-7,8-dihydro-6H-quinazolin-5-one O-(3-dimethylamino-propyl)-oxime
91. 2-Amino-4-ethyl-7-(4-fluoro-phenyl)-7,8-dihydro-6H-quinazolin-5-one oxime;

and their stereoisomers, tautomers, pharmaceutically acceptable salts, and prodrugs.

Compounds of general formula (I) may be prepared from compounds of general formula (II)

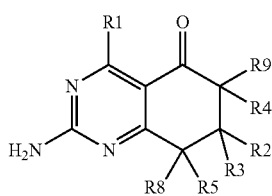

(II)

wherein R1, R2, R3, R4, R5, R8 and R9 are as above defined for general formula (I), by reaction with a compound of general formula (III):

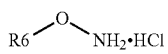

(III)

wherein R6 is as above defined for general formula (I). Typically, the reaction is conducted in a polar organic solvent such as chloroform or pyridine and it may be necessary to heat the reaction mixture, for example to between about 50 and 80° C.

This method is effective for most R6 groups and in particular can be used for compounds in which R6 is hydrogen, alkyl, alkenyl, alkynyl, $(CH_2)_nC(O)R12$, $C_1$-$C_6$ alkyl$N(R14)_2$, where n is 1 to 4, R12 and R14 are as defined above, $C_3$-$C_7$ cycloalkyl, $C_5$-$C_7$ cycloalkenyl, aryl, heteroaryl, or $C_3$-$C_7$ heterocyclyl. The choice of solvent will depend upon the nature of the R6 group. When R6 is hydrogen, chloroform may be the preferred solvent, but when R6 is other than hydrogen, pyridine may be a more suitable solvent.

Compounds of general formula (III) are well known and are either readily available or may be prepared by standard methods known to those of skill in the art.

Compounds of general formula (II) in which R1 is hydrogen may be prepared from compounds of general formula (IV):

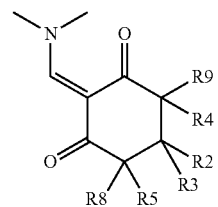

(IV)

wherein R2, R3, R4, R5, R8 and R9 are as above defined for general formula (I); by reaction with guanidine hydrochloride in the presence of a base such as sodium carbonate. The reaction is preferably conducted in a hydrophilic solvent such as ethanol and at elevated temperature, typically under reflux.

Compounds of general formula (IV) may be prepared from compounds of general formula (V):

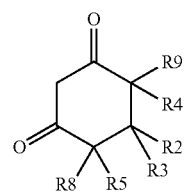

(V)

wherein R2, R3, R4, R5, R8 and R9 are as above defined for general formula (I); by reaction with N,N-dimethylformamide dimethylacetal. The reaction is preferably conducted in a hydrophilic solvent such as ethanol and at elevated temperature, typically under reflux.

Compounds of general formula (V) in which R2, R4, R5, R8 and R9 are all hydrogen may be prepared from compounds of general formula (VI):

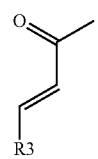

(VI)

wherein R3 is as above defined for general formula (I); by reaction with diethylmalonate in the presence of sodium ethoxide, followed by reaction with a strong base such as sodium hydroxide and subsequent acidification with a strong acid such as concentrated hydrochloric acid.

Compounds of formula (VI) may be prepared from compounds of formula (VII):

(VII)

wherein R3 is as above defined for general formula (I); by reaction with acetone in an aqueous solvent.

Compounds of general formula (VII) are well known in the art and are readily available or may be prepared by standard methods known to those skilled in the art.

Some compounds of general formula (II) are difficult to prepare directly from compounds of general formula (IV). Examples of such compounds are compounds of general formula (II) in which R3 is aryl or heteroaryl substituted with an aryl, heteroaryl, cycloalkyl or heterocyclyl group. These compounds may be prepared from the corresponding compounds of general formula (II) in which R3 is aryl or heteroaryl substituted with bromo by reaction with the appropriate aryl, heteroaryl, cycloalkyl or heterocyclyl boronic acid derivative, as illustrated in Example 4 below.

In an alternative method, compounds of general formula (II) in which R1 is other than hydrogen may be prepared by reacting a compound of general formula (VIII):

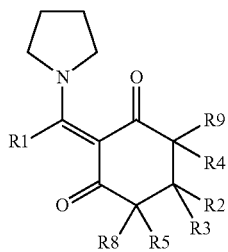

(VIII)

wherein R1, R2, R3, R4, R5, R8 and R9 are as above defined in general formula (I); by reaction with guanidine carbonate in a solvent such as ethanol.

Compounds of general formula (VIII) may be prepared from compounds of general formula (IX):

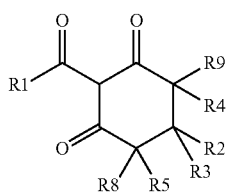

(IX)

wherein R1, R2, R3, R4, R5, R8 and R9 are as defined in general formula (I); with pyrrolidine.

The reaction may be conducted in a polar organic solvent such as chloroform and typically at a temperature of 15 to 25° C., usually at room temperature.

Compounds of general formula (IX) may be prepared by reaction of a compound of general formula (V) as defined above with a compound of general formula (X):

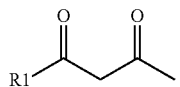

(X)

wherein R1 is as above defined for general formula (I).

Compounds of general formula (X) are well known and are readily available or may be prepared by methods known to those of skill in the art.

Compounds of general formula (I) may also be prepared from other compounds of general formula (I). For example compounds of general formula (I) in which R6 is H or $C_1$-$C_6$ alkyl can be converted into compounds in which R6 is $(CH_2)_n$—$N(C_1$-$C_6$ alkyl$)_2$, where n is an integer of 1 to 4, by reaction with a compound of general formula (XI):

R6-Cl.HCl  (XI)

wherein R6 is $(CH_2)_n$—$N(C_1$-$C_6$ alkyl$)_2$, and n is an integer of 1 to 4. The same method may also be used for cyclic amines such as morpholine, in which case the R6 group is an N-morpholino group.

Compounds of general formula (I) where R6 is H can be converted to compounds where R6 is $C(O)C_1$-$C_6$ alkyl by reaction with the appropriate acid anhydride. For example a compound of general formula (I) where R6 is $C(O)CH_3$ may be obtained by reacting the corresponding compound of general formula (I) where R6 is H with acetic anhydride.

Compounds where R6 is $(CH_2)_n COO(C_1$-$C_6$ alkyl) can be hydrolysed to give the corresponding carboxylic acid using standard methods of hydrolysis.

Compounds where R6 is $(CH_2)_n C(O)OH$ can be converted to the corresponding amides by reaction with thionyl chloride to form an acid chloride followed by reaction of the acid chloride with an amine. An example is the preparation of compounds in which R6 is $(CH_2)_n C(O)$-morpholino.

As discussed above, compounds of general formula (I) are useful for the treatment of diseases which are mediated by excessive or inappropriate Hsp90 activity such as cancers, viral infection and inflammatory diseases and conditions.

In another aspect, the present invention provides methods for treating viral infection, inflammatory diseases and conditions and proliferative diseases in a human or animal subject in need of such treatment comprising administering to said subject an amount of a compound or composition of formula (I) effective to reduce or prevent such viral infection, inflammatory diseases or conditions or cellular proliferation in the subject.

The invention also provides the compounds of general formula (I) for use in medicine, especially in the treatment of viral infection, inflammatory diseases or conditions and proliferative diseases such as cancer.

In a further aspect there is provided the use of a compound of general formula (I) in the preparation of an agent for the treatment of viral infection, inflammatory diseases or conditions and proliferative diseases such as cancer.

Cancers which may be treated using the compounds of general formula (I) include lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma.

The compound of general formula (I) may be administered in combination with another agent useful in the treatment of cancer and examples of such agents include agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons and interleukins; adoptive immunotherapy agents; hematopoietic growth factors; agents that induce tumor cell differentiation (e.g., all-trans-retinoic acid); gene therapy reagents; antisense therapy reagents and nucleotides; tumor vaccines; inhibitors of angiogenesis, and the like.

Numerous other examples of chemotherapeutic compounds and anticancer therapies suitable for co-administration with the 2-amino-7,8-dihydro-6H-quinazolin-5-one oxime compounds of the invention are known to those skilled in the art.

In certain embodiments, anticancer agents to be used in combination with compounds of general formula (I) comprise agents that induce or stimulate apoptosis. Agents that induce apoptosis include, but are not limited to, radiation; kinase inhibitors (e.g., Epidermal Growth Factor Receptor [EGFR] kinase inhibitor, Vascular Endothelial Growth Factor Receptor [VEGFR] kinase inhibitor, Fibroblast Growth Factor Receptor [FGFR] kinase inhibitor, Platelet-derived Growth Factor Receptor [PGFR] I kinase inhibitor, and Bcr-Abl kinase inhibitors such as STI-571 [Gleevec or Glivec]); antisense molecules; antibodies [e.g., Herceptin and Rituxan]; anti-estrogens [e.g., raloxifene and tamoxifen]; anti-androgens [e.g., flutamide, bicalutamide, finasteride, aminoglutethamide, ketoconazole, and corticosteroids]; cyclooxygenase 2 (COX-2) inhibitors [e.g., Celecoxib, meloxicam, NS-398, and non-steroidal anti-inflammatory drugs (NSAIDs)]; and cancer chemotherapeutic drugs [e.g., irinotecan (Camptosar), CPT-II, fludarabine (Fludara), dacarbazine (DTIC), dexamethasone, mitoxantrone, Mylotarg, VP-16, cisplatinum, 5-FU, Doxrubicin, Taxotere or Taxol]; cellular signaling molecules; ceramides and cytokines; and staurosparine; and the like.

Preferred anticancer agents for use in combination with compounds of general formula (I) include irinotecan, topotecan, gemcitabine, gefitinib, vatalanib, sunitinib, sorafenib, erlotinib, dexrazoxane, gleevec, herceptin, 5-fluorouracil, leucovorin, carboplatin, cisplatin, taxanes, tezacitabine, cyclophosphamide, vinca alkaloids, imatinib, anthracyclines, rituximab, trastuzumab and topoisomerase I inhibitors.

The compounds of the present invention may also be used to treat other conditions mediated by Hsp90, for example viral conditions such as hepatitis B, hepatitis C and herpes simplex; inflammatory conditions such as rheumatoid arthritis, asthma, multiple sclerosis, type I diabetes, Lupus erythmatosus, psoriasis and inflammatory bowel disease; cystic fibrosis; angiogenesis-related diseases such as diabetic retinopathy, haemangiomas and endometriosis. In addition the compounds may be used to treat brain conditions which may be mediated by Hsp90, for example scrapie or its human equivalent, Creuzfeldt-Jakob disease (CJD), Huntington's disease or Alzheimer's disease or to protect normal cells against chemotherapy-induced toxicity. Another use for the compounds is to resensitise previously resistant fungal strains to antifungal agents such as azoles or echinocandins.

The compound of general formula (I) may be administered in combination with another agent useful in the treatment of inflammation, another anti-viral agent, an anti-fungal agent or an agent useful for treating any of the diseases or conditions listed above.

In yet another aspect of the invention, there is provided a pharmaceutical composition comprising a compound of general formula (I) together with a pharmaceutically acceptable excipient.

The composition may further include one or more additional anti-cancer agent such as those listed above or, alternatively, another anti-inflammatory, anti-viral or anti-fungal agent or an agent useful for treating any of the diseases or conditions listed above.

The pharmaceutical compositions of the present invention may be formulated for administration orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose a fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

Compounds of general formula (I) may be administered to a patient in a total daily dose of, for example, from 0.001 to 1000 mg/kg body weight daily and more preferred from 1.0 to 30 mg/kg body weight daily. Dosage unit compositions may contain such amounts of submultiples thereof to make up the daily dose.

The agents to be employed in combination with the compounds of general formula (I) will be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of general formula (I) and the other agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

Antiestrogens, such as tamoxifen, inhibit breast cancer growth through induction of cell cycle arrest, that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to antiestrogen resistance (Donovan, et al., *Biol. Chem.* 276:40888, 2001). As reported by Donovan et al., inhibition of MAPK signaling through treatment with MEK inhibitor changed the phosphorylation status of p27 in hormone refactory breast cancer cell lines and in so doing restored hormone sensitivity. Accordingly, in one aspect, the compounds of formula (I) or (II) may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-ABL tyrosine kinase. The afflicted patients are responsive to gleevec, a small molecule tyrosine kinase inhibitor, as a result of inhibition of Abl kinase activity. However, many patients with advanced stage disease respond to gleevec initially, but then relapse later due to resistance-conferring mutations in the Abl kinase domain. In vitro studies have demonstrated that BCR-Avl employs the Raf kinase pathway to elicit its effects. In addition, inhibiting more than one kinase in the same pathway provides additional protection against resistance-conferring mutations. Accordingly, in another aspect of the invention, the compounds of formula (I) or (II) are used in combination with at least one additional agent, such as gleevec, in the treatment of hematological cancers, such as chronic myelogenous leukemia (CML), to reverse or prevent resistance to the at least one additional agent.

The present invention will be understood more readily by reference to the following examples.

The following are abbreviations used in the examples:
AcOH: acetic acid
Aq.: aqueous
Boc: tert-butoxycarbonyl
br.s: broad singlet
CHLOROFORM-d: deuterated chloroform
conc.: concentrated
$CHCl_3$: chloroform
$CH_2(COEt_2)_2$: diethyl malonate
d: doublet
dd: doublet of doublets
DCM: dichloromethane
DMF: N,N-dimethylformamide
DMSO: dimethyl sulfoxide
$Et_3N$: triethylamine
EtOAc: ethyl acetate
EtOH: ethanol
g: gram
GC: gas chromatography
h: hour
H: proton
HCl: hydrochloric acid
HPLC: high performance liquid chromatography
Hz: hertz
$IC_{50}$ value: the concentration of an inhibitor that causes a 50% reduction in a measured activity
IPA: isopropanol
iPrOH: isopropanol
LC/MS: liquid chromatography/mass spectrometry
m: multiplet
M: molar
MeOH: methanol
MeOD-$d_4$: deuterated methanol
µl: microliter
µM: micromolar
µmol: micromole
mg: milligram
$MgSO_4$: magnesium sulfate
MHz: megahertz
min: minute
ml: milliliter
mm: millimeter
mmol: milli mole
$Na_2CO_3$: sodium carbonate
NaOAc: sodium acetate
NaOEt: sodium ethoxide
NaOH: sodium hydroxide
NaOMe: sodium methoxide
$Na_2SO_4$: sodium sulphate
$NH_2OH.HCl$: hydroxylamine hydrochloride
nm: nanometer
NMR: nuclear magnetic resonance
ppm: part per million
q: quartet
quin: quintet
s: singlet
sat: saturated
t: triplet
td: triplet of doublets
TFA: trifluoroacetic acid
THF: tetrahydrofuran
TLC: thin layer chromatography
UV: ultraviolet
W: watts Nomenclature for the compounds disclosed in this application was provided using AutoNom 2000 (Automatic Nomenclature) for ISIS/Base, implementing IUPAC standardized nomenclature. Other compounds, intermediates, and starting materials were named using standard IUPAC nomenclature.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure. It is understood that the invention is not limited to the embodiments set forth herein for illustration, but embraces all such forms thereof as come within the scope of the above disclosure.

General Methods

Commercially available reagents and solvents (HPLC grade) were used without further purification.

$^1$H NMR spectra were recorded on a Bruker DRX 500 MHz or a Bruker 400 MHz AV spectrometer or a Bruker DPX 360 or 250 MHz spectrometer in deuterated solvents. Chemical shifts (δ) are in parts per million. Thin-layer chromatography (TLC) analysis was performed with Kieselgel 60 $F_{254}$ (Merck) plates and visualized using UV light.

Analytical HPLC-MS was performed on Agilent HP1100, systems using reverse phase Atlantis dC18 columns (5 μm, 2.1×50 mm), gradient 5-100% B (A=water/0.1% formic acid, B=acetonitrile/0.1% formic acid) over 3 min, injection volume 3 μl, flow=1.0 ml/min. UV spectra were recorded at 215 nm using a Waters 2487 dual wavelength UV detector. Mass spectra were obtained over the range m/z 150 to 850 at a sampling rate of 2 scans per second using Waters ZMD or analytical HPLC-MS was performed on Agilent HP1100, systems using reverse phase Water Atlantis dC18 columns (3 μm, 2.1×100 mm), gradient 5-100% B (A=water/0.1% formic acid, B=acetonitrile/0.1% formic acid) over 7 min, injection volume 3 μl, flow=0.6 ml/min. UV spectra were recorded at 215 nm using a Waters 2996 photo diode array. Mass spectra were obtained over the range m/z 150 to 850 at a sampling rate of 2 scans per second using Waters ZQ. Data were integrated and reported using OpenLynx and OpenLynx Browser software.

Analytical HPLC-MS was also performed on Shimadzu LCMS-2010EV system (MS, pump, PDA) using reversed phase Water Atlantis dC18 columns (3 μm, 2.1×100 mm), gradient 5-100% B (A=Water/0.1% formic acid, B=acetonitrile/0.1% formic acid) over 7 min, injection volume 3 μl, flow=1.0 ml/min. UV spectra were recorded at 215 nm.

HPLC preparative purification of compounds at low or neutral pH prep was performed by UV directed HPLC performed on Gilson Prep LC modules operated with UniPoint software version 5.1 using reversed phase Waters SunFire Prep C18 OBD columns (5 μm, 19×100 mm), gradient 10-100%, B (A=Water/0.1% TFA, B=acetonitrile/0.1% TFA) over 12 min, injection volume 1.0 ml, flow=26 ml/min. UV spectra were recorded at 215 nm. High pH prep was performed on Gilson Prep LC modules operated with UniPoint software version 5.1 using reversed phase Phenomenex Gemini C18 AXIA columns (5 μm, 100×21.2 mm), gradient 10-100%, B (A=2 mM amm. biocarbonate, buffered to pH 10, B=acetonitrile: 2 mM amm biocarbonate 95:5) over 12 min, injection volume 1.0 ml, flow=26 ml/min. UV spectra were recorded at 215 nm.

Compounds were also purified by HPLC by a mass directed collection trigger which comprises of the following modules operated with Waters FractionLynx V4.0 software:

Waters Micromass Platform LCZ single quadrupole mass spectrometer.
Waters 600 solvent delivery module.
Waters 515 ancillary pumps.
Waters 2487 UV detector.
Gilson 215 autosampler and fraction collector Mass directed HPLC with low pH solvents was performed using reversed phase Waters SunFire Prep C18 OBD columns (5 μm 19×100 mm) gradient 10-100%, B (A-Water/0.1% TFA, B=acetonitrile/0.1% TFA) over 10 min, injection volume 1.0 ml, flow=26 ml/min. UV spectra recorded at 215 nm.

General Procedures for the Synthesis of Diketones

Scheme 1

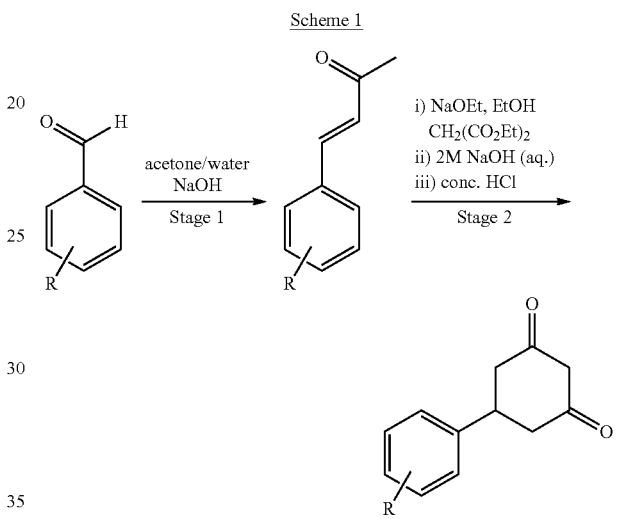

EXAMPLE 1

Synthesis of Diketones a. 5-(2-Methoxy-phenyl)-cyclohexane-1,3-dione

Stage 1: 4-(2-Methoxy-phenyl)-but-3-en-2-one

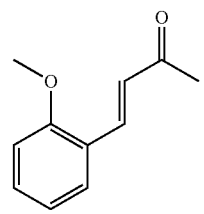

2-Methoxy-benzaldehyde (5 g, 36 mmol) was suspended in a mixture of acetone/water (5 ml/5 ml). A 1% aqueous solution of sodium hydroxide (10 ml) was slowly added to the reaction mixture. The reaction mixture was heated to 65° C. and stirred for 1.5 h. The reaction mixture was cooled to ambient temperature, water (20 ml) and toluene (20 ml) were added to the flask. The organic phase was separated, washed with brine and dried with $MgSO_4$. The solution was filtered and the solvent removed in vacuo to give the required product as a yellow powder. The title compound was used in the next step without further purification.

Yield: 6.09 g (96%)

1H NMR (400 MHz, CHLOROFORM-d) δ ppm 7.82 (1H, d), 7.48 (1H, d), 7.30 (1H, t), 6.83-6.94 (2H, m), 6.68 (1H, d), 3.83 (3H, s), 2.32 (3H, s).

Stage 2:
5-(2-Methoxy-phenyl)-cyclohexane-1,3-dione

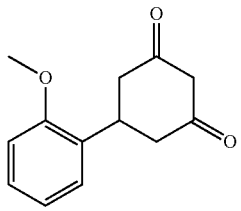 [SMILES: COc1ccccc1C1CC(=O)CC(=O)C1]

To a stirred solution of NaOEt (21% in EtOH) (9.8 ml, 26.5 mmol) under nitrogen was added diethylmalonate (3.7 ml, 24.3 mmol). The reaction mixture was stirred at ambient temperature for 20 min. 4-(2-methoxy-phenyl)-but-3-en-2-one (3.89 g, 22.1 mmol), Stage 1, was dissolved in ethanol (20 ml) and added to the reaction mixture, which was stirred at reflux and monitored by LC-MS until 4-(2-methoxy-phenyl)-but-3-en-2-one was consumed. The reaction mixture was cooled to ambient temperature. An aqueous solution of sodium hydroxide (2M, 10 ml) was added to the reaction mixture, which was heated at 80° C. for 1.5 h. Excess ethanol was removed by evaporation and the aqueous phase was washed with toluene (20 ml). The aqueous phase was acidified with conc. HCl (5 ml) and the reaction mixture was refluxed for 1 h and left to cool to ambient temperature. The compound was extracted with ethyl acetate (2×30 ml), dried with $MgSO_4$ and filtered. The solvent was removed under reduced pressure. The title compound was purified by column chromatography eluting with ethyl acetate/heptane (1/1) to give a beige solid.

Yield: 2.4 g (50%)

Mass spectrum (ES-MS (+ve)) 219 [MH]$^+$, Retention time 1.57 min, 97% UV.

1H NMR (400 MHz, CHLOROFORM-d) δ ppm 7.49-7.57 (1H, m), 7.37 (1H, dd), 7.07-7.26 (2H, m), 4.05 (3H, s), 3.84-3.95 (1H, m), 3.74 (2H, s), 3.09-3.21 (4H, m).

b. 5-(2-Fluoro-phenyl)-cyclohexane-1,3-dione

Stage 1: 4-(2-Fluoro-phenyl)-but-3-en-2-one

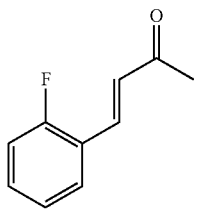

The title compound was prepared from 2-fluoro-benzaldehyde (6.2 g, 50.0 mmol), following the procedure describing the synthesis of 4-(2-methoxy-phenyl)-but-3-en-2-one (example 1/a stage 1).

Yield: 7.3 g (89%)

1H NMR (250 MHz, CHLOROFORM-d) δ ppm 7.68 (1H, d), 7.53-7.62 (1H, m), 7.32-7.44 (1H, m), 7.07-7.23 (2H, m), 6.79 (1H, d), 2.41 (3H, s).

Stage 2: 5-(2-Fluoro-phenyl)-cyclohexane-1,3-dione

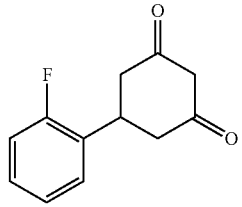 [SMILES: O=C1CC(=O)CC(c2ccccc2F)C1]

The title compound was prepared from 4-(2-fluoro-phenyl)-but-3-en-2-one (7.3 g, 44.5 mmol), stage 1, following the procedure describing the synthesis of 5-(2-methoxy-phenyl)-cyclohexane-1,3-dione (example 1/a stage 2).

Yield: 5.0 g (54%)

Mass spectrum (ES-MS (+ve)) 207 [MH]$^+$, Retention time 1.64 min, 100% UV.

1H NMR (enol isomer) (400 MHz, DMSO-$d_6$) δ ppm 7.38-7.46 (1H, m), 7.26-7.33 (1H, m), 7.11-7.22 (2H, m), 5.29 (1H, s), 3.49-3.62 (1H, m), 2.61 (2H, dd), 2.40 (2H, dd).

c. 5-p-Tolyl-cyclohexane-1,3-dione

Stage 1: 4-p-Tolyl-but-3-en-2-one

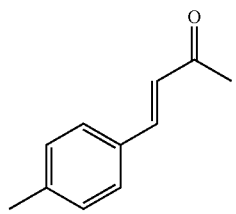

The title compound was prepared from 4-methyl-benzaldehyde (6.0 g, 50.0 mmol), following the procedure describing the synthesis of 4-(2-methoxy-phenyl)-but-3-en-2-one (example 1/a stage 1).

Yield: 8.0 g (100%)

1H NMR (400 MHz, CHLOROFORM-d) δ ppm 7.41-7.55 (3H, m), 7.21 (2H, d), 6.69 (1H, d), 2.38 (3H, s), 2.37 (3H, s).

Stage 2: 5-p-Tolyl-cyclohexane-1,3-dione

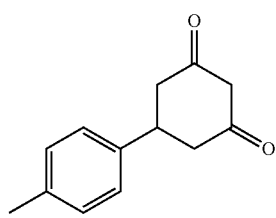

The title compound was prepared from 4-p-tolyl-but-3-en-2-one stage 1 (4.8 g, 30.0 mmol), following the procedure describing the synthesis of 5-(2-methoxy-phenyl)-cyclohexane-1,3-dione (example 1/a stage 2).

Yield: 3.8 g (62%)

Mass spectrum (ES-MS (+ve)) 203 [MH]+, Retention time 1.74 min, 100% UV.

d. 5-(3-Fluoro-phenyl)-cyclohexane-1,3-dione

Stage 1: 4-(3-Fluoro-phenyl)-but-3-en-2-one

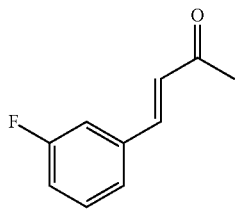

The title compound was prepared from 3-fluoro-benzaldehyde (4.8 g, 40.0 mmol), following the procedure describing the synthesis of 4-(2-methoxy-phenyl)-but-3-en-2-one (example 1/a stage 1).

Yield: 1.0 g (15%)

Mass spectrum (ES-MS (+ve)) 165 [MH]+, Retention time 1.80 min, 100% UV.

Stage 2: 5-(3-Fluoro-phenyl)-cyclohexane-1,3-dione

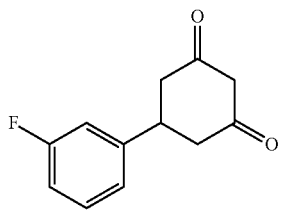 [SMILES: O=C1CC(=O)CC(c2cccc(F)c2)C1]

The title compound was prepared from 4-(3-fluoro-phenyl)-but-3-en-2-one stage 1 (940 mg, 5.73 mmol), following the procedure describing the synthesis of 5-(2-methoxy-phenyl)-cyclohexane-1,3-dione (example 1/a stage 2).

Yield: 800 mg (67%)

Mass spectrum (ES-MS (+ve)) 207 [MH]+, Retention time 1.57 min, 55% UV.

e. 5-(2-Bromo-phenyl)-cyclohexane-1,3-dione

Stage 1: 4-(2-Bromo-phenyl)-but-3-en-2-one

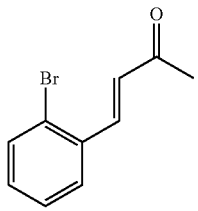

The title compound was prepared from 2-bromo-benzaldehyde (30 g, 162 mmol), following the procedure describing the synthesis of 4-(2-methoxy-phenyl)-but-3-en-2-one (example 1/a stage 1).

Yield: 35 g (97%)

Mass spectrum (ES-MS (+ve)) 226 [MH]+, Retention time 2.01 min, 71% UV.

1H NMR (250 MHz, CHLOROFORM-d) δ ppm 7.90 (1H, d), 7.64-7.61 (2H, m), 7.37-7.22 (2H, m), 6.63 (1H, d), 2.43 (3H, s).

Stage 2: 5-(2-Bromo-phenyl)-cyclohexane-1,3-dione

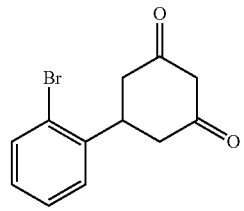 [SMILES: O=C1CC(=O)CC(c2ccccc2Br)C1]

The title compound was prepared from 4-(2-bromo-phenyl)-but-3-en-2-one (1.2 g, 4.44 mmol), stage 1, following the procedure describing the synthesis of 5-(2-methoxy-phenyl)-cyclohexane-1,3-dione (example 1/a stage 2).

Yield: 362 mg (31%)

Mass spectrum (ES-MS (+ve)) 267/269 [MH]+, Retention time 1.71 min, 100% UV.

1H NMR (250 MHz, CHLOROFORM-d) δ ppm 7.52 (1H, dd), 7.17-7.27 (3H, m), 7.00-7.11 (1H, m), 5.93 (1H, s), 3.66-3.82 (1H, m), 2.37-2.67 (4H, m).

f. 5-(2-Bromo-4-fluoro-phenyl)-cyclohexane-1,3-dione

Stage 1: 4-(2-Bromo-4-fluoro-phenyl)-but-3-en-2-one

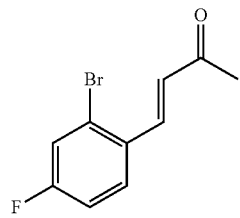

The title compound was prepared from 2-bromo-4-fluoro-benzaldehyde (30 g, 148 mmol), following the procedure describing the synthesis of 4-(2-methoxy-phenyl)-but-3-en-2-one (example 1/a stage 1).

Yield: 34 g (96%)

Mass spectrum (ES-MS (+ve)) 244 [MH]+, Retention time 1.99 min, 93% UV.

1H NMR (250 MHz, CHLOROFORM-d) δ ppm 7.83 (1H, d), 7.62 (1H, dd), 7.38 (1H, dd), 7.08 (1H, td), 6.57 (1H, d), 2.42 (3H, s).

Stage 2: 5-(2-Bromo-4-fluoro-phenyl)-cyclohexane-1,3-dione

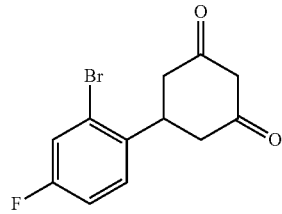 [SMILES: O=C1CC(=O)CC(c2ccc(F)cc2Br)C1]

The title compound was prepared from 4-(2-bromo-4-fluoro-phenyl)-but-3-en-2-one (34 g, 142 mmol), stage 1, following the procedure describing the synthesis of 5-(2-methoxy-phenyl)-cyclohexane-1,3-dione (example 1/a stage 2).

Yield: 29 g (72%)

Mass spectrum (ES-MS (+ve)) 286 [MH]$^+$, Retention time 1.72 min, 98% UV.

1H NMR (500 MHz, MeOD-d$_4$) δ ppm 6.21 (1H, dd), 6.16 (1H, dd), 5.88 (1H, td), 4.18 (1H, s), 2.49-2.57 (1H, m), 1.34-1.43 (2H, m), 1.26-1.33 (2H, m).

The following compounds were also synthesized using a route equivalent to that described above with appropriately chosen starting materials:

- 5-(4-Chloro-phenyl)-cyclohexane-1,3-dione (starting material for compounds 1 and 2);
- 5-Phenyl-cyclohexane-1,3-dione (starting material for compounds 3, 4 and 5);
- 5-(4-Fluoro-phenyl)-cyclohexane-1,3-dione (starting material for compounds 6 to 15);
- 5-Thien-2-yl-cyclohexane-1,3-dione (starting material for compounds 18 and 19);
- 5-(2-Furyl)-cyclohexane-1,3-dione (starting material for compounds 33, 34 and 35);
- 5-(2,6-Dimethoxy-phenyl)-cyclohexane-1,3-dione (starting material for compounds 27 and 49);
- 5-(2,4-Difluoro-phenyl)-cyclohexane-1,3-dione (starting material for compound 26);
- 5-Benzo-[1,3]dioxol-4-yl-cyclohexane-1,3-dione (starting material for compounds 28 and 50);
- 5-(2-Morpholin-4-yl-phenyl)-cyclohexane-1,3-dione (starting material for compound 29).

General procedures for the synthesis of 2-amino-7-phenyl-7,8-dihydro-6H-quinazolin-5-one oxime derivatives The stage 3 method A derivatives can be further alkylated or acylated with an R' group (stage 4). The stage 4 derivatives where R'≠H can also be further functionalized with an R" group (stage 5).

EXAMPLE 2

Synthesis of 2-amino-7-phenyl-7,8-dihydro-6H-quinazolin-5-one oxime derivatives Scheme 2 a. 2-Amino-7-(4-chloro-phenyl)-7,8-dihydro-6H-quinazolin-5-one oxime and 2-amino-7-(4-chloro-phenyl)-7,8-dihydro-6H-quinazolin-5-one O-methyl-oxime (Compounds 1 and 2)

Stage 1: 5-(4-Chloro-phenyl)-2-dimethylaminomethylene-cyclohexane-1,3-dione

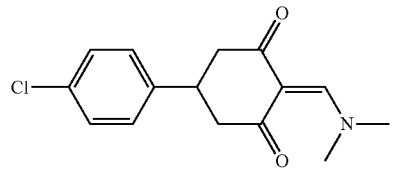 [SMILES: CN(C)C=C1C(=O)CC(c2ccc(Cl)cc2)CC1=O]

5-(4-Chloro-phenyl)-cyclohexane-1,3-dione (1.0 g, 4.5 mmol) was suspended in N,N-dimethylformamide dimethylacetal (5 ml) and heated at reflux for 4 h. The reaction mixture was cooled to ambient temperature and the precipi-

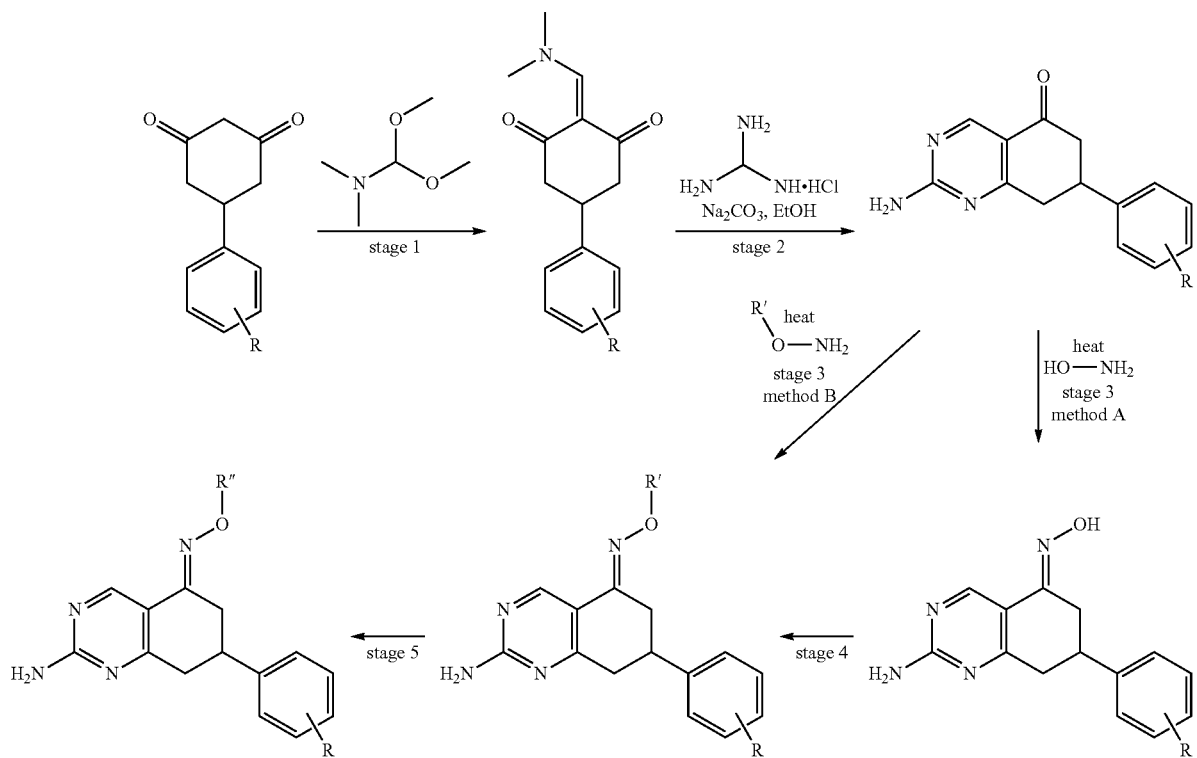

Scheme 2 tate was filtered, washed with diethyl ether and dried under air suction. The required product was obtained as a yellow solid which was used in the next step without further purification.

Yield: 1.05 g (81%)

*Note—LC-MS proved unreliable for purity determination for dimethylamino intermediates due to variable degrees of hydrolysis to hydroxyl derivatives.

1H NMR (400 MHz, CHLOROFORM-d) δ ppm 8.01 (1H, s), 7.24 (2H, d), 7.11 (2H, d), 3.36 (3H, s), 3.23-3.34 (1H, m), 3.16 (3H, s), 2.53-2.73 (4H, m).

Stage 2: 2-Amino-7-(4-chloro-phenyl)-7,8-dihydro-6H-quinazolin-5-one

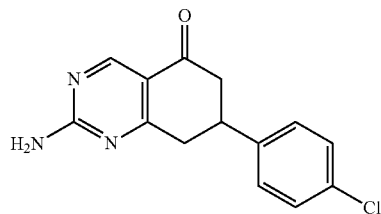 [SMILES: Nc1ncc2c(n1)CC(c1ccc(Cl)cc1)CC2=O]

5-(4-Chloro-phenyl)-2-dimethylaminomethylene-cyclohexane-1,3-dione (0.8 g, 2.89 mmol) from stage 1, guanidine hydrochloride (551 mg, 5.77 mmol) and sodium carbonate (919 mg, 8.67 mmol) were stirred in ethanol (10 ml) at reflux for 4 h. The reaction mixture was cooled to ambient temperature and water (10 ml) was added to the flask. The resulting precipitate was recovered by filtration, washed with water (15 ml), heptane (15 ml) and air dried.

Yield: 744 mg (94%)

Mass spectrum (ES-MS (+ve)) 274 [MH]$^+$, Retention time 1.76 min, 100% UV.

1H NMR (400 MHz, CHLOROFORM-d) δ ppm 8.95 (1H, s), 7.38 (2H, d), 7.24 (2H, d), 5.62 (2H, br. s), 3.43-3.54 (1H, m), 3.06-3.12 (2H, m), 2.87-2.96 (1H, m), 2.75-2.85 (1H, m).

Stage 3

Method A—2-Amino-7-(4-chloro-phenyl)-7,8-dihydro-6H-quinazolin-5-one oxime (Compound 1)

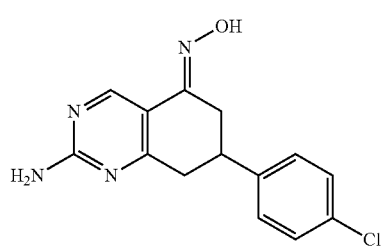 [SMILES: Nc1ncc2c(n1)CC(c1ccc(Cl)cc1)C/C2=N\O]

To a stirred solution of 2-amino-7-(4-chloro-phenyl)-7,8-dihydro-6H-quinazolin-5-one (50 mg, 0.19 mmol), from stage 2, in chloroform (1 ml) at ambient temperature was added hydroxylamine hydrochloride (38 mg, 0.54 mmol) and triethylamine (77 μl, 0.54 mmol). The reaction mixture was heated at 60° C. and stirred for 16 h. The reaction mixture was cooled to ambient temperature. The precipitate which formed was filtered and washed with water (5 ml) and heptane (10 ml) and dried under air suction followed by high vacuum.

Yield: 27 mg (49%)

Mass spectrum (ES-MS (+ve)) 288 [MH]$^+$, Retention time 3.52 min, 82% UV.

1H NMR (400 MHz, DMSO-d$_6$) δ ppm 10.93 (1H, s), 8.64 (1H, s), 7.32-7.47 (4H, m), 6.88 (2H, s), 3.06-3.20 (2H, m), 2.90-3.00 (1H, m), 2.64-2.75 (1H, m), 2.50-2.56 (1H, m).

Stage 3

Method B—2-Amino-7-(4-chloro-phenyl)-7,8-dihydro-6H-quinazolin-5-one O-methyl oxime (Compound 2)

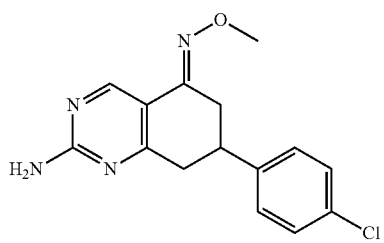 [SMILES: CO/N=C1\CC(c2ccc(Cl)cc2)Cc2nc(N)ncc21]

To a stirred solution of 2-amino-7-(4-chloro-phenyl)-7,8-dihydro-6H-quinazolin-5-one (50 mg, 0.19 mmol), from stage 2, in pyridine (1 ml) at ambient temperature was added methoxylamine hydrochloride (38 mg, 0.54 mmol). The reaction mixture was heated at 110° C. for 45 min. The reaction mixture was cooled to ambient temperature. The precipitate which formed was filtered and washed with water (5 ml), followed by 1M HCl (2 ml). The desired compound was dried under air suction followed by high vacuum.

Yield: 48 mg (86%)

Mass spectrum (ES-MS (+ve)) 303 [MH]$^+$, Retention time 4.36 min, 92% UV.

1H NMR (400 MHz, DMSO-d$_6$) δ ppm 8.64 (1H, s), 7.33-7.41 (4H, m), 7.00 (2H, s), 3.84 (3H, s), 3.06-3.20 (2H, m), 2.91-3.00 (1H, m), 2.64-2.76 (1H, m), 2.53-2.59 (1H, m).

b. 2-Amino-7-phenyl-7,8-dihydro-6H-quinazolin-5-one oxime derivatives (Compounds 3, 4 and 5)

Stage 1: 2-Dimethylaminomethylene-5-phenyl-cyclohexane-1,3-dione

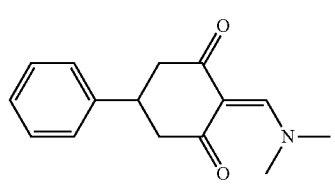 [SMILES: CN(C)C=C1C(=O)CC(c2ccccc2)CC1=O]

The title compound was prepared from 5-phenylcyclohexane-1,3-dione (1.0 g, 5.3 mmol), following the procedure described for the synthesis of 5-(4-chloro-phenyl)-2-dimethylaminomethylene-cyclohexane-1,3-dione (example 2/a stage 1) except that the reaction was run at ambient temperature for 30 min.

Yield: 1.07 g (83%)

Mass spectrum (ES-MS (+ve)) 244 [M+H]⁺, Retention time 1.44 min, 82% UV

Stage 2:
2-Amino-7-phenyl-7,8-dihydro-6H-quinazolin-5-one

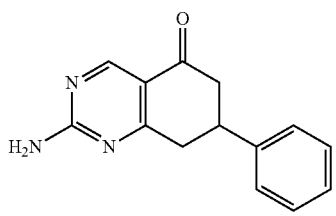 [SMILES: Nc1ncc2c(n1)CC(c1ccccc1)CC2=O]

The title compound was prepared from 2-dimethylaminomethylene-5-phenyl-cyclohexane-1,3-dione (600 mg, 2.46 mmol) from stage 1, guanidine hydrochloride (473 mg, 4.94 mmol) and sodium carbonate (783 mg, 7.38 mmol), following the procedure described for the synthesis of 2-amino-7-(4-chloro-phenyl)-7,8-dihydro-6H-quinazolin-5-one (example 2/a stage 2) except that the mixture was heated to reflux for 16 h.

Yield: 480 mg (81%)

Mass spectrum (ES-MS (+ve)) 240 [MH]⁺, Retention time 1.59 min, 100% UV.

1H NMR (360 MHz, DMSO-d₆) δ ppm 8.66 (1H, s), 7.62 (2H, br. s), 7.30-7.40 (4H, m), 7.21-7.27 (1H, m), 3.42-3.51 (1H, m), 3.14 (1H, dd), 2.82-2.96 (2H, m), 2.62 (1H, d).

Stage 3

Method A—2-Amino-7-phenyl-7,8-dihydro-6H-quinazolin-5-one oxime (Compound 3)

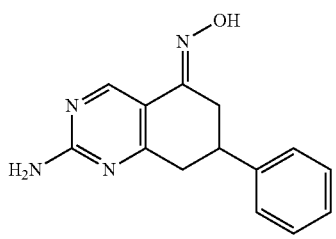 [SMILES: Nc1ncc2c(n1)CC(c1ccccc1)C/C2=N\O]

The title compound was prepared from 2-amino-7-phenyl-7,8-dihydro-6H-quinazolin-5-one (50 mg, 0.21 mmol) from stage 2, hydroxylamine hydrochloride (87 mg, 1.26 mmol) and triethylamine (172 µl, 1.26 mmol), following the procedure described for 2-amino-7-(4-chloro-phenyl)-7,8-dihydro-6H-quinazolin-5-one oxime (example 2/a stage 3—method A) except that the reaction mixture was heated at 60° C. for 72 h.

Yield: 20 mg (38%)

Mass spectrum (ES-MS (+ve)) 255 [MH]⁺, Retention time 3.38 min, 93% UV.

1H NMR (400 MHz, DMSO-d₆) δ ppm 10.91 (1H, s), 8.65 (1H, s), 7.19-7.40 (5H, m), 6.87 (2H, s), 3.06-3.21 (2H, m), 2.91-3.02 (1H, m), 2.72 (1H, d), 2.51-2.58 (1H, m)

Stage 3

Method B—2-Amino-7-phenyl-7,8-dihydro-6H-quinazolin-5-one O-methyl-oxime (Compound 4)

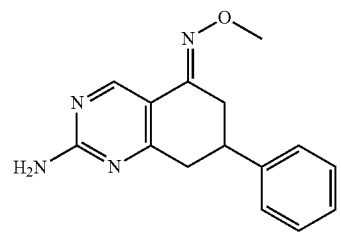 [SMILES: CO/N=C1\CC(c2ccccc2)Cc2nc(N)ncc21]

The title compound was prepared from 2-amino-7-phenyl-7,8-dihydro-6H-quinazolin-5-one (50 mg, 0.21 mmol) from stage 2, and methoxylamine hydrochloride (28 mg, 0.335 mmol) in pyridine (0.5 ml), following the procedure described for 2-amino-7-(4-chloro-phenyl)-7,8-dihydro-6H-quinazolin-5-one O-methyl-oxime (example 2/a stage 3—method B) except that the reaction mixture was stirred at 110° C. for 4 h.

Yield: 38 mg (68%)

Mass spectrum (ES-MS (+ve)) 269 [MH]⁺, Retention time 4.02 min, 93% UV.

1H NMR (400 MHz, DMSO-d₆) δ ppm 8.64 (1H, s), 7.29-7.38 (4H, m), 7.21-7.28 (1H, m), 6.98 (2H, s), 3.84 (3H, s), 3.06-3.18 (2H, m), 2.92-3.01 (1H, m), 2.66-2.79 (1H, m), 2.52-2.62 (1H, m).

Stage 4: 2-Amino-7-phenyl-7,8-dihydro-6H-quinazolin-5-one oxime-O-acetyl (Compound 5)

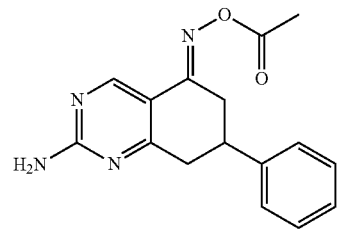 [SMILES: CC(=O)O/N=C1\CC(c2ccccc2)Cc2nc(N)ncc21]

The title compound was prepared from 2-amino-7-phenyl-7,8-dihydro-6H-quinazolin-5-one oxime, compound 3, (43 mg, 0.17 mmol), sodium acetate (82 mg, 1 mmol) and acetic anhydride (1 ml) by heating the reaction mixture at 60° C. for 1 h. The reaction mixture was then allowed to cool to ambient temperature and neutralized to pH=7 with sat. aq. NaHCO₃ and the product extracted with IPA:CHCl₃ 1:1 (2×10 ml) and the organics combined and dried over MgSO₄, filtered and concentrated in vacuo to give pure product.

Yield: 27 mg (54%)

Mass spectrum (ES-MS (+ve)) 297 [MH]⁺, Retention time 3.61+3.74 min, 89% UV.

1H NMR (250 MHz, DMSO-d$_6$) δ ppm 8.77 (1H, s), 7.34-7.37 (5H, m), 7.24 (2H, br.s), 3.15-3.27 (2H, m), 2.97-3.09 (1H, m), 1.70-2.83 (2H, m), 2.15 (3H, s).

c. 2-Amino-7-(4-fluoro-phenyl)-7,8-dihydro-6H-quinazolin-5-one oxime and 2-Amino-7-(4-fluoro-phenyl)-7,8-dihydro-6H-quinazolin-5-one O-methyl-oxime (Compounds 6 and 7)

Stage 1: 2-Dimethylaminomethylene-5-(4-fluoro-phenyl)-cyclohexane-1,3-dione

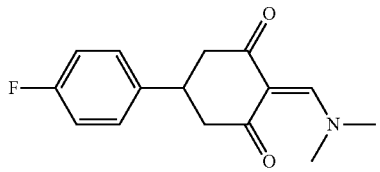 [SMILES: CN(C)C=C1C(=O)CC(c2ccc(F)cc2)CC1=O]

The title compound was prepared from 5-(4-fluoro-phenyl)cyclohexane-1,3-dione (1.0 g, 4.85 mmol), following the procedure described for 5-(4-chloro-phenyl)-2-dimethylaminomethylene-cyclohexane-1,3-dione (example 2/a stage 1) except that the reaction was run at ambient temperature for 10 min.

Yield: 1.25 g (99%)

1H NMR (400 MHz, CHLOROFORM-d) δ ppm 8.11 (1H, s), 7.19-7.24 (2H, m), 6.96-7.08 (2H, m), 3.45 (3H, s), 3.31-3.42 (1H, m), 3.24 (3H, s), 2.60-2.82 (4H, m).

*Note—LC-MS proved unreliable for purity determination for dimethylamino intermediates due to variable degrees of hydrolysis to hydroxyl derivatives.

Stage 2: 2-Amino-7-(4-fluoro-phenyl)-7,8-dihydro-6H-quinazolin-5-one

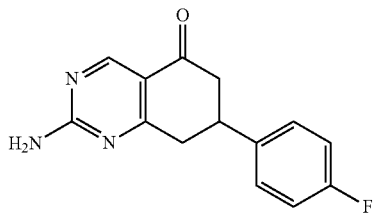 [SMILES: Nc1ncc2c(n1)CC(c1ccc(F)cc1)CC2=O]

The title compound was prepared from 2-dimethylaminomethylene-5-(4-fluoro-phenyl)-cyclohexane-1,3-dione (600 mg, 2.29 mmol) prepared in stage 1, guanidine hydrochloride (438 mg, 4.59 mmol) and sodium carbonate (728 mg, 6.87 mmol), following the procedure described for 2-amino-7-(4-chloro-phenyl)-7,8-dihydro-6H-quinazolin-5-one (example 2/a stage 2).

Yield: 588 mg (100%)

Mass spectrum (ES-MS (+ve)) 258 [MH]$^+$, Retention time 1.64 min, 100% UV.

1H NMR (400 MHz, CHLOROFORM-d) δ ppm 8.92 (1H, s), 7.21-7.26 (2H, m), 7.02-7.11 (2H, m), 5.56 (2H, br. s), 3.42-3.51 (1H, m), 3.05-3.12 (2H, m), 2.71-2.94 (2H, m).

Stage 3

Method A—2-Amino-7-(4-fluoro-phenyl)-7,8-dihydro-6H-quinazolin-5-one oxime (Compound 6)

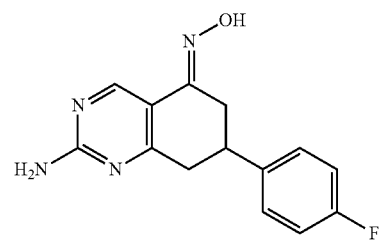 [SMILES: Nc1ncc2c(n1)CC(c1ccc(F)cc1)C/C2=N\O]

The title compound was prepared from 2-amino-7-(4-fluoro-phenyl)-7,8-dihydro-6H-quinazolin-5-one (50 mg, 0.18 mmol) from stage 2, hydroxylamine hydrochloride (75 mg, 1.09 mmol) and triethylamine (154 µl, 1.09 mmol), following the procedure described for the synthesis of 2-amino-7-(4-chloro-phenyl)-7,8-dihydro-6H-quinazolin-5-one oxime (example 2/a stage 3—method A).

Yield: 27 mg (55%)

Mass spectrum (ES-MS (+ve)) 272 [MH]$^+$, Retention time 3.42 min, 83% UV.

1H NMR (400 MHz, DMSO-d$_6$) δ ppm 10.92 (1H, s), 8.65 (1H, s), 7.39 (2H, dd), 7.15 (2H, t), 6.88 (2H, s), 3.07-3.21 (2H, m), 2.90-3.00 (1H, m), 2.70 (1H, d), 2.53-2.62 (1H, m).

Stage 3

Method B—2-Amino-7-(4-fluoro-phenyl)-7,8-dihydro-6H-quinazolin-5-one O-methyl-oxime (Compound 7)

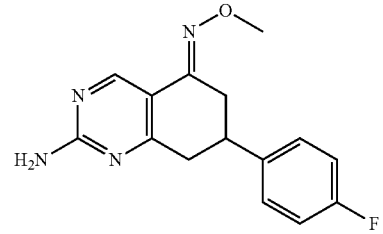 [SMILES: CO/N=C1\CC(c2ccc(F)cc2)Cc2nc(N)ncc21]

The title compound was prepared from 2-amino-7-(4-fluoro-phenyl)-7,8-dihydro-6H-quinazolin-5-one (50 mg, 0.18 mmol) from stage 2, methoxylamine hydrochloride (26 mg, 0.30 mmol) and triethylamine (40 µl, 0.30 mmol), following the procedure described for the synthesis of 2-amino-7-(4-chloro-phenyl)-7,8-dihydro-6H-quinazolin-5-one O-methyl oxime (example 2/a stage 3—method B).

Yield: 13 mg (25%)

Mass spectrum (ES-MS (+ve)) 287 [MH]$^+$, Retention times 4.08 min 67% UV and 3.89 min 31% UV (2 isomers).

1H NMR (400 MHz, DMSO-d$_6$) δ ppm 8.68 (1H, s), 7.39 (2H, dd), 7.16 (2H, t), 3.85 (3H, s), 3.06-3.21 (2H, m), 2.93-3.04 (1H, m), 2.64-2.78 (1H, m), 2.55 (1H, d).

Stage 3

Method B—2-Amino-7-(4-fluoro-phenyl)-7,8-dihydro-6H-quinazolin-5-one O-ethyl-oxime (Compound 8)

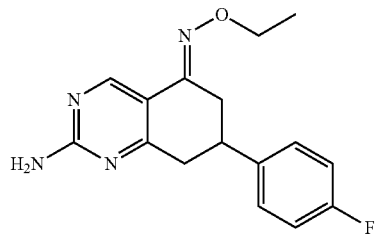 [SMILES: CCO/N=C1\CC(c2ccc(F)cc2)Cc2nc(N)ncc21]

The title compound was prepared from 2-amino-7-(4-fluoro-phenyl)-7,8-dihydro-6H-quinazolin-5-one, from stage 2, and ethoxylamine hydrochloride, following the procedure described for the synthesis of 2-amino-7-(4-chloro-phenyl)-7,8-dihydro-6H-quinazolin-5-one O-methyl oxime (example 2/a stage 3—method B).

Mass spectrum (ES-MS (+ve)) 301 [MH]$^+$, Retention time 4.02+4.23 min, 100% UV.

1H NMR (360 MHz, DMSO-d$_6$) indicated the presence of two oxime stereoisomers in a 1:10 ratio δ ppm 9.35 (1H (1:10), s), 8.66 (1H (10:1), s), 7.40 (2H, dd), 7.15 (2H, t), 6.96 (2H, br. s), 4.10 (2H, q), 3.10-3.17 (2H, m), 2.96 (1H, dd), 2.69 (1H, dd), 2.52-2.57 (1H, m), 1.21 (3H, t).

Stage 3

Method B—[2-Amino-7-(4-fluoro-phenyl)-7,8-dihydro-6H-quinazolin-5-ylideneaminooxy]-acetic acid (Compound 9)

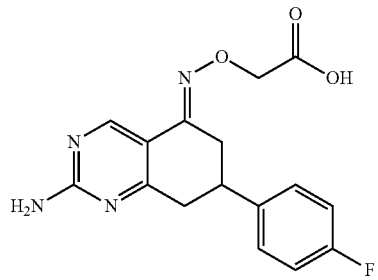 [SMILES: Nc1ncc2c(n1)CC(c1ccc(F)cc1)C/C2=N\OCC(=O)O]

The title compound was prepared from 2-amino-7-(4-fluoro-phenyl)-7,8-dihydro-6H-quinazolin-5-one, from stage 2, and aminooxy-acetic acid, following the procedure described for the synthesis of 2-amino-7-(4-chloro-phenyl)-7,8-dihydro-6H-quinazolin-5-one O-methyl oxime (example 2/a stage 3—method B).

Mass spectrum (ES-MS (+ve)) 331 [MH]$^+$, Retention time 3.39 min, 100% UV.

1H NMR (360 MHz, DMSO-d$_6$) δ ppm 8.62 (1H, s), 7.43 (2H, dd), 7.17 (2H, t), 6.92 (2H, br. s), 4.22 (2H, s), 3.24 (1H, dd), 3.09-3.15 (1H, m), 2.92-3.00 (1H, m), 2.72 (1H, dd), 2.54-2.63 (1H, m).

Stage 5: 2-Amino-7-(4-fluoro-phenyl)-7,8-dihydro-6H-quinazolin-5-one O-(2-morpholin-4-yl-2-oxo-ethyl)-oxime (Compound 10)

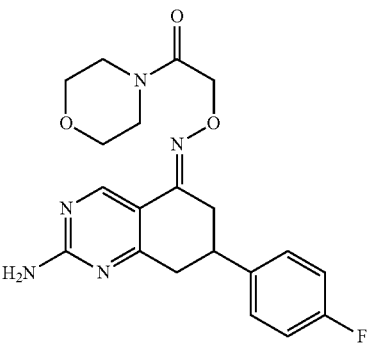 [SMILES: Nc1ncc2c(n1)CC(c1ccc(F)cc1)C/C2=N\OCC(=O)N1CCOCC1]

The title compound was prepared from [2-amino-7-(4-fluoro-phenyl)-7,8-dihydro-6H-quinazolin-5-ylideneaminooxy]-acetic acid, compound 9, and thionyl chloride forming the acid chloride followed by amidation using morpholine and triethylamine in DCM.

Mass spectrum (ES-MS (+ve)) 400 [MH]$^+$, Retention time 3.40 min, 96% UV.

1H NMR (360 MHz, DMSO-d$_6$) δ ppm 8.59 (1H, s), 7.41 (2H, dd), 7.16 (2H, t), 7.04 (2H, br. s), 4.79 (2H, s), 3.54 (4H, br. s), 3.42 (4H, br. s), 3.07-3.24 (2H, m), 2.91-3.04 (1H, m), 2.54-2.77 (2H, m).

Stage 3

Method B—2-Amino-7-(4-fluoro-phenyl)-7,8-dihydro-6H-quinazolin-5-one O-propyl-oxime (Compound 11)

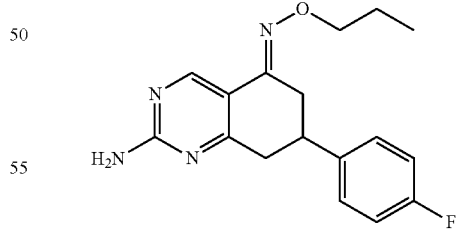

The title compound was prepared from 2-amino-7-(4-fluoro-phenyl)-7,8-dihydro-6H-quinazolin-5-one, from stage 2, and O-propyl-hydroxylamine, following the procedure described for the synthesis of 2-amino-7-(4-chloro-phenyl)-7,8-dihydro-6H-quinazolin-5-one O-methyl oxime (example 2/a stage 3—method B).

Mass spectrum (ES-MS (+ve)) 315 [MH]$^+$, Retention time 4.29+4.52 min, 99% UV.

1H NMR (250 MHz, DMSO-$d_6$) δ ppm 8.65 (1H, s), 7.41 (2H, dd), 7.15 (2H, t), 6.97 (2H, br. s), 4.01 (2H, t), 2.79-3.19 (3H, m), 2.44-2.76 (2H, m), 1.55-1.69 (2H, m), 0.88 (3H, t).

Stage 3

Method B—2-Amino-7-(4-fluoro-phenyl)-7,8-dihydro-6H-quinazolin-5-one O-butyl-oxime (Compound 12)

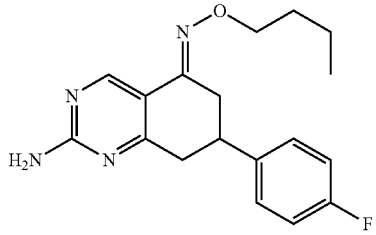 [SMILES: CCCCO/N=C1\CC(c2ccc(F)cc2)Cc2nc(N)ncc21]

The title compound was prepared from 2-amino-7-(4-fluoro-phenyl)-7,8-dihydro-6H-quinazolin-5-one, from stage 2, and O-butyl-hydroxylamine, following the procedure described for the synthesis of 2-amino-7-(4-chloro-phenyl)-7,8-dihydro-6H-quinazolin-5-one O-methyl oxime (example 2/a stage 3—method B).

Mass spectrum (ES-MS (+ve)) 329 [MH]$^+$, Retention time 4.55+4.79 min, 99% UV.

1H NMR (250 MHz, DMSO-$d_6$) δ ppm 8.65 (1H, s), 7.41 (2H, dd), 7.15 (2H, t), 6.97 (2H, br. s), 4.06 (2H, t), 2.86-3.21 (3H, m), 2.51-2.75 (2H, m), 1.49-1.67 (2H, m), 1.24-1.44 (2H, m), 0.88 (3H, t).

Stage 3

Method B—4-[2-Amino-7-(4-fluoro-phenyl)-7,8-dihydro-6H-quinazolin-5-ylideneaminooxy]-butyric acid ethyl ester (Compound 13)

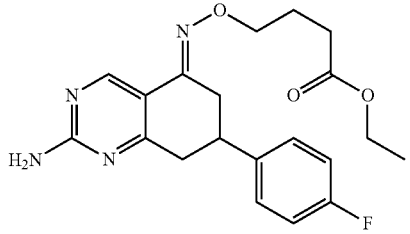

The title compound was prepared from 2-amino-7-(4-fluoro-phenyl)-7,8-dihydro-6H-quinazolin-5-one, from stage 2, and 4-aminooxy-butyric acid ethyl ester, following the procedure described for the synthesis of 2-amino-7-(4-chloro-phenyl)-7,8-dihydro-6H-quinazolin-5-one O-methyl oxime (example 2/a stage 3—method B).

Mass spectrum (ES-MS (+ve)) 387 [MH]$^+$, Retention time 4.32 min, 90% UV.

1H NMR (250 MHz, DMSO-$d_6$) δ ppm 8.64 (1H, s), 7.40 (2H, dd), 7.15 (2H, t), 6.98 (2H, s), 4.07 (2H, t), 4.00 (2H, q), 2.84-3.23 (3H, m), 2.51-2.78 (2H, m), 2.35 (2H, t), 1.73-1.96 (2H, m), 1.13 (3H, t).

The 4-aminooxy-butyric acid ethyl ester was prepared by condensation of 4-bromo-butyric acid ethyl ester on N-hydroxyphthalamide followed by standard hydrazine deprotection.

Stage 5: 4-[2-Amino-7-(4-fluoro-phenyl)-7,8-dihydro-6H-quinazolin-5-ylideneaminooxy]-butyric acid (Compound 14)

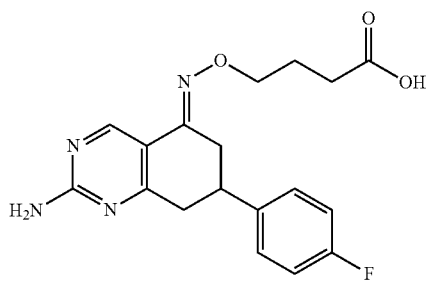 [SMILES: Nc1ncc2c(n1)CC(c1ccc(F)cc1)C/C2=N\OCCCC(=O)O]

The title compound was prepared from 4-[2-amino-7-(4-fluoro-phenyl)-7,8-dihydro-6H-quinazolin-5-ylideneaminooxy]-butyric acid ethyl ester, compound 13, and the ethyl ester hydrolysed under standard conditions.

Mass spectrum (ES-MS (+ve)) 359 [MH]$^+$, Retention time 3.60 min, 99% UV.

1H NMR (250 MHz, DMSO-$d_6$) δ ppm 8.63 (1H, s), 7.37 (2H, dd), 7.14 (2H, t), 6.96 (2H, br. s), 4.05 (2H, t), 3.36 (1H, br. s), 3.11 (2H, d), 2.86-3.03 (1H, m), 2.68 (1H, d), 2.52-2.61 (1H, m), 2.26 (2H, t), 1.77-1.89 (2H, m).

Stage 3

Method B—2-Amino-7-(4-fluoro-phenyl)-7,8-dihydro-6H-quinazolin-5-one O-(2-morpholin-4-yl-ethyl)-oxime (Compound 15)

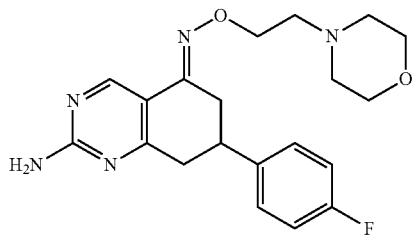 [SMILES: Nc1ncc2c(n1)CC(c1ccc(F)cc1)C/C2=N\OCCN1CCOCC1]

The title compound was prepared from 2-amino-7-(4-fluoro-phenyl)-7,8-dihydro-6H-quinazolin-5-one, from stage 2, and O-(2-morpholin-4-yl-ethyl)-hydroxylamine, following the procedure described for the synthesis of 2-amino-7-(4-chloro-phenyl)-7,8-dihydro-6H-quinazolin-5-one O-methyl oxime (example 2/a stage 3—method B).

Mass spectrum (ES-MS (+ve)) 386 [MH]$^+$, Retention time 2.76 min, 99% UV.

1H NMR (250 MHz, DMSO-$d_6$) δ ppm 8.63 (1H, s), 7.37 (2H, dd), 7.14 (2H, t), 6.97 (2H, s), 4.16 (2H, t), 3.52 (4H, t), 3.10 (2H, d), 2.86-3.02 (1H, m), 2.68 (1H, d), 2.58 (3H, t), 2.39 (4H, t).

The O-(2-morpholin-4-yl-ethyl)-hydroxylamine was prepared by condensation of 4-(2-bromo-ethyl)-morpholine on N-hydroxyphthalamide followed by standard hydrazine deprotection.

d. 2-Amino-7-(2-methoxy-phenyl)-7,8-dihydro-6H-quinazolin-5-one oxime and 2-amino-7-(2-methoxy-phenyl)-7,8-dihydro-6H-quinazolin-5-one O-methyl-oxime (Compounds 16 and 17)

Stage 1: 2-Dimethylaminomethylene-5-(2-methoxy-phenyl)-cyclohexane-1,3-dione

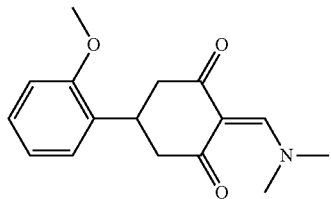 [SMILES: COc1ccccc1C1CC(=O)C(=CN(C)C)C(=O)C1]

The title compound was prepared from 5-(2-methoxy-phenyl)-cyclohexane-1,3-dione (386 mg, 1.77 mmol), example 1/a, and N,N-dimethylformamide dimethylacetal (2 ml), following the procedure described for 5-(4-chloro-phenyl)-2-dimethylaminomethylene-cyclohexane-1,3-dione (example 2/a stage 1) except that the reaction was run at 100° C. for 2 h, after which the solvent was removed by evaporation under reduced pressure to produce the title compound as a brown oil. The title compound was used without further purification in the next step.

Yield: 484 mg (100%)

*Note—LC-MS proved unreliable for purity determination for dimethylamino intermediates due to variable degrees of hydrolysis to hydroxyl derivatives.

Stage 2: 2-Amino-7-(2-methoxy-phenyl)-7,8-dihydro-6H-quinazolin-5-one

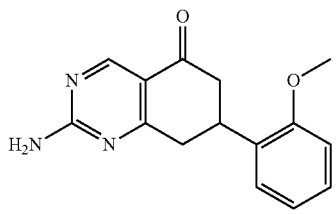 [SMILES: COc1ccccc1C1CC(=O)c2cnc(N)nc2C1]

The title compound was prepared from 2-dimethylaminomethylene-5-(2-methoxy-phenyl)-cyclohexane-1,3-dione (484 mg, 1.77 mmol) from stage 1, guanidine hydrochloride (253 mg, 2.55 mmol) and sodium carbonate (469 mg, 4.42 mmol), following the procedure described for the synthesis of 2-amino-7-(4-chloro-phenyl)-7,8-dihydro-6H-quinazolin-5-one (example 2/a stage 2) except that the mixture was heated at reflux for 2 h. The reaction mixture was cooled to ambient temperature; water (5 ml) was then added. The precipitate formed was filtered and washed with water (5 ml) to afford the title molecule as a brown powder.

Yield: 200 mg (42%)

Mass spectrum (ES-MS (+ve)) 270 [MH]$^+$, Retention time 3.62 min, 99% UV.

1H NMR (400 MHz, DMSO-$d_6$) δ ppm 8.66 (1H, s), 7.61 (2H, br. s), 7.16-7.30 (2H, m), 7.01 (1H, d), 6.94 (1H, t), 3.80 (3H, s), 3.70 (1H, t), 3.09 (1H, dd), 2.78-2.92 (2H, m), 2.54-2.63 (1H, m).

Stage 3

Method A—2-Amino-7-(2-methoxy-phenyl)-7,8-dihydro-6H-quinazolin-5-one oxime (Compound 16)

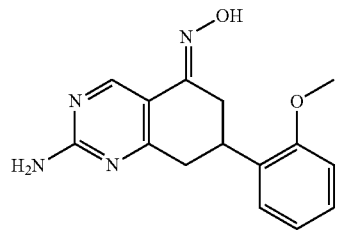 [SMILES: COc1ccccc1C1C/C(=N\O)c2cnc(N)nc2C1]

The title compound was prepared from 2-amino-7-(2-methoxy-phenyl)-7,8-dihydro-6H-quinazolin-5-one (50 mg, 0.18 mmol), from stage 2, and hydroxylamine hydrochloride (64 mg, 0.93 mmol) in pyridine (1 ml), following the procedure describing the synthesis of 2-amino-7-(4-chloro-phenyl)-7,8-dihydro-6H-quinazolin-5-one O-methyl-oxime (example 2/a stage 3—method B).

Yield: 36 mg (71%)

Mass spectrum (ES-MS (+ve)) 285 [MH]$^+$, Retention time 3.46 min, 85% UV.

1H NMR (400 MHz, DMSO-$d_6$) δ ppm 10.89 (1H, s), 8.64 (1H, s), 7.19-7.29 (2H, m), 7.00 (1H, d), 6.93 (1H, t), 6.86 (2H, s), 3.79 (3H, s), 3.30-3.42 (2H, m), 3.08-3.17 (1H, m), 2.93 (1H, dd), 2.63-2.71 (1H, m).

Stage 3

Method B—2-Amino-7-(2-methoxy-phenyl)-7,8-dihydro-6H-quinazolin-5-one O-methyl-oxime (Compound 17)

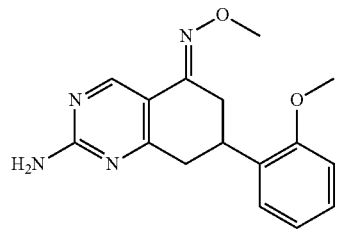 [SMILES: CO/N=C1\CC(c2ccccc2OC)Cc2nc(N)ncc21]

The title compound was prepared from 2-amino-7-(2-methoxy-phenyl)-7,8-dihydro-6H-quinazolin-5-one (50 mg, 0.18 mmol), from stage 2, and methoxylamine hydrochloride (77 mg, 0.93 mmol) in pyridine (1 ml), following the procedure describing the synthesis of 2-amino-7-(4-chloro-phenyl)-7,8-dihydro-6H-quinazolin-5-one O-methyl-oxime (example 2/a stage 3—method B).

Yield: 41 mg (76%)

Mass spectrum (ES-MS (+ve)) 299 [MH]$^+$, Retention time 4.12 min, 83% UV.

1H NMR (400 MHz, DMSO-d$_6$) δ ppm 8.64 (1H, s), 7.19-7.27 (2H, m), 6.88-7.03 (4H, m), 3.84 (3H, s), 3.79 (3H, s), 3.36-3.42 (1H, m), 3.08 (1H, d), 2.94 (1H, dd), 2.67 (1H, d), 2.51-2.59 (1H, m).

e. 2-Amino-7-thien-2-yl-7,8-dihydro-6H-quinazolin-5-one oxime and 2-amino-7-thien-2-yl-7,8-dihydro-6H-quinazolin-5-one O-methyl-oxime (Compounds 18 and 19)

Stage 1: 2-Dimethylaminomethylene-5-thien-2-yl-cyclohexane-1,3-dione

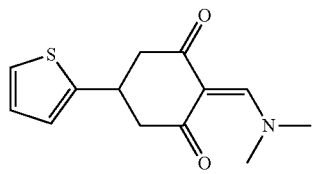 [SMILES: CN(C)C=C1C(=O)CC(c2cccs2)CC1=O]

The title compound was prepared from 5-thien-2-yl-cyclohexane-1,3-dione (388 mg, 2.0 mmol) and N,N-dimethylformamide dimethylacetal (2 ml), following the procedure described for 5-(4-chloro-phenyl)-2-dimethylaminomethylene-cyclohexane-1,3-dione (example 2/a stage 1) except that the reaction mixture was stirred at ambient temperature for 30 min.

Yield: 267 mg (53%)

*Note—LC-MS proved unreliable for purity determination for dimethylamino intermediates due to variable degrees of hydrolysis to hydroxyl derivatives.

Stage 2: 2-Amino-7-thien-2-yl-7,8-dihydro-6H-quinazolin-5-one

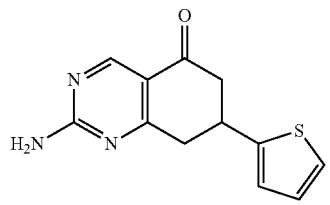 [SMILES: Nc1ncc2c(n1)CC(c1cccs1)CC2=O]

The title compound was prepared from 2-dimethylaminomethylene-5-thien-2-yl-cyclohexane-1,3-dione (267 mg, 1.09 mmol) from stage 1, guanidine hydrochloride (205 mg, 2.14 mmol) and sodium carbonate (342 mg, 3.21 mmol), following the procedure described for the synthesis of 2-amino-7-(4-chloro-phenyl)-7,8-dihydro-6H-quinazolin-5-one (example 2/a stage 2) except that the mixture was heated to reflux for 16 h.

Yield: 200 mg (76%)

Mass spectrum (ES-MS (+ve)) 246 [MH]$^+$, Retention time 3.35 min, 100% UV.

1H NMR (360 MHz, DMSO-d$_6$) δ ppm 8.63 (1H, s), 7.61 (2H, br. s), 7.38 (1H, d), 6.93-7.00 (2H, m), 3.74-3.87 (1H, m), 3.05-3.12 (2H, m), 2.80-2.86 (2H, m).

Stage 3

Method A—2-Amino-7-thien-2-yl-7,8-dihydro-6H-quinazolin-5-one oxime (Compound 18)

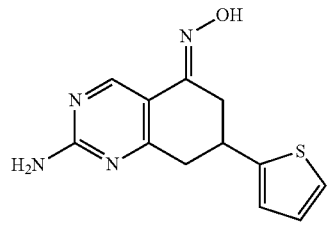 [SMILES: Nc1ncc2c(n1)CC(c1cccs1)C/C2=N\O]

The title compound was prepared from 2-amino-7-thien-2-yl-7,8-dihydro-6H-quinazolin-5-one (50 mg, 0.20 mmol), from stage 2, and hydroxylamine hydrochloride (23 mg, 0.32 mmol) in pyridine (1 ml), following the procedure describing the synthesis of 2-amino-7-(4-chloro-phenyl)-7,8-dihydro-6H-quinazolin-5-one oxime (example 2/a stage 3—method A).

Yield: 27 mg (52%)

*Note—LC-MS proved unreliable for purity determination for this oxime due to hydrolysis to the ketone derivative.

1H NMR (400 MHz, DMSO-d$_6$) δ ppm 10.98 (1H, s), 8.62 (1H, s), 7.37 (1H, d), 6.92-7.00 (2H, m), 6.87 (2H, s), 3.44-3.53 (1H, m), 3.20 (1H, dd), 2.83-3.02 (2H, m), 2.68 (1H, dd).

Stage 3

Method B—2-Amino-7-thien-2-yl-7,8-dihydro-6H-quinazolin-5-one O-methyl-oxime (Compound 19)

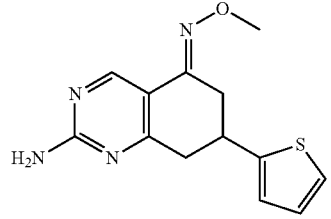 [SMILES: CO/N=C1\CC(c2cccs2)Cc2nc(N)ncc21]

The title compound was prepared from 2-amino-7-thien-2-yl-7,8-dihydro-6H-quinazolin-5-one (50 mg, 0.20 mmol), from stage 2, and methoxylamine hydrochloride (28 mg, 0.32 mmol) in pyridine (1 ml), following the procedure describing the synthesis of 2-amino-7-(4-chloro-phenyl)-7,8-dihydro-6H-quinazolin-5-one O-methyl-oxime (example 2/a stage 3—method B).

Yield: 19 mg (35%)

*Note—LC-MS proved unreliable for purity determination for this oxime due to hydrolysis to the ketone derivative.

1H NMR (250 MHz, DMSO-d$_6$) δ ppm 8.62 (1H, s), 7.37 (1H, dd), 6.91-7.02 (4H, m), 3.86 (3H, s), 3.44-3.56 (1H, m), 3.14 (1H, d), 2.88-2.97 (2H, m), 2.62-2.78 (1H, m).

f. 2-Amino-7-(2-fluoro-phenyl)-7,8-dihydro-6H-quinazolin-5-one oxime and 2-amino-7-(2-fluoro-phenyl)-7,8-dihydro-6H-quinazolin-5-one O-methyl-oxime (Compounds 20 and 21)

Stage 1: 2-Dimethylaminomethylene-5-(2-fluoro-phenyl)-cyclohexane-1,3-dione

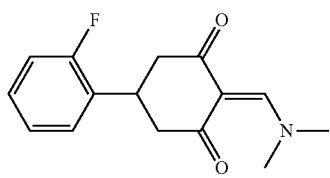

The title compound was prepared from 5-(2-fluoro-phenyl)-cyclohexane-1,3-dione (1.03 g, 5.0 mmol), example 1/b stage 2, and N,N-dimethylformamide dimethylacetal (5 ml), following the procedure described for the synthesis of 5-(4-chloro-phenyl)-2-dimethylaminomethylene-cyclohexane-1,3-dione (example 2/a stage 1) except that the reaction was stirred at 100° C. for 16 h.

Yield: 919 mg (70%)

*Note—LC-MS proved unreliable for purity determination for dimethylamino intermediates due to variable degrees of hydrolysis to hydroxyl derivatives.

Stage 2: 2-Amino-7-(2-fluoro-phenyl)-7,8-dihydro-6H-quinazolin-5-one

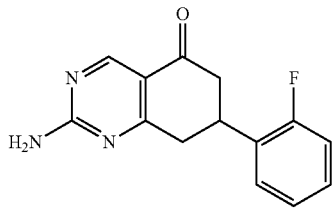 [SMILES: Nc1ncc2c(n1)CC(c1ccccc1F)CC2=O]

The title compound was prepared from 2-dimethylaminomethylene-5-(2-fluoro-phenyl)-cyclohexane-1,3-dione (919 mg, 3.53 mmol) from stage 1, guanidine hydrochloride (673 mg, 7.04 mmol) and sodium carbonate (1.12 g, 10.59 mmol), following the procedure described for the synthesis of 2-amino-7-(4-chloro-phenyl)-7,8-dihydro-6H-quinazolin-5-one (example 2/a stage 2) except that the mixture was heated at reflux for 16 h.

Yield: 780 mg (86%)

Mass spectrum (ES-MS (+ve)) 258 [MH]$^+$, Retention time 3.58 min, 100% UV.

1H NMR (400 MHz, DMSO-d$_6$) δ ppm 8.67 (1H, s), 7.64 (2H, br. s), 7.42 (1H, t), 7.28-7.36 (1H, m), 7.15-7.24 (2H, m), 3.67-3.78 (1H, m), 3.16 (1H, dd), 2.80-2.97 (2H, m), 2.63 (1H, d).

Stage 3

Method A—2-Amino-7-(2-fluoro-phenyl)-7,8-dihydro-6H-quinazolin-5-one oxime (Compound 20)

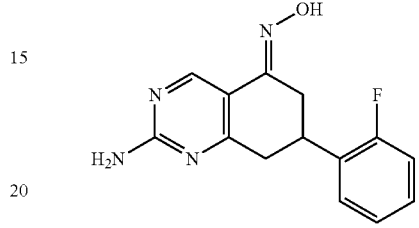

The title compound was prepared from 2-amino-7-(2-fluoro-phenyl)-7,8-dihydro-6H-quinazolin-5-one (50 mg, 0.19 mmol), from stage 2, and hydroxylamine hydrochloride (22 mg, 0.31 mmol) in pyridine (1 ml), following the procedure describing the synthesis of 2-amino-7-(4-chloro-phenyl)-7,8-dihydro-6H-quinazolin-5-one oxime (example 2/a stage 3—method A).

Yield: 36 mg (69%)

*Note—LC-MS proved unreliable for purity determination for this oxime due to hydrolysis to ketone derivative.

1H NMR (400 MHz, DMSO-d$_6$) δ ppm 10.97 (1H, s), 8.65 (1H, s), 7.24-7.47 (2H, m), 7.15-7.22 (2H, m), 6.89 (2H, s), 3.40-3.46 (1H, m), 3.17 (1H, d), 2.99 (1H, dd), 2.73 (1H, d), 2.53-2.61 (1H, m).

Stage 3

Method B—2-Amino-7-(2-fluoro-phenyl)-7,8-dihydro-6H-quinazolin-5-one O-methyl-oxime (Compound 21)

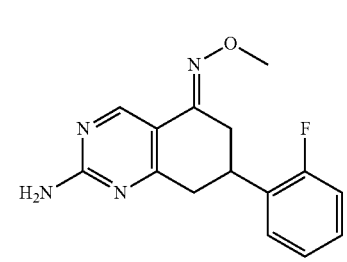 [SMILES: CO/N=C1\CC(c2ccccc2F)Cc2nc(N)ncc21]

The title compound was prepared from 2-amino-7-(2-fluoro-phenyl)-7,8-dihydro-6H-quinazolin-5-one (50 mg, 0.19 mmol), from stage 2, and methoxylamine hydrochloride (27 mg, 0.31 mmol) in pyridine (1 ml), following the procedure describing the synthesis of 2-amino-7-(4-chloro-phenyl)-7,8-dihydro-6H-quinazolin-5-one O-methyl-oxime (example 2/a stage 3—method B).

Yield: 33 mg (61%)

*Note—LC-MS proved unreliable for purity determination for this oxime due to hydrolysis to ketone derivative.

1H NMR (400 MHz, DMSO-d$_6$) δ ppm 8.65 (1H, s), 7.40 (1H, t), 7.27-7.34 (1H, m), 7.15-7.23 (2H, m), 7.01 (2H, s), 3.84 (3H, s), 3.28-3.34 (1H, m), 3.13 (1H, d), 2.99 (1H, dd), 2.73 (1H, d), 2.60 (1H, dd).

g. 2-Amino-7-p-tolyl-7,8-dihydro-6H-quinazolin-5-one oxime and 2-amino-7-p-tolyl-7,8-dihydro-6H-quinazolin-5-one O-methyl-oxime (Compounds 22 and 23)

Stage 1: 2-Dimethylaminomethylene-5-p-tolyl-cyclohexane-1,3-dione

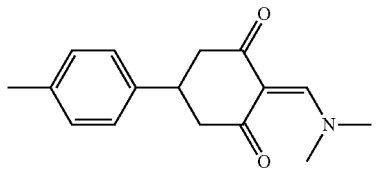

The title compound was prepared from 5-p-tolyl-cyclohexane-1,3-dione (1.0 g, 4.85 mmol), example 1/c, and N,N-dimethylformamide dimethylacetal (5 ml), following the procedure described for 5-(4-chloro-phenyl)-2-dimethylaminomethylene-cyclohexane-1,3-dione (example 2/a stage 1) except that the reaction was stirred at ambient temperature for 16 h.

Yield: 1.06 g (85%)

Mass spectrum (ES-MS (+ve)) 258 [MH]$^+$, Retention time 1.51 min, 96% UV.

Stage 2:

2-Amino-7-p-tolyl-7,8-dihydro-6H-quinazolin-5-one

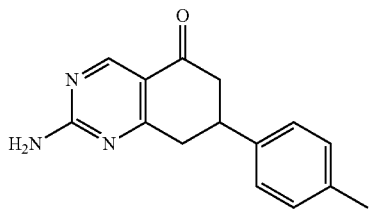 [SMILES: Cc1ccc(C2CC(=O)c3cnc(N)nc3C2)cc1]

The title compound was prepared from 2-dimethylaminomethylene-5-p-tolyl-cyclohexane-1,3-dione (484 mg, 1.77 mmol) from stage 1, guanidine hydrochloride (784 mg, 8.26 mmol) and sodium carbonate (1.31 g, 12.39 mmol), following the procedure described for the synthesis of 2-amino-7-(4-chloro-phenyl)-7,8-dihydro-6H-quinazolin-5-one (example 2/a stage 2) except that the mixture was heated at reflux for 24 h.

Yield: 900 mg (86%)

Mass spectrum (ES-MS (+ve)) 254 [MH]$^+$, Retention time 1.74 min, 100% UV.

1H NMR (400 MHz, DMSO-d$_6$) δ ppm 8.65 (1H, s), 7.61 (2H, br. s), 7.23 (2H, d), 7.14 (2H, d), 3.36-3.47 (1H, m), 3.11 (1H, dd), 2.79-2.93 (2H, m), 2.59 (1H, d), 2.27 (3H, s).

Stage 3

Method A—2-Amino-7-p-tolyl-7,8-dihydro-6H-quinazolin-5-one oxime (Compound 22)

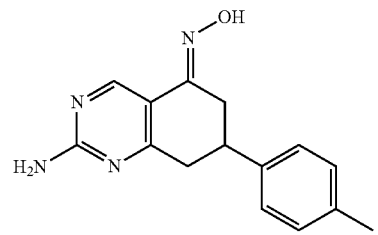

The title compound was prepared from 2-amino-7-p-tolyl-7,8-dihydro-6H-quinazolin-5-one (50 mg, 0.20 mmol), from stage 2, and hydroxylamine hydrochloride (22 mg, 0.31 mmol) in pyridine (1 ml), following the procedure describing the synthesis of 2-amino-7-(4-chloro-phenyl)-7,8-dihydro-6H-quinazolin-5-one oxime (example 2/a stage 3-method A).

Yield: 25 mg (46%)

*Note—LC-MS proved unreliable for purity determination for this oxime due to hydrolysis to ketone derivative.

1H NMR (400 MHz, DMSO-d$_6$) δ ppm 10.89 (1H, s), 8.64 (1H, s), 7.18-7.24 (2H, m), 7.10-7.15 (2H, m), 6.86 (2H, s), 2.86-3.18 (3H, m), 2.69 (1H, dd), 2.48-2.55 (1H, m), 2.27 (3H, s).

Stage 3

Method B—2-Amino-7-p-tolyl-7,8-dihydro-6H-quinazolin-5-one O-methyl-oxime (Compound 23)

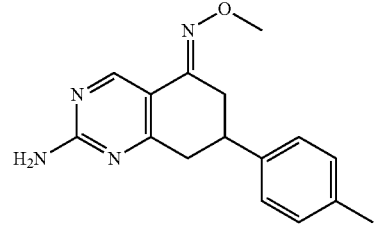

The title compound was prepared from 2-amino-7-p-tolyl-7,8-dihydro-6H-quinazolin-5-one (50 mg, 0.20 mmol), from stage 2, and methoxylamine hydrochloride (27 mg, 0.31 mmol) in pyridine (1 ml), following the procedure describing the synthesis of 2-amino-7-(4-chloro-phenyl)-7,8-dihydro-6H-quinazolin-5-one O-methyl oxime (example 2/a stage 3—method B).

Yield: 24 mg (43%)

*Note—LC-MS proved unreliable for purity determination for this oxime due to hydrolysis to ketone derivative.

1H NMR (400 MHz, DMSO-d$_6$) δ ppm 8.66 (1H, s), 6.98-7.36 (6H, m), 3.85 (3H, s), 3.02-3.14 (2H, m), 2.89-3.01 (1H, m), 2.66-2.76 (1H, m), 2.52-2.60 (1H, m), 2.27 (3H, s).

h. 2-Amino-7-(2-bromo-phenyl)-7,8-dihydro-6H-quinazolin-5-one oxime (Compound 24)

Stage 2: 2-Amino-7-(2-bromo-phenyl)-7,8-dihydro-6H-quinazolin-5-one

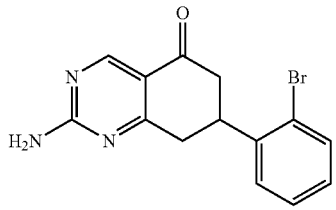 [SMILES: Nc1ncc2c(n1)CC(c1ccccc1Br)CC2=O]

The title compound was prepared from 5-(2-bromo-phenyl)-cyclohexane-1,3-dione (example 1/e), following the procedure described for the synthesis of 2-amino-7-(4-chloro-Phenyl)-7,8-dihydro-6H-quinazolin-5-one (example 2/a stage 2).

Mass spectrum (ES-MS (+ve)) 318/320 [MH]$^+$, Retention time 3.71 min, 100% UV.

1H NMR (360 MHz, DMSO-d$_6$) δ ppm 8.70 (1H, s), 7.66 (3H, d), 7.48-7.55 (1H, m), 7.44 (1H, d), 7.24 (1H, dd), 3.77 (1H, t), 3.10-3.23 (1H, m), 2.82-3.02 (2H, m), 2.64 (1H, m).

Stage 3

Method A—2-Amino-7-(2-bromo-phenyl)-7,8-dihydro-6H-quinazolin-5-one oxime (Compound 24)

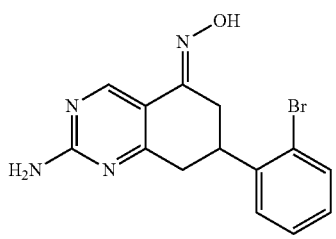 [SMILES: Nc1ncc2c(n1)CC(c1ccccc1Br)C/C2=N\O]

The title compound was prepared, following the procedure describing the synthesis of 2-amino-7-(4-chloro-phenyl)-7,8-dihydro-6H-quinazolin-5-one oxime (example 2/a stage 3—method A).

Mass spectrum (ES-MS (+ve)) 333 [MH]$^+$, Retention time 3.39+3.54 min, 90% UV.

1H NMR (360 MHz, DMSO-d$_6$) indicated the presence of two oxime stereoisomers in a 1:4 ratio δ ppm 11.03 (1H, br. s), 9.51 (1H (1:4), s), 8.66 (1H (4:1), s), 7.64 (1H, d), 7.49 (1H, d), 7.36-7.45 (1H, m), 7.19-7.23 (1H, m), 7.05 (2H (1:4), br. s), 6.90 (2H (4:1), br. s), 3.21 (1H, d), 2.89-3.05 (2H, m), 2.72 (1H, d), 2.62 (1H, d).

i. 2-Amino-7-(2-bromo-4-fluoro-phenyl)-7,8-dihydro-6I'-quinazolin-5-one oxime (Compound 25)

Stage 2: 2-Amino-7-(2-bromo-4-fluoro-phenyl)-7,8-dihydro-6H-quinazolin-5-one

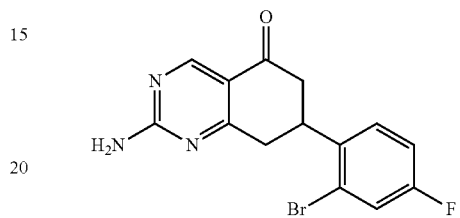

The title compound was prepared, following the procedure described for the synthesis of 2-amino-7-(4-chloro-phenyl)-7,8-dihydro-6H-quinazolin-5-one (example 2/a stage 2).

Mass spectrum (ES-MS (+ve)) 336/338 [MH]$^+$, Retention time 3.78 min, 96% UV.

1H NMR (250 MHz, CHLOROFORM-d) δ ppm 8.86 (1H, s), 7.30 (1H, dd), 7.14-7.23 (1H, m), 6.95-7.06 (1H, m), 5.50 (2H, br. s), 3.67-4.02 (1H, m), 2.46-3.21 (4H, m).

Stage 3

Method A—2-Amino-7-(2-bromo-4-fluoro-phenyl)-7,8-dihydro-6I'-quinazolin-5-one oxime (Compound 25)

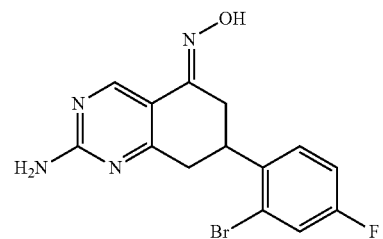 [SMILES: Nc1ncc2c(n1)CC(c1ccc(F)cc1Br)C/C2=N\O]

The title compound was prepared from 2-amino-7-(2-bromo-4-fluoro-phenyl)-7,8-dihydro-6H-quinazolin-5-one, from stage 2, following the procedure describing the synthesis of 2-amino-7-(4-chloro-phenyl)-7,8-dihydro-6H-quinazolin-5-one oxime (example 2/a stage 3—method A).

Mass spectrum (ES-MS (+ve)) 351 [MH]$^+$, Retention time 3.64 min, 100% UV.

1H NMR (360 MHz, DMSO-d$_6$) δ ppm 11.03 (1H, s), 8.73 (1H, s), 7.53-7.76 (2H, m), 7.24-7.44 (1H, m), 6.95 (2H, br. s), 3.40-3.52 (1H, m), 3.16-3.32 (1H, m), 3.04 (1H, dd), 2.70-2.83 (1H, m), 2.51-2.48 (1H, m).

j. 2-Amino-7-(aryl)-7,8-dihydro-6H-quinazolin-5-one oxime derivatives (Compounds 26 to 29)

The following compounds were also synthesized using a route equivalent to that described above with appropriately chosen starting materials:

2-Amino-7-(2,4-difluoro-phenyl)-7,8-dihydro-6H-quinazolin-5-one oxime (Compound 26)

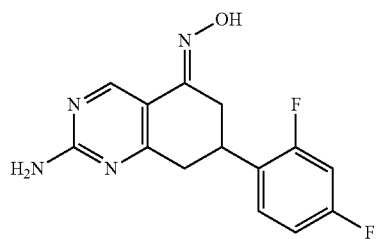 [SMILES: Nc1ncc2c(n1)CC(c1ccc(F)cc1F)C/C2=N\O]

Mass spectrum (ES-MS (+ve)) 291 [MH]$^+$, Retention time 1.68 min, 83% UV.
1H NMR (250 MHz, DMSO-d$_6$) δ ppm 10.98 (1H, s), 8.65 (1H, s), 7.41-7.50 (1H, m), 7.18-7.27 (1H, m), 7.04-7.12 (1H, m), 6.87 (2H, br. s), 3.26-3.29 (1H, m), 3.10-3.18 (1H, m), 2.91-3.03 (1H, m), 2.66-2.74 (1H, m), 2.53-2.58 (1H, m).

2-Amino-7-(2,6-dimethoxy-phenyl)-7,8-dihydro-6H-quinazolin-5-one oxime (Compound 27)

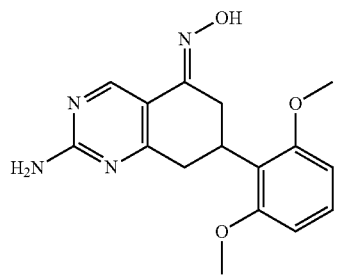 [SMILES: COc1cccc(OC)c1C1C/C(=N\O)c2cnc(N)nc2C1]

Mass spectrum (ES-MS (+ve)) 315 [MH]$^+$, Retention time 1.67 min, 92% UV.
1H NMR (250 MHz, DMSO-d$_6$) δ ppm 10.82 (1H, br. s), 8.62 (1H, s), 7.17 (1H, t), 6.63 (2H, d), 6.99 (2H, br. s), 3.72 (6H, s), 2.72-2.93 (3H, m), 2.22-2.37 (2H, m).

2-Amino-7-benzo[1,3]dioxol-4-yl-7,8-dihydro-6H-quinazolin-5-one oxime (Compound 28)

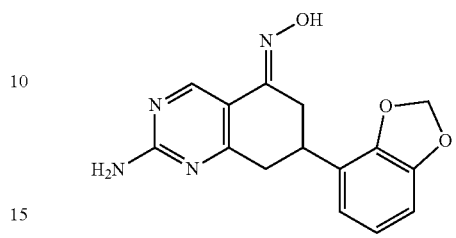

Mass spectrum (ES-MS (+ve)) 299 [MH]$^+$, Retention time 1.61 min, 96% UV.
1H NMR (360 MHz, DMSO-d$_6$) δ ppm 10.95 (1H, s), 8.64 (1H, s), 6.87 (2H, tr. s), 6.79-6.83 (3H, m), 6.01 (2H, br. s), 3.14-3.19 (2H, m), 2.95-3.02 (1H, m), 2.70-277 (1H, m), 2.53-2.61 (1H, m).

2-Amino-7-(2-morpholin-4-yl-phenyl)-7,8-dihydro-6H-quinazolin-5-one oxime (Compound 29)

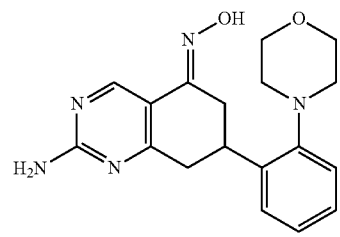 [SMILES: Nc1ncc2c(n1)CC(c1ccccc1N1CCOCC1)C/C2=N\O]

Mass spectrum (ES-MS (+ve)) 340 [MH]$^+$, Retention time 1.61 min, 92% UV.
1H NMR (250 MHz, DMSO-d$_6$) indicated the presence of two oxime stereoisomers in a 4:5 ratio δ ppm 11.76 (1H, (4:5), s), 10.94 (1H, (5:4), s), 8.72 (1H, s), 8.38 (1H (5:4), d), 7.86 (1H (4:5) d), 7.21-7.51 (3H, m), 6.93 (2H, br. s), 3.71 (4H, br. s), 3.56-3.62 (1H, m), 2.97-3.27 (3H, m), 2.84 (4H, br. s), 2.63-2.72 (1H, m).

General procedures for the Synthesis of 2-amino-4-methyl-7-phenyl-7,8-dihydro-6H-quinazolin-5-one oxime derivatives Scheme 3

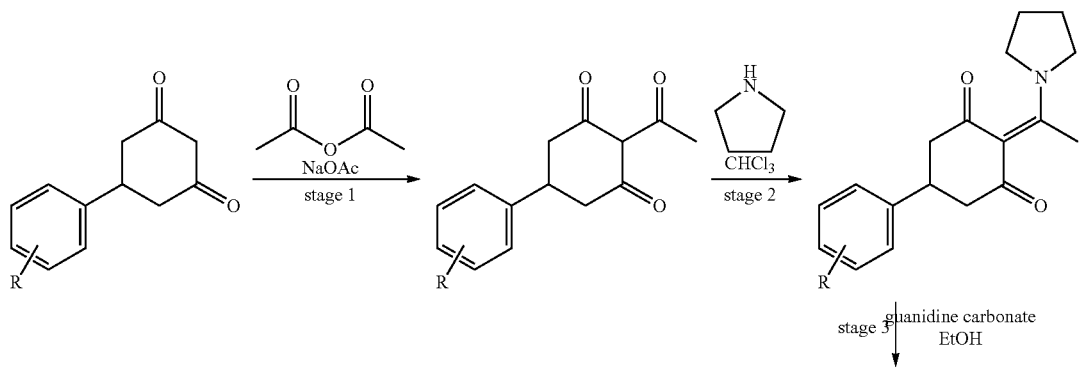

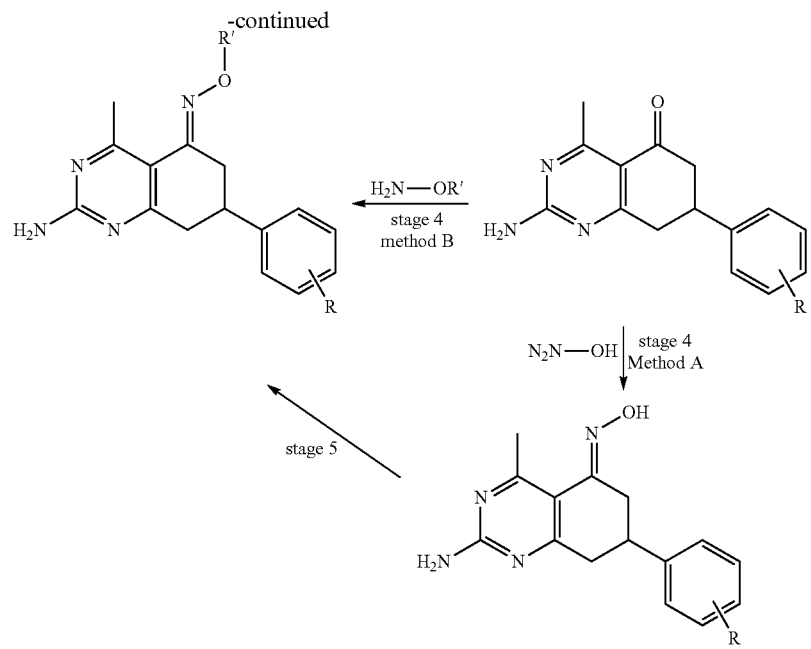

The stage 4 method A derivatives can be further alkylated with an R' group (stage 5).

EXAMPLE 3

Synthesis of compounds 2-amino-4-methyl-7-phenyl-7,8-dihydro-6H-quinazolin-5-one oxime derivatives using Scheme 3 a. 2-Amino-7-(4-fluoro-phenyl)-4-methyl-7,8-dihydro-6H-quinazolin-5-one oxime derivatives (Compounds 30, 31 and 32)

Stage 1:
2-Acetyl-5-(4-fluoro-phenyl)-cyclohexane-1,3-dione

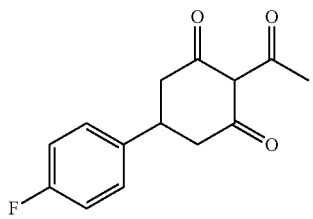 [SMILES: CC(=O)C1C(=O)CC(c2ccc(F)cc2)CC1=O]

5-(4-Fluorophenyl)cyclohexane-1,3-dione (500 mg, 2.4 mmol) and sodium acetate (200 mg, 2.4 mmol) were dissolved in acetic anhydride (5 ml) and heated in a sealed tube at 120° C. for 16 h. The reaction mixture was then allowed to cool to ambient temperature whereupon ethyl acetate (20 ml) and water (10 ml) were added. The organic phase was collected and washed 3 times with a saturated solution of sodium bicarbonate (3×15 ml). The organic phase was dried with MgSO$_4$ and filtered. The solvent was removed under reduced pressure. The title compound was purified by column chromatography using ethyl acetate/heptane (1/3) as the eluent.

Yield: 428 mg (66%)

1H NMR (enol isomer) (400 MHz, CHLOROFORM-d) δ ppm 7.14-7.24 (2H, m), 6.97-7.10 (2H, m), 3.27-3.42 (1H, m), 2.74-2.93 (3H, m), 2.68 (1H, d), 2.65 (3H, s).

Stage 2/3: 2-Amino-7-(4-fluoro-phenyl)-4-methyl-7,8-dihydro-6H-quinazolin-5-one

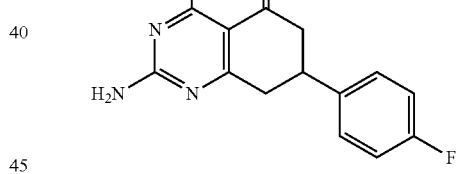

To a stirred solution of 2-acetyl-5-(4-fluoro-phenyl)-cyclohexane-1,3-dione (200 mg, 0.80 mmol) from stage 1, in chloroform was added pyrrolidine (68 mg, 0.96 mmol). The reaction mixture was stirred at ambient temperature and monitored by TLC until complete disappearance of 2-acetyl-5-(4-fluoro-phenyl)cyclohexane-1,3-dione. The reaction mixture was washed with water (10 ml) and the solvent was removed under reduced pressure to give a solid m=229 mg, mass spectrum (ES-MS (+ve)) 302 [MH]$^+$, Retention time 1.44 min, 100% UV. To a stirred solution of this solid (229 mg, 0.76 mmol) in dioxane (2.5 ml) was added guanidine carbonate (504 mg, 2.8 mmol) and the mixture heated at 100° C. and stirred for 16 h. 1,4-Dioxane was removed by evaporation under reduced pressure, water (5 ml) was added and the resulting precipitate was filtered, washed with water and heptane and air dried.

Yield: 105 mg (51%)

Mass spectrum (ES-MS (+ve)) 272 [MH]$^+$, Retention time 1.62 min, 89% UV

1H NMR (400 MHz, DMSO-d$_6$) δ ppm 7.45 (2H, s), 7.40 (2H, dd), 7.17 (2H, t), 3.38-3.48 (1H, m), 3.07-3.18 (1H, m), 2.81-2.91 (2H, m), 2.58-2.68 (1H, m), 2.56 (3H, s).

Stage 4

Method A—2-Amino-7-(4-fluoro-phenyl)-4-methyl-7,8-dihydro-6H-quinazolin-5-one oxime (Compound 30)

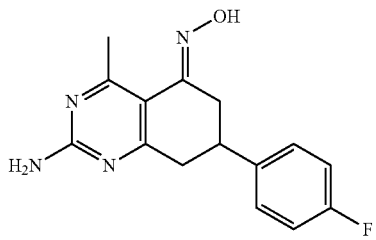

To a stirred solution of 2-amino-7-(4-fluoro-phenyl)-4-methyl-7,8-dihydro-6H-quinazolin-5-one (40 mg, 0.15 mmol) from stage 2/3, in pyridine (1 ml) at ambient temperature was added hydroxylamine hydrochloride (60 mg, 0.88 mmol). The reaction mixture was heated at 100° C. for 1 h. The reaction mixture was cooled to ambient temperature. Water (2 ml) was added and the resulting precipitate was filtered and washed with water (5 ml). The desired compound was dried under air suction followed by high vacuum.

Yield: 28 mg (65%)

Mass spectrum (ES-MS (+ve)) 287 [MH]$^+$, Retention time 3.28 min, 82% UV

1H NMR (400 MHz, DMSO-d$_6$) δ ppm 10.96 (1H, s), 7.38 (2H, dd), 7.14 (2H, t), 6.72 (2H, s), 2.85-3.24 (3H, m), 2.64-2.73 (1H, m), 2.52-2.58 (1H, m), 2.47 (3H, s).

Stage 4

Method B—2-Amino-7-(4-fluoro-phenyl)-4-methyl-7,8-dihydro-6H-quinazolin-5-one O-methyl-oxime (Compound 31)

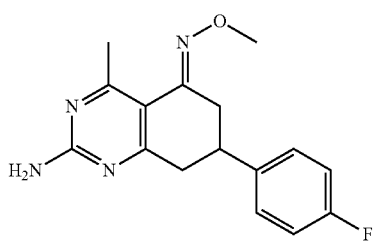

To a stirred solution of 2-amino-7-(4-fluoro-phenyl)-4-methyl-7,8-dihydro-6H-quinazolin-5-one (50 mg, 0.17 mmol) from stage 2/3, in pyridine (1 ml) at ambient temperature was added methoxylamine hydrochloride (60 mg, 0.72 mmol). The reaction mixture was heated at 100° C. for 1 h. The reaction mixture was cooled to ambient temperature. Water (2 ml) was added and the resulting precipitate was filtered and washed with water (5 ml). The desired compound was dried under air suction followed by high vacuum.

Yield: 26 mg (48%)

Mass spectrum (ES-MS (+ve)) 301 [MH]$^+$, Retention time 4.04 min, 85% UV

1H NMR (400 MHz, DMSO-d$_6$) δ ppm 7.38 (2H, dd), 7.15 (2H, t), 6.82 (2H, s), 3.86 (3H, s), 2.90-3.18 (3H, m), 2.65-2.73 (1H, m), 2.56-2.61 (1H, m), 2.52 (3H, s).

Stage 5: 2-Amino-7-(4-fluoro-phenyl)-4-methyl-7,8-dihydro-6H-quinazolin-5-one O-(2-dimethylamino-ethyl)-oxime (Compound 32)

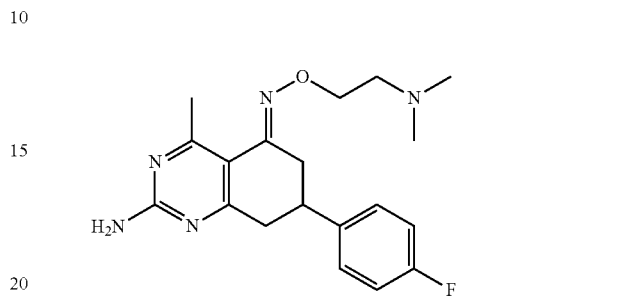

To a stirred solution of 2-amino-7-(4-fluoro-phenyl)-4-methyl-7,8-dihydro-6H-quinazolin-5-one oxime, compound 30, (109 mg, 0.38 mmol) in DMF (2 ml) under nitrogen was added sodium hydride (60% dispersion in oil) (18 mg, 0.44 mmol) and the mixture was stirred at ambient temperature for 10 min. 2-Dimethylaminoethylchloride hydrochloride (54 mg, 0.38 mmol) and triethylamine (52 μl, 0.38 mmol) were added to the reaction mixture, which was stirred and heated at 80° C. until complete disappearance of 2-amino-7-(4-fluoro-phenyl)-4-methyl-7,8-dihydro-6H-quinazolin-5-one oxime was observed by LC-MS. Ethyl acetate (5 ml) was added to the mixture and the solution was washed three times with water (3×5 ml). The organic phase was dried with MgSO$_4$, filtered and the solvent removed under reduced pressure to furnish the title compound as a brown solid.

Yield: 14 mg (10%)

Mass spectrum (ES-MS (+ve)) 358 [MH]$^+$, Retention time 2.84 min, 90% UV

1H NMR (400 MHz, MeOD-d$_4$) δ ppm 7.27-7.43 (2H, m), 7.01-7.15 (2H, m), 4.31 (2H, t), 3.34-3.40 (2H, m), 3.06-3.17 (1H, m), 2.85-3.02 (2H, m), 2.67-2.80 (2H, m), 2.65 (3H, s). 2.34 (6H, s).

b. 2-Amino-7-furan-2-yl-4-methyl-7,8-dihydro-6H-quinazolin-5-one oxime derivatives (Compounds 33, 34 and 35)

Stage 1:
2-Acetyl-5-furan-2-yl-cyclohexane-1,3-dione

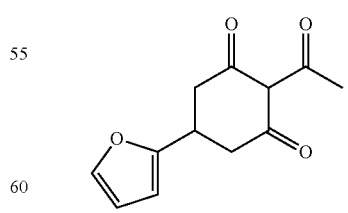

The title compound was prepared from 5-(2-furyl)-cyclohexane-1,3-dione (500 mg, 2.8 mmol) and sodium acetate (229 mg, 2.8 mmol), following the procedure describing the synthesis of 2-acetyl-5-(4-fluoro-phenyl)-cyclohexane-1,3-dione (example 3/a stage 1).

Yield: 321 mg (52%)

1H NMR (enol isomer) (400 MHz, CHLOROFORM-d) δ ppm 7.36 (1H, d), 6.32 (1H, dd), 6.09 (1H, d), 3.37-3.54 (1H, m), 2.78-3.08 (3H, m), 2.66-2.78 (1H, m), 2.63 (3H, s).

1H NMR (400 MHz, DMSO-d₆) δ ppm 11.03 (1H, s), 7.56 (1H, d), 6.72 (2H, s), 6.36 (1H, dd), 6.12 (1H, d), 3.12-3.24 (2H, m), 2.62-2.98 (3H, m), 2.48 (3H, s).

Stage 2/3: 2-Amino-7-furan-2-yl-4-methyl-7,8-dihydro-6H-quinazolin-5-one

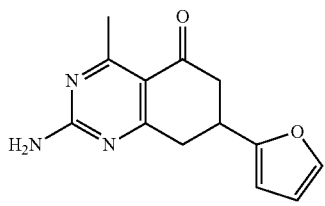 [SMILES: Cc1nc(N)nc2c1C(=O)CC(c1ccco1)C2]

The title compound was prepared from 2-acetyl-5-furan-2-yl-cyclohexane-1,3-dione (321 mg, 1.46 mmol), from stage 1, following the procedure describing the synthesis of 2-amino-7-(4-fluoro-phenyl)-4-methyl-7,8-dihydro-6H-quinazolin-5-one (example 3/a stage 2/3).

Yield: 340 mg (100%)

Mass spectrum (ES-MS (+ve)) 244 [MH]⁺, Retention time 1.40 min, 100% UV

Stage 4

Method A—2-Amino-7-furan-2-yl-4-methyl-7,8-dihydro-6H-quinazolin-5-one oxime (Compound 33)

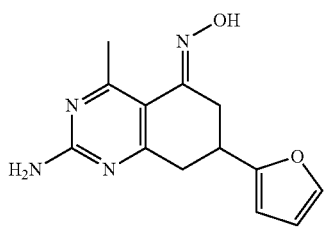 [SMILES: Cc1nc(N)nc2c1/C(=N/O)CC(c1ccco1)C2]

The title compound was prepared from 2-amino-7-furan-2-yl-4-methyl-7,8-dihydro-6H-quinazolin-5-one (27 mg, 0.11 mmol) from stage 2/3, following the procedure describing the synthesis of 2-amino-7-(4-fluoro-phenyl)-4-methyl-7,8-dihydro-6H-quinazolin-5-one oxime (example 3/a stage 4—method A).

Yield: 18 mg (63%)

Mass spectrum (ES-MS (+ve)) 258 [MH]⁺, Retention time 2.89 min, 82% UV

Stage 4

Method B—2-Amino-7-furan-2-yl-4-methyl-7,8-dihydro-6H-quinazolin-5-one O-methyl-oxime (Compound 34)

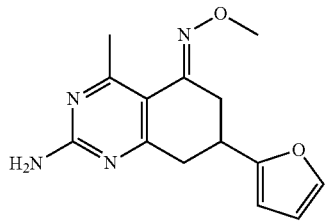 [SMILES: CO/N=C1\CC(c2ccco2)Cc2nc(N)nc(C)c21]

The title compound was prepared from 2-amino-7-furan-2-yl-4-methyl-7,8-dihydro-6H-quinazolin-5-one (27 mg, 0.11 mmol) from stage 2/3, following the procedure describing the synthesis of 2-amino-7-(4-fluoro-phenyl)-4-methyl-7,8-dihydro-6H-quinazolin-5-one O-methyl-oxime (example 3/a stage 4—method B).

Yield: 15 mg (50%)

Mass spectrum (ES-MS (+ve)) 273 [MH]⁺, Retention time 3.69 min, 88% UV

1H NMR (400 MHz, DMSO-d₆) δ ppm 7.56 (1H, d), 6.81 (2H, s), 6.36 (1H, dd), 6.12 (1H, d), 3.90 (3H, s), 3.11-3.24 (2H, m), 2.64-2.94 (3H, m), 2.50 (3H, s).

Stage 5: 2-Amino-7-furan-2-yl-4-methyl-7,8-dihydro-6H-quinazolin-5-one O-(2-dimethylamino-ethyl)-oxime (Compound 35)

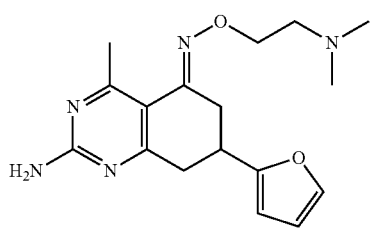 [SMILES: Cc1nc(N)nc2c1/C(=N/OCCN(C)C)CC(c1ccco1)C2]

The title compound was prepared from 2-amino-7-furan-2-yl-4-methyl-7,8-dihydro-6H-quinazolin-5-one oxime (compound 33), following the procedure describing the synthesis of 2-amino-7-(4-fluoro-phenyl)-4-methyl-7,8-dihydro-6H-quinazolin-5-one O-(2-dimethylamino-ethyl)-oxime (example 3/a stage 5).

Mass spectrum (ES-MS (+ve)) 330 [MH]⁺, Retention time 1.11 min, 90% UV

1H NMR (400 MHz, MeOD-d₄) δ ppm 7.43 (1H, d), 6.31-6.37 (1H, m), 6.16 (1H, d), 4.55 (2H, t), 3.56 (2H, t), 3.34-3.40 (2H, m), 3.02-3.19 (3H, m), 2.97 (6H, s), 2.74 (3H, s).

c. 2-Amino-4-methyl-7-phenyl-7,8-dihydro-6H-quinazolin-5-one oxime and 2-amino-4-methyl-7-phenyl-7,8-dihydro-6H-quinazolin-5-one O-methyl-oxime (Compounds 36 and 37)

Stage 4

Method A—2-Amino-4-methyl-7-phenyl-7,8-dihydro-6H-quinazolin-5-one oxime (Compound 36)

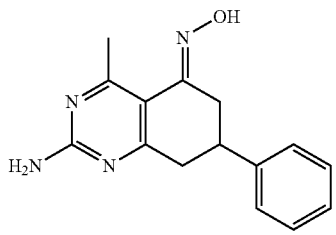 [SMILES: Cc1nc(N)nc2c1/C(=N/O)CC(c1ccccc1)C2]

The title compound was prepared from commercially available 2-amino-4-methyl-7-phenyl-7,8-dihydro-6H-quinazolin-5-one (60 mg, 0.23 mmol), following the procedure describing the synthesis of 2-amino-7-(4-fluoro-phenyl)-4-methyl-7,8-dihydro-6H-quinazolin-5-one oxime (example 3/a stage 4—method A).

Yield: 5 mg (8%)

Mass spectrum (ES-MS (+ve)) 269 [MH]⁺, Retention time 3.18 min, 87% UV

1H NMR (360 MHz, DMSO-d₆) δ ppm 10.94 (1H, s), 7.12-7.51 (5H, m), 6.70 (2H, s), 3.11-3.27 (1H, m), 2.87-3.05 (2H, m), 2.70 (1H, d), 2.54-2.61 (1H, m), 2.51 (3H, br. s).

Stage 4

Method B—2-Amino-4-methyl-7-phenyl-7,8-dihydro-6H-quinazolin-5-one O-methyl-oxime (Compound 37)

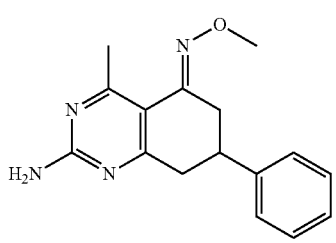 [SMILES: CO/N=C1\CC(c2ccccc2)Cc2nc(N)nc(C)c21]

The title compound was prepared from commercially available 2-amino-4-methyl-7-phenyl-7,8-dihydro-6H-quinazolin-5-one (40 mg, 0.15 mmol), following the procedure describing the synthesis of 2-amino-7-(4-fluoro-phenyl)-4-methyl-7,8-dihydro-6H-quinazolin-5-one O-methyl-oxime (example 3/a stage 4—method B).

Yield: 40 mg (94%)

Mass spectrum (ES-MS (+ve)) 283 [MH]⁺, Retention time 3.95 min, 91% UV

1H NMR (400 MHz, DMSO-d₆) δ ppm 6.98-7.48 (5H, m), 3.89 (3H, s), 2.96-3.22 (3H, m), 2.71-2.84 (1H, m), 2.54-2.66 (4H, m).

d. 2-Amino-7-thien-2-yl-4-methyl-7,8-dihydro-6H-quinazolin-5-one oxime and 2-amino-7-thien-2-yl-4-methyl-7,8-dihydro-6H-quinazolin-5-one O-methyl-oxime (Compounds 38 and 39)

Stage 1:
2-Acetyl-5-thien-2-yl-cyclohexane-1,3-dione

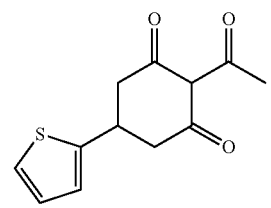 [SMILES: CC(=O)C1C(=O)CC(c2cccs2)CC1=O]

The title compound was prepared from 5-thien-2-yl-cyclohexane-1,3-dione (600 mg, 3.09 mmol) and sodium acetate (253 mg, 3.09 mmol), following the procedure describing the synthesis of 2-acetyl-5-(4-fluoro-phenyl)-cyclohexane-1,3-dione (example 3/a stage 1).

Yield: 430 mg (58%)

Mass spectrum (ES-MS (+ve)) 237 [MH]⁺, Retention time 1.94 min, 100% UV

Stage 2/3: 2-Amino-7-thien-2-yl-4-methyl-7,8-dihydro-6H-quinazolin-5-one

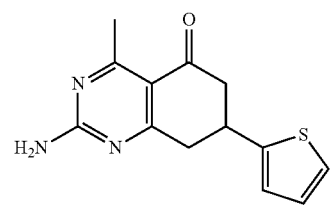

The title compound was prepared from 2-acetyl-5-thien-2-yl-cyclohexane-1,3-dione (430 mg, 1.82 mmol), from stage 1, following the procedure describing the synthesis of 2-amino-7-(4-fluoro-phenyl)-4-methyl-7,8-dihydro-6H-quinazolin-5-one.

Yield: 240 mg (51%)

Mass spectrum (ES-MS (+ve)) 260 [MH]⁺, Retention time 3.52 min, 82% UV

1H NMR (400 MHz, DMSO-d$_6$) δ ppm 7.38 (1H, dd), 6.90-7.09 (2H, m), 3.63-3.84 (1H, m), 2.99-3.20 (2H, m), 2.69-2.92 (2H, m), 2.53 (3H, s).

Stage 4

Method A—2-Amino-7-thien-2-yl-4-methyl-7,8-dihydro-6H-quinazolin-5-one oxime (Compound 38)

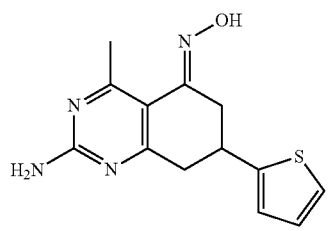

The title compound was prepared from 2-amino-7-thien-2-yl-4-methyl-7,8-dihydro-6H-quinazolin-5-one (50 mg, 0.19 mmol), from stage 2/3, following the procedure describing the synthesis of 2-amino-7-(4-fluoro-phenyl)-4-methyl-7,8-dihydro-6H-quinazolin-5-one oxime (example 3/a stage 4—method A).

Yield: 32 mg (62%)

Mass spectrum (ES-MS (+ve)) 274 [MH]$^+$, Retention time 3.12 min, 94% UV

1H NMR (400 MHz, DMSO-d$_6$) δ ppm 11.03 (1H, s), 7.36 (1H, d), 6.89-7.13 (2H, m), 6.73 (2H, s), 3.36-3.47 (1H, m), 3.24 (1H, dd), 2.78-2.98 (2H, m), 2.69 (1H, dd), 2.49 (3H, s)

Stage 4

Method B—2-Amino-7-thien-2-yl-4-methyl-7,8-dihydro-6H-quinazolin-5-one O-methyl-oxime (Compound 39)

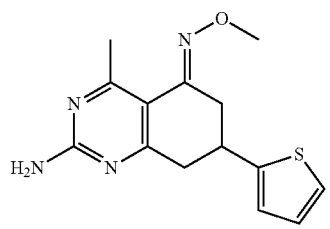

The title compound was prepared from 2-amino-7-thien-2-yl-4-methyl-7,8-dihydro-6H-quinazolin-5-one (50 mg, 0.19 mmol), from stage 2/3, following the procedure describing the synthesis of 2-amino-7-(4-fluoro-phenyl)-4-methyl-7,8-dihydro-6H-quinazolin-5-one O-methyl-oxime (example 3/a stage 4—method B) except that the title compound was purified by column chromatography eluting with ethyl acetate/heptane (1/1).

Yield: 15 mg (27%)

Mass spectrum (ES-MS (+ve)) 289 [MH]$^+$, Retention time 3.93 min, 94% UV

1H NMR (400 MHz, MeOD-d$_4$) δ ppm 7.24 (1H, d), 6.77-7.00 (2H, m), 3.95 (3H, s), 3.39-3.47 (1H, m), 3.34 (1H, d), 2.99-3.07 (1H, m), 2.86-2.96 (1H, m), 2.78 (1H, dd), 2.60 (3H, s).

e. 2-Amino-4-methyl-7-p-tolyl-7,8-dihydro-6H-quinazolin-5-one oxime and 2-amino-4-methyl-7-p-tolyl-7,8-dihydro-6H-quinazolin-5-one O-methyl-oxime (Compounds 40 and 41)

Stage 1: 2-Acetyl-5-p-tolyl-cyclohexane-1,3-dione

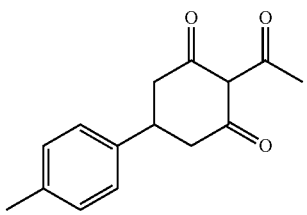 [SMILES: CC(=O)C1C(=O)CC(c2ccc(C)cc2)CC1=O]

The title compound was prepared from 5-p-tolyl-cyclohexane-1,3-dione (1.6 g, 5.74 mmol), from example 1/c stage 2, and sodium acetate (470 mg, 5.74 mmol), following the procedure describing the synthesis of 2-acetyl-5-(4-fluoro-phenyl)-cyclohexane-1,3-dione (example 3/a stage 1).

Yield: 850 mg (60%)

Mass spectrum (ES-MS (+ve)) 245 [MH]$^+$, Retention time 2.22 min, 100% UV

Stage 2/3: 2-Amino-4-methyl-7-p-tolyl-7,8-dihydro-6H-quinazolin-5-one

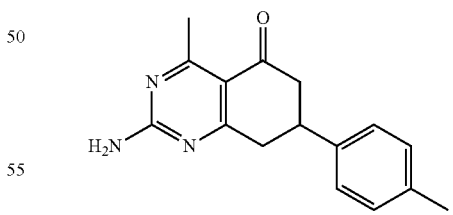

The title compound was prepared from 2-acetyl-5-p-tolyl-cyclohexane-1,3-dione (850 mg, 3.50 mmol), stage 1, following the procedure describing the synthesis of 2-amino-7-(4-fluoro-phenyl)-4-methyl-7,8-dihydro-6H-quinazolin-5-one (example 3/a stage 2/3).

Yield: 750 mg (80%)

Mass spectrum (ES-MS (+ve)) 268 [MH]$^+$, Retention time 3.90 min, 100% UV

1H NMR (360 MHz, DMSO-d$_6$) δ ppm 7.42 (2H, br. s), 7.19-7.25 (2H, m), 7.08-7.16 (2H, m), 3.35-3.41 (1H, m), 3.04-3.15 (1H, m), 2.77-2.91 (2H, m), 2.53-2.64 (4H, m), 2.28 (3H, s).

Stage 4

Method A—2-Amino-4-methyl-7-p-tolyl-7,8-dihydro-6H-quinazolin-5-one oxime (Compound 40)

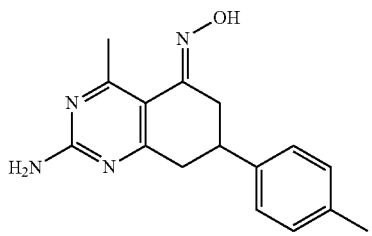 [SMILES: Cc1ccc(C2C/C(=N\O)c3c(C)nc(N)nc3C2)cc1]

The title compound was prepared from 2-amino-4-methyl-7-p-tolyl-7,8-dihydro-6H-quinazolin-5-one (50 mg, 0.19 mmol), from stage 2/3, following the procedure describing the synthesis of 2-amino-7-(4-fluoro-phenyl)-4-methyl-7,8-dihydro-6H-quinazolin-5-one oxime (example 3/a stage 4—method A).

Yield: 14 mg (26%)

*Note—LC-MS proved unreliable for purity determination for this oxime due to hydrolysis to ketone derivative.

1H NMR (250 MHz, DMSO-d$_6$) δ ppm 10.93 (1H, s), 7.00-7.34 (4H, m), 6.69 (2H, s), 3.09-3.21 (1H, m), 2.81-3.04 (2H, m), 2.59-2.75 (2H, m), 2.51 (3H, s), 2.27 (3H, s).

Stage 4

Method B—2-Amino-4-methyl-7-p-tolyl-7,8-dihydro-6H-quinazolin-5-one O-methyl-oxime (Compound 41)

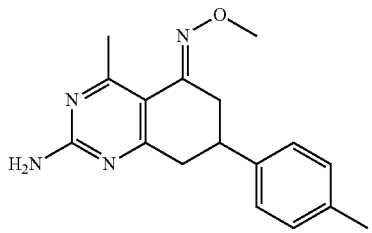 [SMILES: CO/N=C1\CC(c2ccc(C)cc2)Cc2nc(N)nc(C)c21]

The title compound was prepared from 2-amino-4-methyl-7-p-tolyl-7,8-dihydro-6H-quinazolin-5-one (50 mg, 0.19 mmol), stage 2/3, following the procedure describing the synthesis of 2-amino-7-(4-fluoro-phenyl)-4-methyl-7,8-dihydro-6H-quinazolin-5-one O-methyl-oxime (example 3/a stage 4—method B).

Yield: 25 mg (44%)

*Note—LC-MS proved unreliable for purity determination for this oxime due to hydrolysis to ketone derivative.

1H NMR (400 MHz, DMSO-d$_6$) δ ppm 7.18-7.25 (2H, m), 7.04-7.17 (2H, m), 6.80 (2H, s), 3.87 (3H, s), 3.06-3.17 (1H, m), 2.83-3.02 (2H, m), 2.54-2.71 (2H, m), 2.52 (3H, s), 2.27 (3H, s).

f. 2-Amino-7-(2-methoxy-phenyl)-4-methyl-7,8-dihydro-6H-quinazolin-5-one oxime and 2-amino-7-(2-methoxy-phenyl)-4-methyl-7,8-dihydro-6H-quinazolin-5-one O-methyl-oxime (Compounds 42 and 43)

Stage 1: 2-Acetyl-5-(2-methoxy-phenyl)-cyclohexane-1,3-dione

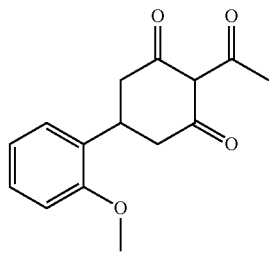 [SMILES: COc1ccccc1C1CC(=O)C(C(C)=O)C(=O)C1]

The title compound was prepared from 5-(2-methoxy-phenyl)-cyclohexane-1,3-dione (1.0 g, 4.58 mmol), example 1/a, and sodium acetate (376 mg, 4.58 mmol), following the procedure describing the synthesis of 2-acetyl-5-(4-fluoro-phenyl)-cyclohexane-1,3-dione (example 3/a stage 1).

Yield: 872 mg (72%)

Mass spectrum (ES-MS (+ve)) 261 [MH]$^+$, Retention time 2.09 min, 100% UV

Stage 2/3: 2-Amino-7-(2-methoxy-phenyl)-4-methyl-7,8-dihydro-6H-quinazolin-5-one

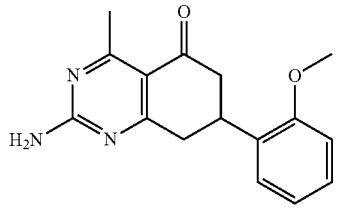 [SMILES: COc1ccccc1C1CC(=O)c2c(C)nc(N)nc2C1]

The title compound was prepared from 2-acetyl-5-(2-methoxy-phenyl)-cyclohexane-1,3-dione (872 mg, 3.35 mmol), from stage 1, following the procedure describing the synthesis of 2-amino-7-(4-fluoro-phenyl)-4-methyl-7,8-dihydro-6H-quinazolin-5-one (example 3/a stage 2/3) except that the title compound was further purified by recrystallisation in methanol.

Yield: 170 mg (18%)

Mass spectrum (ES-MS (+ve)) 284 [MH]$^+$, Retention time 3.78 min, 100% UV

1H NMR (400 MHz, DMSO-d$_6$) δ ppm 7.43 (2H, s), 7.19-7.28 (2H, m), 7.01 (1H, d), 6.94 (1H, t), 3.80 (3H, s), 3.56-3.72 (1H, m), 3.08 (1H, dd), 2.77-2.92 (2H, m), 2.54-2.66 (4H, m).

Stage 4

Method A—2-Amino-7-(2-methoxy-phenyl)-4-methyl-7,8-dihydro-6H-quinazolin-5-one oxime (Compound 42)

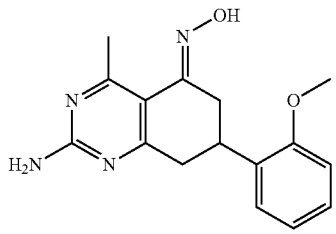

The title compound was prepared from 2-amino-7-(2-methoxy-phenyl)-4-methyl-7,8-dihydro-6H-quinazolin-5-one (50 mg, 0.17 mmol), stage 2/3, following the procedure describing the synthesis of 2-amino-7-(4-fluoro-phenyl)-4-methyl-7,8-dihydro-6H-quinazolin-5-one oxime (example 3/a stage 4—method A).

Yield: 40 mg (79%)

Mass spectrum (ES-MS (+ve)) 299 [MH]$^+$, Retention time 3.28 min, 89% UV

1H NMR (400 MHz, DMSO-d$_6$) δ ppm 10.93 (1H, s), 7.16-7.30 (2H, m), 6.85-7.04 (2H, m), 6.71 (2H, s), 3.79 (3H, s), 3.21-3.30 (1H, m), 3.14 (1H, dd), 2.91 (1H, dd), 2.60-2.71 (1H, m), 2.52-2.58 (4H, m).

Stage 4

Method B—2-Amino-7-(2-methoxy-phenyl)-4-methyl-7,8-dihydro-6H-quinazolin-5-one O-methyl-oxime (Compound 43)

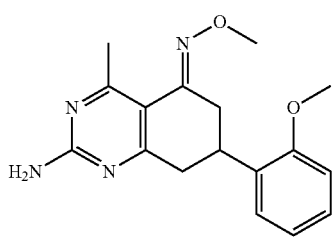

The title compound was prepared from 2-amino-7-(2-methoxy-phenyl)-4-methyl-7,8-dihydro-6H-quinazolin-5-one (50 mg, 0.19 mmol), stage 2/3, following the procedure describing the synthesis of 2-amino-7-(4-fluoro-phenyl)-4-methyl-7,8-dihydro-6H-quinazolin-5-one O-methyl-oxime (example 3/a stage 4—method B).

Yield: 50 mg (84%)

Mass spectrum (ES-MS (+ve)) 312 [MH]$^+$, Retention time 4.04 min, 92% UV

1H NMR (400 MHz, DMSO-d$_6$) δ ppm 7.19-7.28 (2H, m), 6.99 (1H, d), 6.93 (1H, t), 6.80 (2H, s), 3.85 (3H, s), 3.78 (3H, s), 3.26-3.32 (1H, m), 3.10 (1H, d), 2.93 (1H, dd), 2.51-2.69 (5H, m).

g. 2-Amino-7-(3-fluoro-phenyl)-4-methyl-7,8-dihydro-6H-quinazolin-5-one oxime and 2-amino-7-(3-fluoro-phenyl)-4-methyl-7,8-dihydro-6H-quinazolin-5-one O-methyl-oxime (Compounds 44 and 45)

Stage 1:
2-Acetyl-5-(3-fluoro-phenyl)-cyclohexane-1,3-dione

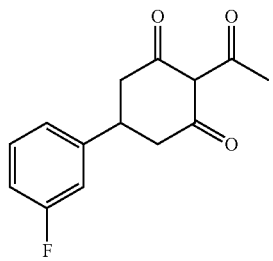 [SMILES: CC(=O)C1C(=O)CC(c2cccc(F)c2)CC1=O]

The title compound was prepared from 5-(3-fluoro-phenyl)-cyclohexane-1,3-dione (500 mg, 2.48 mmol), example 1/d stage 2, and sodium acetate (204 mg, 2.48 mmol), following the procedure describing the synthesis of 2-acetyl-5-(4-fluoro-phenyl)-cyclohexane-1,3-dione (example 3/a stage 1).

Yield: 100 mg (16%)

Mass spectrum (ES-MS (+ve)) 249 [MH]$^+$, Retention time 2.03 min, 97% UV

Stage 2/3 2-Amino-7-(3-fluoro-phenyl)-4-methyl-7,8-dihydro-6H-quinazolin-5-one

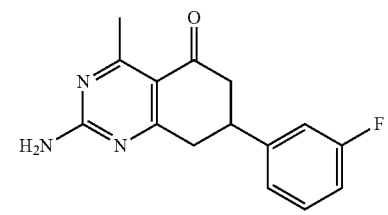 [SMILES: Cc1nc(N)nc2c1C(=O)CC(c1cccc(F)c1)C2]

The title compound was prepared from 2-acetyl-5-(3-fluoro-phenyl)-cyclohexane-1,3-dione (100 mg, 0.42 mmol), from stage 1, following the procedure describing the synthesis of 2-amino-7-(4-fluoro-phenyl)-4-methyl-7,8-dihydro-6H-quinazolin-5-one (example 3/a stage 2/3) except that the title compound was further purified by recrystallisation in methanol.

Yield: 77 mg (18%)

Mass spectrum (ES-MS (+ve)) 272 [MH]$^+$, Retention time 3.76 min, 96% UV

1H NMR (400 MHz, DMSO-d$_6$) δ ppm 7.46 (2H, br. s), 7.34-7.42 (1H, m), 7.17-7.26 (2H, m), 7.07 (1H, t), 3.40-3.50 (1H, m), 3.14 (1H, dd), 2.82-2.95 (2H, m), 2.62 (1H, d), 2.56 (3H, s).

Stage 4

Method A—2-Amino-7-(3-fluoro-phenyl)-4-methyl-7,8-dihydro-6H-quinazolin-5-one oxime (Compound 44)

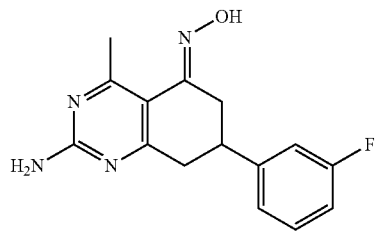 [SMILES: Cc1nc(N)nc2c1/C(=N/O)CC(c1cccc(F)c1)C2]

The title compound was prepared from 2-amino-7-(3-fluoro-phenyl)-4-methyl-7,8-dihydro-6H-quinazolin-5-one (30 mg, 0.11 mmol), stage 2/3, following the procedure describing the synthesis of 2-amino-7-(4-fluoro-phenyl)-4-methyl-7,8-dihydro-6H-quinazolin-5-one oxime (example 3/a stage 4).

Yield: 5 mg (16%)

Mass spectrum (ES-MS (+ve)) 286 [MH]$^+$, Retention time 3.32 min, 92% UV

1H NMR (400 MHz, DMSO-d$_6$) δ ppm 10.98 (1H, s), 7.30-7.48 (1H, m), 7.17-7.25 (2H, m), 7.02-7.10 (1H, m), 6.73 (2H, s), 3.17 (1H, d), 2.91-3.11 (2H, m), 2.70 (1H, d), 2.54-2.62 (1H, m), 2.53 (3H, s).

Stage 4

Method B—2-Amino-7-(3-fluoro-phenyl)-4-methyl-7,8-dihydro-6H-quinazolin-5-one O-methyl-oxime (Compound 45)

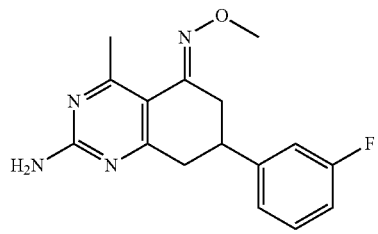 [SMILES: CO/N=C1\CC(c2cccc(F)c2)Cc2nc(N)nc(C)c21]

The title compound was prepared from 2-amino-7-(3-fluoro-phenyl)-4-methyl-7,8-dihydro-6H-quinazolin-5-one (30 mg, 0.11 mmol), from stage 2/3, following the procedure describing the synthesis of 2-amino-7-(4-fluoro-phenyl)-4-methyl-7,8-dihydro-6H-quinazolin-5-one O-methyl-oxime (example 3/a stage 4).

Yield: 3 mg (9%)

Mass spectrum (ES-MS (+ve)) 301 [MH]$^+$, Retention time 4.09 min, 93% UV

1H NMR (400 MHz, MeOD-d$_4$) δ ppm 7.29-7.39 (1H, m), 7.04-7.15 (2H, m), 6.97 (1 H, t), 3.94 (3H, s), 3.25 (1H, dd), 3.04-3.13 (1H, m), 2.81-3.00 (2H, m), 2.54-2.71 (4H, m).

h. 2-Amino-7-(2-fluoro-phenyl)-4-methyl-7,8-dihydro-6H-quinazolin-5-one oxime and 2-amino-7-(2-fluoro-phenyl)-4-methyl-7,8-dihydro-6H-quinazolin-5-one O-methyl-oxime (Compounds 46 and 47)

Stage 1:
2-Acetyl-5-(2-fluoro-phenyl)-cyclohexane-1,3-dione

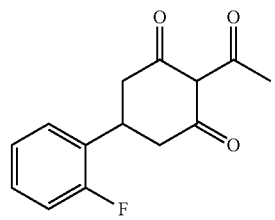 [SMILES: CC(=O)C1C(=O)CC(c2ccccc2F)CC1=O]

The title compound was prepared from 5-(2-fluoro-phenyl)-cyclohexane-1,3-dione (770 mg, 3.74 mmol), example 1/b stage 2, and sodium acetate (307 mg, 3.74 mmol), following the procedure describing the synthesis of 2-acetyl-5-(4-fluoro-phenyl)-cyclohexane-1,3 dione (example 3/a stage 1).

Yield: 200 mg (22%)

Mass spectrum (ES-MS (+ve)) 249 [MH]$^+$, Retention time 2.04 min, 90% UV

Stage 2/3: 2-Amino-7-(2-fluoro-phenyl)-4-methyl-7,8-dihydro-6H-quinazolin-5-one

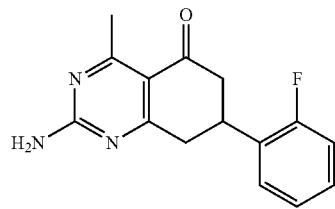 [SMILES: Cc1nc(N)nc2c1C(=O)CC(c1ccccc1F)C2]

The title compound was prepared from 2-acetyl-5-(2-fluoro-phenyl)-cyclohexane-1,3-dione (200 mg, 0.81 mmol), from stage 1, following the procedure describing the synthesis of 2-amino-7-(4-fluoro-phenyl)-4-methyl-7,8-dihydro-6H-quinazolin-5-one (example 3/a stage 2/3) except that the title compound was further purified by recrystallisation in methanol.

Yield: 140 mg (64%)

Mass spectrum (ES-MS (+ve)) 272 [MH]$^+$, Retention time 3.74 min, 93% UV

1H NMR (400 MHz, DMSO-d$_6$) δ ppm 7.36-7.56 (3H, m), 7.27-7.35 (1H, m), 7.10-7.23 (2H, m), 3.66 (1H, t), 3.15 (1H, dd), 2.77-2.96 (2H, m), 2.63 (1H, d), 2.56 (3H, s).

Stage 4

Method A—2-Amino-7-(2-fluoro-phenyl)-4-methyl-7,8-dihydro-6H-quinazolin-5-one oxime (Compound 46)

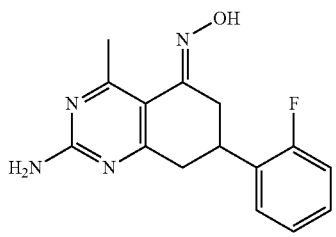 [SMILES: Cc1nc(N)nc2c1/C(=N/O)CC(c1ccccc1F)C2]

The title compound was prepared from 2-amino-7-(2-fluoro-phenyl)-4-methyl-7,8-dihydro-6H-quinazolin-5-one (50 mg, 0.18 mmol), stage 2/3, following the procedure describing the synthesis of 2-amino-7-(4-fluoro-phenyl)-4-methyl-7,8-dihydro-6H-quinazolin-5-one oxime.

Yield: 33 mg (64%)

*Note—LC-MS proved unreliable for purity determination for this oxime due to hydrolysis to the ketone derivative.

1H NMR (400 MHz, DMSO-d$_6$) δ ppm 11.01 (1H, s), 7.40 (1H, t), 7.25-7.35 (1H, m), 7.13-7.23 (2H, m), 6.73 (2H, s), 3.24-3.30 (1H, m), 3.12-3.23 (1H, m), 2.97 (1H, dd), 2.54-2.76 (2H, m), 2.52 (3H, s).

Stage 4

Method B—2-Amino-7-(2-fluoro-phenyl)-4-methyl-7,8-dihydro-6H-quinazolin-5-one O-methyl-oxime (Compound 47)

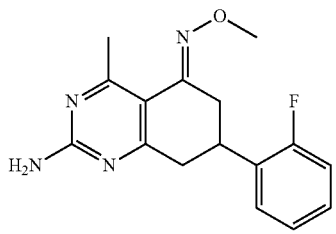 [SMILES: CO/N=C1\CC(c2ccccc2F)Cc2nc(N)nc(C)c21]

The title compound was prepared from 2-amino-7-(2-fluoro-phenyl)-4-methyl-7,8-dihydro-6H-quinazolin-5-one (50 mg, 0.18 mmol), from stage 2/3, following the procedure describing the synthesis of 2-amino-7-(4-fluoro-phenyl)-4-methyl-7,8-dihydro-6H-quinazolin-5-one O-methyl-oxime (example 3/a stage 4—method B).

Yield: 22 mg (41%)

Mass spectrum (ES-MS (+ve)) 301 [MH]$^+$, Retention time 4.08 min, 85% UV

1H NMR (400 MHz, DMSO-d$_6$) δ ppm 7.39 (1H, t), 7.25-7.35 (1H, m), 7.14-7.23 (2H, m), 6.83 (2H, s), 3.86 (3H, s), 3.24-3.31 (1H, m), 3.10-3.20 (1H, m), 2.98 (1H, dd), 2.58-2.76 (2H, m), 2.52 (3H, s).

i. 2-Amino-7-(2-bromo-phenyl'-4-methyl-7,8-dihydro-6H-quinazolin-5-one oxime (Compound 48)

Stage 2/3: 2-Amino-7-(2-bromo-phenyl)-4-methyl-7,8-dihydro-6H-quinazolin-5-one

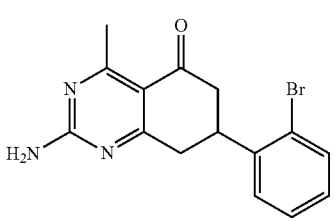 [SMILES: Cc1nc(N)nc2c1C(=O)CC(c1ccccc1Br)C2]

The title compound was prepared from 2-acetyl-5-(2-bromo-phenyl)-cyclohexane-1,3-dione, following the procedure describing the synthesis of 2-amino-7-(4-fluoro-phenyl)-4-methyl-7,8-dihydro-6H-quinazolin-5-one (example 3/a stage 2/3).

Mass spectrum (ES-MS (+ve)) 332/334 [MH]$^+$, Retention time 3.86 min, 91% UV.

1H NMR (360 MHz, DMSO-d$_6$) δ ppm 7.65 (1H, d), 7.48 (2H, br. s), 7.42 (2H, t), 7.22 (1H, t), 3.70 (1H, t), 3.04-3.23 (1H, m), 2.80-2.99 (2H, m), 2.66 (1H, br. s), 2.57 (3H, s).

Stage 4

Method A—2-Amino-7-(2-bromo-phenyl)-4-methyl-7,8-dihydro-6H-quinazolin-5-one oxime (Compound 48)

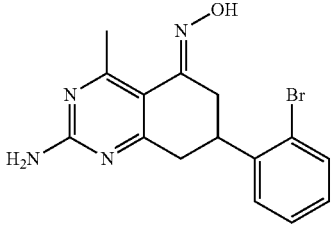 [SMILES: Cc1nc(N)nc2c1/C(=N/O)CC(c1ccccc1Br)C2]

The title compound was prepared from 2-amino-7-(2-bromo-phenyl)-4-methyl-7,8-dihydro-6H-quinazolin-5-one, stage 2/3, following the procedure describing the synthesis of 2-amino-7-(4-fluoro-phenyl)-4-methyl-7,8-dihydro-6H-quinazolin-5-one oxime (example 3/a stage 4—method A).

Mass spectrum (ES-MS (+ve)) 347 [MH]$^+$, Retention time 3.37 min, 91% UV.

1H NMR (250 MHz, DMSO-d$_6$) δ ppm 11.01 (1H, s), 7.61 (1H, d), 7.43-7.51 (1H, m), 7.39 (1H, t), 7.19 (1H, t), 6.74

(2H, br. s), 3.15-3.29 (2H, m), 2.90-3.05 (1H, m), 2.63-2.76 (1H, m), 2.53-2.62 (1H, m), 2.51 (3H, s).

j. 2-Amino-7-(2,6-dimethoxy-phenyl)-4-methyl-7,8-dihydro-6H-quinazolin-5-one oxime and 2-amino-7-benzo[1,3]dioxol-4-yl-4-methyl-7,8-dihydro-6H-quinazolin-5-one oxime (Compounds 49 and 50)

The following compounds were also synthesized using a route equivalent to that described above with appropriately chosen starting materials:

2-Amino-7-(2,6-dimethoxy-phenyl)-4-methyl-7,8-dihydro-6H-quinazolin-5-one oxime (Compound 49)

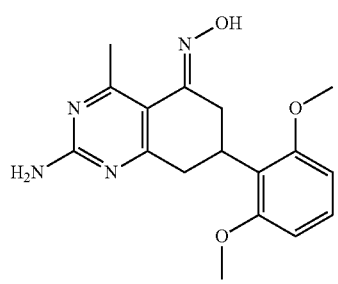 [SMILES: COc1cccc(OC)c1C1C/C(=N\O)c2c(C)nc(N)nc2C1]

Mass spectrum (ES-MS (+ve)) 329 [MH]+, Retention time 1.54 min, 94% UV.

1H NMR (360 MHz, DMSO-d6) δ ppm 11.13 (1H, br. s), 7.44 (2H, br. s), 7.21 (1H, t), 6.68 (2H, d), 3.75 (6H, s), 2.86-3.01 (2H, m), 2.56-2.68 (3H, m).

2-Amino-7-benzo[1,3]dioxol-4-yl-4-methyl-7,8-dihydro-6H-quinazolin-5-one oxime (Compound 50)

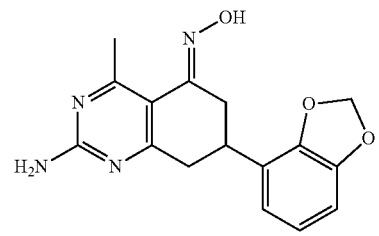

Mass spectrum (ES-MS (+ve)) 313 [MH]+, Retention time 1.55 min, 86% UV.

1H NMR (360 MHz, DMSO-d6) δ ppm 10.99 (1H, s), 6.79 (2H, br. s), 6.71 (1H, br. s), 6.00 (2H, br. s), 2.88-3.22 (3H, m), 2.60-2.81 (2H, m), 2.48 (3H, s).

General procedures for the Synthesis of 2-amino-7-biaryl-6H-quinazolin-5-one oxime derivatives Scheme 4

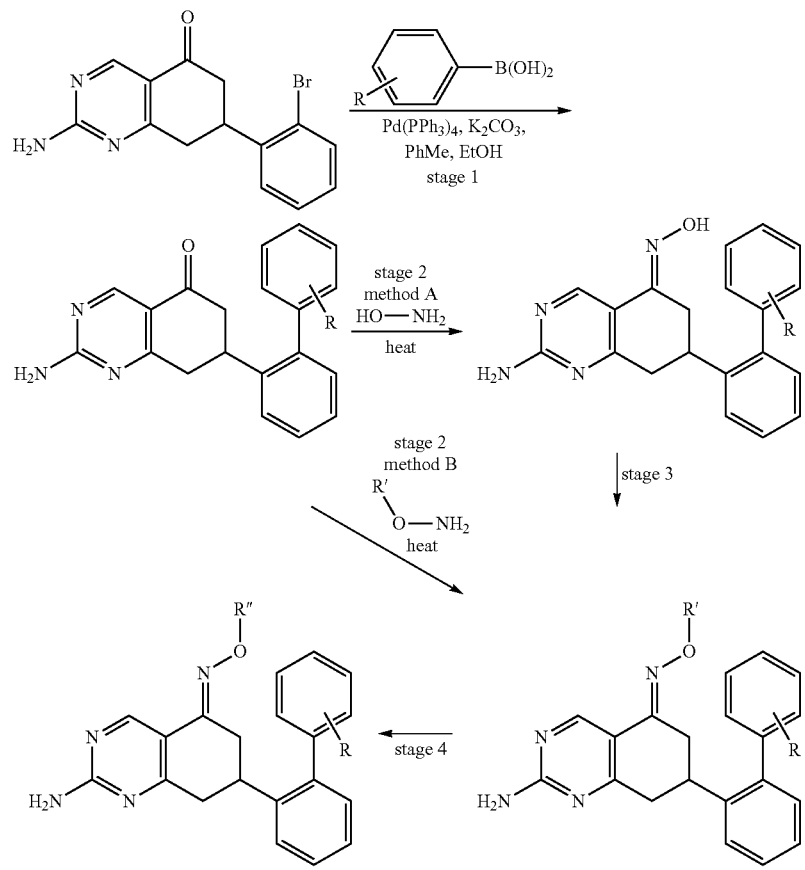

The stage 2 method A derivatives can be further alkylated with an R' group (stage 3). The stage 3 derivatives where R'≠H can also be further functionalized with an R" group (stage 4).

EXAMPLE 4

Synthesis of Compounds of 2-amino-7-biaryl-6H-quinazolin-5-one oxime derivatives using Scheme 4 a. 2-Amino-7-(4-fluoro-2-pyridin-3-yl-phenyl)-7,8-dihydro-6H-quinazolin-5-one oxime (Compound 51)

Stage 1: 2-Amino-7-(4-fluoro-2-pyridin-3-yl-phenyl)-7,8-dihydro-6H-quinazolin-5-one

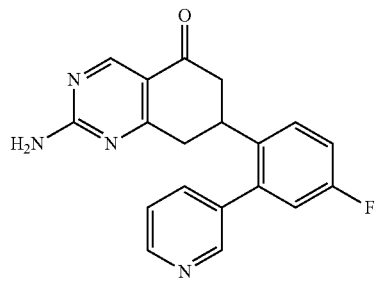 [SMILES: Nc1ncc2c(n1)CC(c1ccc(F)cc1-c1cccnc1)CC2=O]

To a microwave vessel was added 2-amino-7-(2-bromo-4-fluoro-phenyl)-7,8-dihydro-6H-quinazolin-5-one (30 mg, 0.089 mmol), example 2/i stage 2, pyridine-3-boronic acid (22 mg, 0.11 mmol), potassium carbonate (51 mg, 0.22 mmol) and tetrakis(triphenylphosphine)palladium (9 mg, 5 mol %), in a 2:1 mixture of ethanol:toluene (1 ml) and the suspension thoroughly degassed. The reaction mixture was then heated in a CEM microwave at 300 W, 150° C. with a 5 min ramp time and a hold time of 30 min. On completion of the reaction the solution was filtered through celite and then the cake further washed with fresh methanol. The combined washings were evaporated to give a pale yellow residue which was triturated with fresh diethyl ether and the desired product removed by filtration as a pale yellow solid.

Yield: 47.5 mg (96%)

Mass spectrum (ES-MS (+ve)) 335 [MH]$^+$, Retention time 1.26 min, 100% UV.

1H NMR (250 MHz, CHLOROFORM-d) δ ppm 8.84 (1H, s), 8.63 (1H, dd), 8.55 (1H, dd), 7.53-7.66 (1H, m), 7.31-7.49 (2H, m), 7.10-7.23 (1H, m), 6.97 (1H, dd), 5.48 (2H, br. s), 3.34-3.48 (1H, m), 2.98-3.16 (1H, m), 2.80-2.94 (1H, m), 2.60-2.78 (2H, m).

Stage 2

Method A—2-Amino-7-(4-fluoro-2-pyridin-3-yl-phenyl)-7,8-dihydro-6H-quinazolin-5-one oxime (Compound 51)

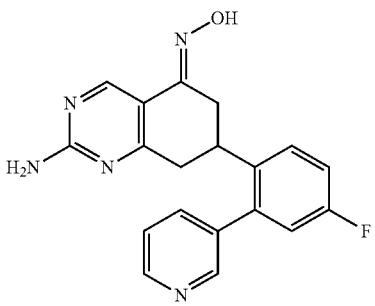 [SMILES: Nc1ncc2c(n1)CC(c1ccc(F)cc1-c1cccnc1)C/C2=N\O]

To a stirred solution of 2-amino-7-(4-fluoro-2-pyridin-3-yl-phenyl)-7,8-dihydro-6H-quinazolin-5-one (15 mg, 0.045 mmol) from stage 1, in pyridine (1 ml) at ambient temperature was added hydroxylamine hydrochloride (12 mg, 0.18 mmol). The reaction mixture was heated at 60° C. for 1 h. The reaction mixture was then cooled to ambient temperature and diluted with water (2 ml). The precipitate formed was filtered and dried under air suction followed by high vacuum.

Yield: 8 mg (51%)

Mass spectrum (ES-MS (+ve)) 350 [MH]$^+$, Retention time 2.82 min, 90% UV.

1H NMR (250 MHz, DMSO-d$_6$) δ ppm 10.89 (1H, s), 8.52-8.57 (2H, m), 7.72-7.82 (1H, m), 7.67 (1H, dd), 7.44 (1H, dd), 7.24-7.35 (1H, m), 7.10 (1H, dd), 6.83 (2H, br. s), 2.89-3.09 (3H, m), 2.40-2.59 (2H, m).

b. 2-Amino-7-biphenyl-2-yl-7,8-dihydro-6H-quinazolin-5-one oxime derivatives (Compounds 52 to 61)

Stage 1: 2-Amino-7-biphenyl-2-yl-7,8-dihydro-6H-quinazolin-5-one

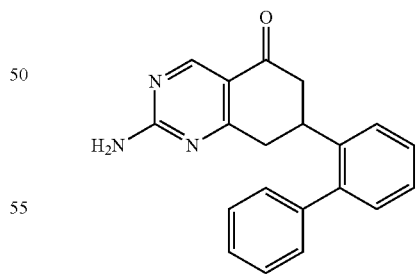

The title compound was prepared from 2-amino-7-(2-bromo-phenyl)-7,8-dihydro-6H-quinazolin-5-one (example 2/h stage 2), following the procedure describing the synthesis of 2-amino-7-(4-fluoro-2-pyridin-3-yl-phenyl)-7,8-dihydro-6H-quinazolin-5-one (example 4/a stage 1) except for phenylboronic acid replacing 3-pyridylboronic acid.

Mass spectrum (ES-MS (+ve)) 316 [MH]$^+$, Retention time 4.05 min, 87% UV.

1H NMR (360 MHz, DMSO-d$_6$) δ ppm 8.60 (1H, s), 7.64 (3H, d), 7.29-7.48 (7H, m), 7.20 (1H, d), 3.44 (1H, t), 3.19 (1H, dd), 2.96 (1H, dd), 2.68 (1H, d), 2.46 (1H, br. s).

Stage 2

Method A—2-Amino-7-biphenyl-2-yl-7,8-dihydro-6H-quinazolin-5-one oxime (Compound 52)

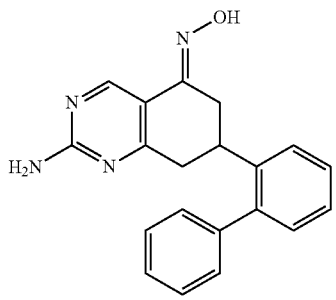 [SMILES: Nc1ncc2c(n1)CC(c1ccccc1-c1ccccc1)C/C2=N\O]

The title compound was prepared from 2-amino-7-biphenyl-2-yl-7,8-dihydro-6H-quinazolin-5-one from stage 1, following the procedure describing the synthesis of 2-amino-7-(4-fluoro-2-pyridin-3-yl-phenyl)-7,8-dihydro-6H-quinazolin-5-one oxime (example 4/a stage 2).

Mass spectrum (ES-MS (+ve)) 331 [MH]$^+$, Retention time 3.83 min, 99% UV.

1H NMR (360 MHz, DMSO-d$_6$) δ ppm 10.89 (1H, s), 8.56 (1H, s), 7.60 (1H, d), 7.39-7.41 (3H, m), 7.26-7.35 (4H, m), 7.18 (1H, d), 6.85 (2H, br. s), 2.99-3.08 (3H, m), 2.54-2.58 (1H, m), 2.08 (1H, s).

Stage 2

Method B—2-Amino-7-biphenyl-2-yl-7,8-dihydro-6H-quinazolin-5-one O-methyl-oxime (Compound 53)

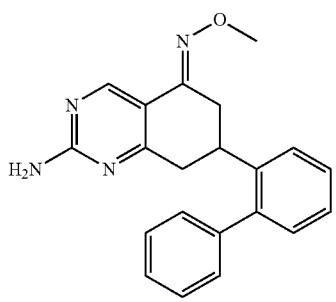 [SMILES: CO/N=C1\CC(c2ccccc2-c2ccccc2)Cc2nc(N)ncc21]

The title compound was prepared from 2-amino-7-biphenyl-2-yl-7,8-dihydro-6H-quinazolin-5-one from stage 1, following the procedure describing the synthesis of 2-amino-7-(4-fluoro-2-pyridin-3-yl-phenyl)-7,8-dihydro-6H-quinazolin-5-one oxime (example 4/a stage 2) utilising methoxylamine hydrochloride instead of hydroxylamine.

Mass spectrum (ES-MS (+ve)) 345 [MH]$^+$, Retention time 4.34+4.54 min, 99% UV.

1H NMR (400 MHz, DMSO-d$_6$) indicated the presence of two oxime stereoisomers in a 2:3 ratio, δ ppm 9.22 (1H (2:3), s), 8.55 (1H (3:2), s), 7.59 (1H (3:2), d), 7.55 (1H (2:3), d), 7.26-7.40 (7H, m), 7.18-7.20 (1H, d), 7.12 (2H (2:3) br. s), 6.97 (2H (3:2), br. s.), 3.80 (3H (3:2), s), 3.78 (3H (2:3), s), 2.95-3.12 (3H, m), 2.77-2.80 (1H, m), 2.57-2.53 (1H, m).

The following compounds were also synthesized using a route equivalent to that described above with appropriately chosen starting materials:

Stage 2

Method B—(2-Amino-7-biphenyl-2-yl-7,8-dihydro-6H-quinazolin-5-ylideneaminooxy)-acetic acid (Compound 54)

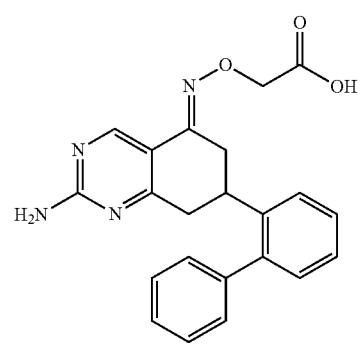 [SMILES: Nc1ncc2c(n1)CC(c1ccccc1-c1ccccc1)C/C2=N\OCC(=O)O]

The title compound was prepared from 2-amino-7-biphenyl-2-yl-7,8-dihydro-6H-quinazolin-5-one from stage 1, following the procedure describing the synthesis of 2-amino-7-(4-fluoro-2-pyridin-3-yl-phenyl)-7,8-dihydro-6H-quinazolin-5-one oxime (example 4/a stage 2) utilising aminooxy-acetic acid instead of hydroxylamine.

Mass spectrum (ES-MS (+ve)) 389 [MH]$^+$, Retention time 3.85 min, 100% UV.

1H NMR (400 MHz, DMSO-d$_6$) δ ppm 8.52 (1H, s), 7.62 (1H, d), 7.40-7.43 (3H, m), 7.27-7.35 (4H, m), 7.18 (1H, d), 6.90 (2H, br. s), 4.14 (2H, s), 2.93-3.14 (3H, m), 2.56-2.60 (1H, m), 2.52-2.54 (1H, m).

Stage 3: 2-Amino-7-biphenyl-2-yl-7,8-dihydro-6H-quinazolin-5-one O-(2-morpholin-4-yl-2-oxo-ethyl)-oxime (Compound 55)

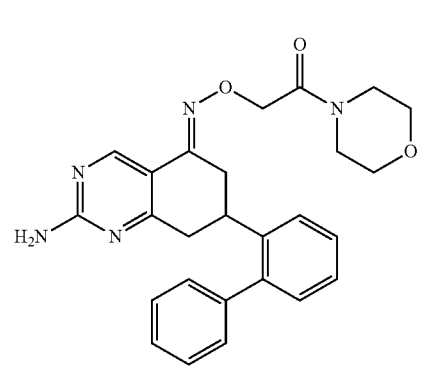 [SMILES: Nc1ncc2c(n1)CC(c1ccccc1-c1ccccc1)C/C2=N\OCC(=O)N1CCOCC1]

The title compound was prepared from (2-amino-7-biphenyl-2-yl-7,8-dihydro-6H-quinazolin-5-ylideneaminooxy)-acetic acid (compound 54) by treating with thionyl chloride followed by amidation using morpholine and triethylamine in DCM.

Mass spectrum (ES-MS (+ve)) 458 [MH]+, Retention time 3.89 min, 100% UV.

1H NMR (400 MHz, DMSO-d$_6$) δ ppm 8.51 (1H, s), 7.62 (1H, d), 7.40-7.43 (3H, m), 7.28-7.36 (4H, m), 7.19 (1H, d), 7.02 (2H, br. s), 4.75 (2H, s), 3.52 (4H, br. s), 3.40 (4H, br. s), 2.98-3.15 (3H, m), 2.55-2.67 (2H, m).

Stage 2

Method B—2-Amino-7-biphenyl-2-yl-7,8-dihydro-6H-quinazolin-5-one O-ethyl-oxime (Compound 56)

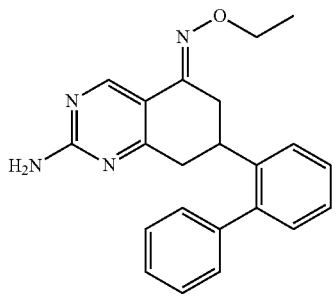 [SMILES: CCO/N=C1\CC(c2ccccc2-c2ccccc2)Cc2nc(N)ncc21]

The title compound was prepared from 2-amino-7-biphenyl-2-yl-7,8-dihydro-6H-quinazolin-5-one from stage 1, following the procedure describing the synthesis of 2-amino-7-(4-fluoro-2-pyridin-3-yl-phenyl)-7,8-dihydro-6H-quinazolin-5-one oxime (example 4/a stage 2) utilising O-ethyl-hydroxylamine instead of hydroxylamine.

Mass spectrum (ES-MS (+ve)) 359 [MH]+, Retention time 4.57+4.80 min, 98% UV.

1H NMR (400 MHz, DMSO-d$_6$) indicated the presence of two oxime stereoisomers in a 1:1 ratio, δ ppm 9.20 (1H (1:1), s), 8.50 (1H (1:1), s), 7.53 (1H (1:1), d), 7.48 (1H (1:1), d), 7.19-7.35 (7H, m), 7.12-7.13 (1H (1:1), m), 7.11-7.10 (1H (1:1), m), 7.03 (2H (1:1), br. s), 6.89 (2H (1:1), br. s), 3.93-4.01 (2H, m), 2.89-3.06 (3H, m), 2.60-2.69 (1H, m), 2.47-2.51 (1H (1:1), m), 2.34-2.39 (1H (1:1), m), 1.09-1.14 (3H, m).

Stage 2

Method B—2-Amino-7-biphenyl-2-yl-7,8-dihydro-6H-quinazolin-5-one O-propyl-oxime (Compound 57)

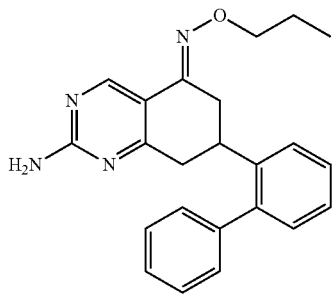 [SMILES: CCCO/N=C1\CC(c2ccccc2-c2ccccc2)Cc2nc(N)ncc21]

The title compound was prepared from 2-amino-7-biphenyl-2-yl-7,8-dihydro-6H-quinazolin-5-one from stage 1, following the procedure describing the synthesis of 2-amino-7-(4-fluoro-2-pyridin-3-yl-phenyl)-7,8-dihydro-6H-quinazolin-5-one oxime (example 4/a stage 2) utilising O-propyl-hydroxylamine instead of hydroxylamine.

Mass spectrum (ES-MS (+ve)) 373 [MH]+, Retention time 4.85+5.10 min, 97% UV.

1H NMR (250 MHz, DMSO-d$_6$) δ ppm 8.56 (1H, s), 7.60 (1H, d), 7.22-7.48 (7H, m), 7.17 (1H, d), 6.95 (2H, br. s), 3.97 (2H, t), 2.92-3.16 (3H, m), 2.47-2.70 (2H, m), 1.39-1.75 (2H, m), 0.86 (3H, t).

Stage 2

Method B—2-Amino-7-biphenyl-2-yl-7,8-dihydro-6H-quinazolin-5-one O-butyl-oxime (Compound 58)

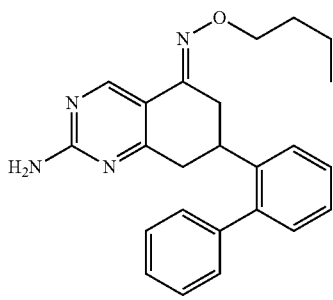 [SMILES: CCCCO/N=C1\CC(c2ccccc2-c2ccccc2)Cc2nc(N)ncc21]

The title compound was prepared from 2-amino-7-biphenyl-2-yl-7,8-dihydro-6H-quinazolin-5-one from stage 1, following the procedure describing the synthesis of 2-amino-7-(4-fluoro-2-pyridin-3-yl-phenyl)-7,8-dihydro-6H-quinazolin-5-one oxime (example 4/a stage 2) utilising O-butyl-hydroxylamine instead of hydroxylamine.

Mass spectrum (ES-MS (+ve)) 387 [MH]+, Retention time 5.11+5.40 min, 99% UV.

1H NMR (250 MHz, DMSO-d$_6$) δ ppm 8.56 (1H, s), 7.60 (1H, d), 7.22-7.49 (7H, m), 7.17 (1H, d), 6.95 (2H, br. s), 4.02 (2H, t), 2.87-3.16 (3H, m), 2.49-2.66 (2H, m), 1.45-1.67 (2H m), 1.11-1.42 (2H, m), 0.88 (3H, t).

Stage 2

Method B—4-(2-Amino-7-biphenyl-2-yl-7,8-dihydro-6H-quinazolin-5-ylideneaminooxy)-butyric acid ethyl ester (Compound 59)

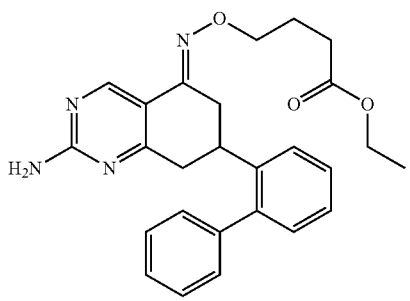

The title compound was prepared from 2-amino-7-biphenyl-2-yl-7,8-dihydro-6H-quinazolin-5-one from stage 1, following the procedure describing the synthesis of 2-amino-7-(4-fluoro-2-pyridin-3-yl-phenyl)-7,8-dihydro-6H- quinazolin-5-one oxime (example 4/a stage 2) utilising 4-aminooxy-butyric acid ethyl ester instead of hydroxylamine.

Mass spectrum (ES-MS (+ve)) 445 [MH]+, Retention time 4.71+4.83 min, 98% UV.

1H NMR (250 MHz, DMSO-$d_6$) δ ppm 8.56 (1H, s), 7.60 (1H, d), 7.23-7.48 (7H, m), 7.18 (1H, d), 6.97 (2H, br. s), 4.03 (2H, t), 3.99 (2H, q), 2.83-3.17 (3H, m), 2.52-2.61 (2H, m), 2.33 (2H, t), 1.64-1.95 (2H, m), 1.12 (3H, t).

The 4-aminooxy-butyric acid ethyl ester was prepared by condensation of 4-bromo-butyric acid ethyl ester on N-hydroxyphthalamide followed by standard hydrazine deprotection.

Stage 4: 4-(2-Amino-7-biphenyl-2-yl-7,8-dihydro-6H-quinazolin-5-ylideneaminooxy)-butyric acid (Compound 60)

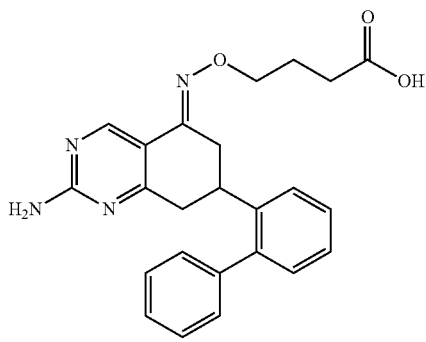 [SMILES: Nc1ncc2c(n1)CC(c1ccccc1-c1ccccc1)C/C2=N\OCCCC(=O)O]

The title compound was prepared from 4-(2-amino-7-biphenyl-2-yl-7,8-dihydro-6H-quinazolin-5-ylideneaminooxy)-butyric acid ethyl ester (compound 59) and the ethyl ester hydrolysed under standard conditions.

Mass spectrum (ES-MS (+ve)) 417 [MH]+, Retention time 4.17 min, 100% UV.

1H NMR (360 MHz, DMSO-$d_6$) δ ppm 8.55 (1H, s), 7.56 (1H, d), 7.21-7.44 (7H, m), 7.16 (1H, d), 6.91 (2H, br. s), 4.01 (2H, t), 2.93-3.07 (3H, m), 2.58-2.80 (2H, m), 2.25 (2H, t), 1.7) (2H, t).

Stage 2

Method B—2-Amino-7-biphenyl-2-yl-7,8-dihydro-6H-quinazolin-5-one O-(2-morpholin-4-yl-ethyl)-oxime (Compound 61)

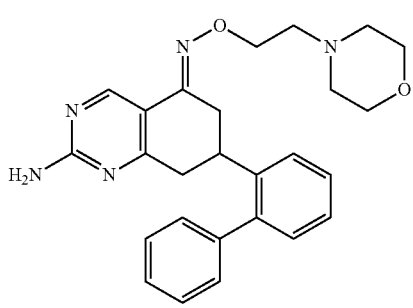 [SMILES: Nc1ncc2c(n1)CC(c1ccccc1-c1ccccc1)C/C2=N\OCCN1CCOCC1]

The title compound was prepared from 2-amino-7-biphenyl-2-yl-7,8-dihydro-6H-quinazolin-5-one from stage 1, following the procedure describing the synthesis of 2-amino-7-(4-fluoro-2-pyridin-3-yl-phenyl)-7,8-dihydro-6H-quinazolin-5-one oxime (example 4/a stage 2) utilising O-(2-morpholin-4-yl-ethyl)-hydroxylamine instead hydroxylamine.

Mass spectrum (ES-MS (+ve)) 444 [MH]+, Retention time 3.13+3.17 min, 97% UV.

1H NMR (360 MHz, DMSO-$d_6$) indicated the presence of two oxime stereoisomers in a 3:5 ratio, δ ppm 9.35 (1H (3:5), s), 8.58 (1H (5:3), s), 7.61 (1H (5:3), d), 7.56 (1H (3:5), d), 7.27-7.44 (7H, m), 7.20 (1H, d), 7.12 (2H (3:5) br. s), 6.98 (2H (5:3), br. s), 4.59 (2H (3:5), t), 4.12-4.17 (2H (5:3), t), 3.56 (4H, br. s), 3.44 (1H, d), 2.97-3.11 (2H, m), 2.68-2.82 (1H, m), 2.59 (1H, d), 2.42 (4H, br. s).

The O-(2-morpholin-4-yl-ethyl)-hydroxylamine was prepared by condensation of 4-(2-bromo-ethyl)-morpholine on N-hydroxyphthalamide followed by standard hydrazine deprotection.

c. 2-Amino-7-(2-pyridin-2-yl-phenyl)-7,8-dihydro-6H-quinazolin-5-one oxime (Compound 62)

Stage 1: 2-Amino-7-(2-pyridin-2-yl-phenyl)-7,8-dihydro-6H-quinazolin-5-one

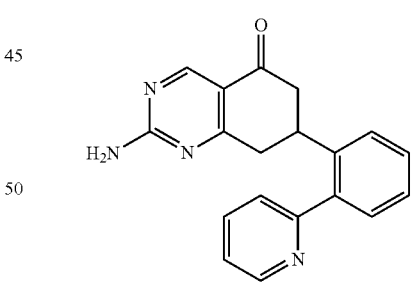

The title compound was prepared from 2-amino-7-(2-bromo-phenyl)-7,8-dihydro-6H-quinazolin-5-one (example 2/h stage 2), following the procedure describing the synthesis of 2-amino-7-(4-fluoro-2-pyridin-3-yl-phenyl)-7,8-dihydro-6H-quinazolin-5-one (example 4/a stage 1) using 2-pyridyl boronic acid instead of 3-pyridyl boronic acid.

Mass spectrum (ES-MS (+ve)) 317 [MH]+, Retention time 2.73 min, 100% UV.

1H NMR (360 MHz, DMSO-d$_6$) δ ppm 8.61 (2H, s), 7.89 (1H, t), 7.44-7.70 (5H, m), 7.31-7.41 (3H, m), 3.64-3.77 (1H, m), 3.18 (1H, dd), 2.95 (1H, dd), 2.80 (1H, dd), 2.58 (1H, br. s).

Stage 2

Method A—2-Amino-7-(2-pyridin-2-yl-phenyl)-7,8-dihydro-6H-quinazolin-5-one oxime (Compound 62)

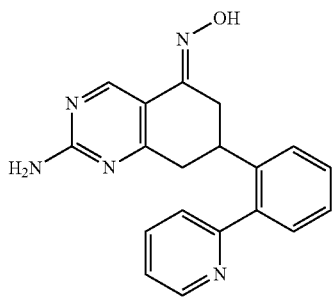 [SMILES: Nc1ncc2c(n1)CC(c1ccccc1-c1ccccn1)C/C2=N\O]

The title compound was prepared from 2-amino-7-(2-pyridin-2-yl-phenyl)-7,8-dihydro-6H-quinazolin-5-one from stage 1, following the procedure describing the synthesis of 2-amino-7-(4-fluoro-2-pyridin-3-yl-phenyl)-7,8-dihydro-6H-quinazolin-5-one oxime (example 4/a stage 2).

Mass spectrum (ES-MS (+ve)) 332 [MH]$^+$, Retention time 2.65 min, 97% UV.

1H NMR (360 MHz, DMSO-d$_6$) δ ppm 10.87 (1H, s), 8.54-8.66 (2H, m), 7.88 (1H, t), 7.63 (1H, d), 7.43-7.54 (2H, m), 7.29-7.41 (3H, m), 6.86 (2H, br. s), 3.29 (1H, br. s), 3.16 (1H, d), 2.98 (1H, m), 2.67 (1H, d), 2.45 (1H, br. s).

d. 2-Amino-7-(2-pyridin-3-yl-phenyl)-7,8-dihydro-6H-quinazolin-5-one oxime (Compound 63)

Stage 1: 2-Amino-7-(2-pyridin-3-yl-phenyl)-7,8-dihydro-6H-quinazolin-5-one

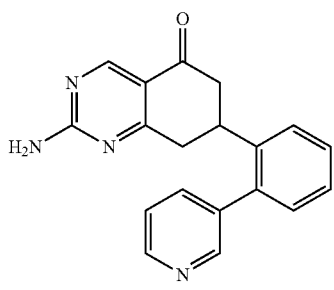 [SMILES: Nc1ncc2c(n1)CC(c1ccccc1-c1cccnc1)CC2=O]

The title compound was prepared from 2-amino-7-(2-bromo-phenyl)-7,8-dihydro-6H-quinazolin-5-one (example 2/h stage 2), following the procedure describing the synthesis of 2-amino-7-(4-fluoro-2-pyridin-3-yl-phenyl)-7,8-dihydro-6H-quinazolin-5-one (example 4/a stage 1).

Mass spectrum (ES-MS (+ve)) 317 [MH]$^+$, Retention time 2.63 min, 98% UV.

1H NMR (360 MHz, DMSO-d$_6$) δ ppm 8.50 (1H, s), 8.46 (2H, br. s), 7.70 (1H, d), 7.59 (1H, d), 7.52 (2H, br. s), 7.39 (2H, d), 7.28 (1H, t), 7.15 (1H, d), 3.20-3.32 (1H, m), 3.03-3.18 (1H, m), 2.79-2.94 (1H, m), 2.61 (1H, d), 2.34-2.50 (1H, m).

Stage 2

Method A—2-Amino-7-(2-pyridin-3-yl-phenyl)-7,8-dihydro-6H-quinazolin-5-one oxime (Compound 63)

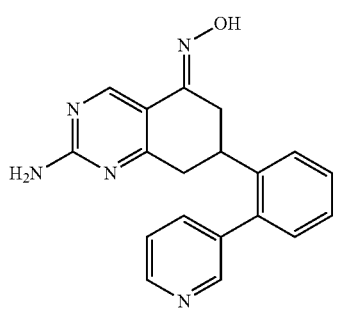 [SMILES: Nc1ncc2c(n1)CC(c1ccccc1-c1cccnc1)C/C2=N\O]

The title compound was prepared from 2-amino-7-(2-pyridin-3-yl-phenyl)-7,8-dihydro-6H-quinazolin-5-one from stage 1, following the procedure describing the synthesis of 2-amino-7-(4-fluoro-2-pyridin-3-yl-phenyl)-7,8-dihydro-6H-quinazolin-5-one oxime (example 4/a stage 2).

Mass spectrum (ES-MS (+ve)) 332 [MH]$^+$, Retention time 2.52+2.61 min, 99% UV.

1H NMR (400 MHz, DMSO-d$_6$) indicated the presence of two oxime stereoisomers in a 1:2 ratio, δ ppm 10.86 (1H, br.s), 9.35 (1H (1:2), s), 8.50 (1H (2:1), s), 8.45-8.49 (2H m), 7.69 (1H, t), 7.58 (1H (2:1), d), 7.53 (1H (1:2), d), 7.36-7.42 (2H, m), 7.29 (1H, t), 7.16 (1H, d), 6.95 (2H (1:2), br. s), 6.80 (2H (2:1), br. s), 2.89-3.03 (3H, m), 2.61-2.68 (1H, m), 2.53 (1H, d).

e. 2-Amine-7-(2-pyridin-4-yl-phenyl)-7,8-dihydro-6H-quinazolin-5-one oxime (Compound 64)

Stage 1: 2-Amino-7-(2-pyridin-4-yl-phenyl)-7,8-dihydro-6H-quinazolin-5-one

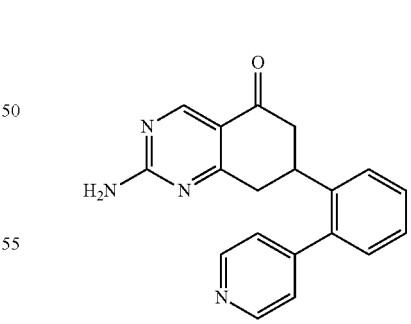

The title compound was prepared from 2-amino-7-(2-bromo-phenyl)-7,8-dihydro-6H-quinazolin-5-one (example 2/h stage 2), following the procedure describing the synthesis of 2-amino-7-(4-fluoro-2-pyridin-3-yl-phenyl)-7,8-dihydro-6H-quinazolin-5-one using 4-pyridyl boronic acid instead of 3-pyridyl boronic acid.

Mass spectrum (ES-MS (+ve)) 317 [MH]$^+$, Retention time 2.53 min, 93% UV.

1H NMR (400 MHz, DMSO-d$_6$) 8.53-8.65 (3H, m), 7.67 (1H, d), 7.60 (2+1, br. s), 7.48 (1H, t), 7.35-7.37 (3H, m), 7.21 (1H, d), 3.28-3.45 (1H, m), 3.18 (1H, dd), 2.94 (1H, dd), 2.61-2.73 (1H, m), 2.42-2.54 (1H, m).

Stage 2: 2-Amino-7-(2-pyridin-4-yl-phenyl)-7,8-dihydro-6H-quinazolin-5-one oxime (Compound 64)

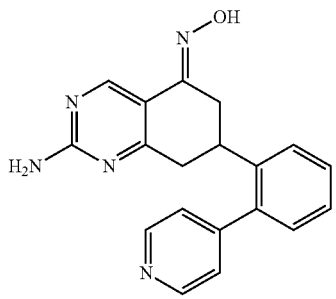 [SMILES: Nc1ncc2c(n1)CC(c1ccccc1-c1ccncc1)C/C2=N\O]

The title compound was prepared from 2-amino-7-(2-pyridin-4-yl-phenyl)-7,8-dihydro-6H-quinazolin-5-one from stage 1, following the procedure describing the synthesis of 2-amino-7-(4-fluoro-2-pyridin-3-yl-phenyl)-7,8-dihydro-6H-quinazolin-5-one oxime (example 4/a stage 2).

Mass spectrum (ES-MS (+ve)) 332 [MH]$^+$, Retention time 2.43+2.52 min, 99% UV.

1H NMR (360 MHz, DMSO-d$_6$) indicated the presence of two oxime stereoisomers in a 1:2 ratio, δ ppm 10.99 (1H (1:2), br. s), 10.90 (1H (2:1), br. s), 9.43 (2H (1:2), s), 8.60 (2H (2:1), br. s), 7.61-7.67 (1H, m), 7.49 (1H, br. s), 7.36 (5H, br. s), 7.22 (1H, d), 7.01 (1H (1:2), br. s), 6.85 (1H (2:1), br. s), 3.00-3.12 (3H, m), 2.69-2.78 (1H, m), 2.60-2.62 (1H, m).

f. 2-Amino-7-[4-fluoro-2-(1-methyl-1H-pyrazol-4-yl)-phenyl]-7,8-dihydro-6H-quinazolin-5-one oxime (Compound 65)

Stage 1: 2-Amino-7-[4-fluoro-2-(1-methyl-1H-pyrazol-4-yl)-phenyl]-7,6-dihydro-6H-quinazolin-5-one

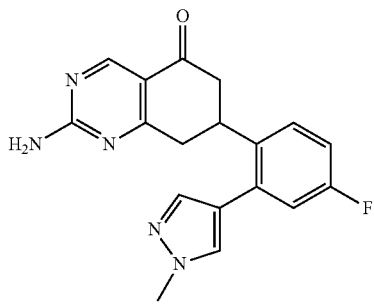 [SMILES: Cn1cc(-c2cc(F)ccc2C2CC(=O)c3cnc(N)nc3C2)cn1]

The title compound was prepared from 2-amino-7-(2-bromo-4-fluoro-phenyl)-7,8-dihydro-6H-quinazolin-5-one (example 2/i stage 2), following the procedure describing the synthesis of 2-amino-7-(4-fluoro-2-pyridin-3-yl-phenyl)-7,8-dihydro-6H-quinazolin-5-one (example 4/a stage 1).

Mass spectrum (ES-MS (+ve)) 338 [MH]$^+$, Retention time 1.56 min, 82% UV.

Stage 2: 2-Amino-7-[4-fluoro-2-(1-methyl-1H-pyrazol-4-yl)-phenyl]-7,8-dihydro-6H-quinazolin-5-one oxime (Compound 65)

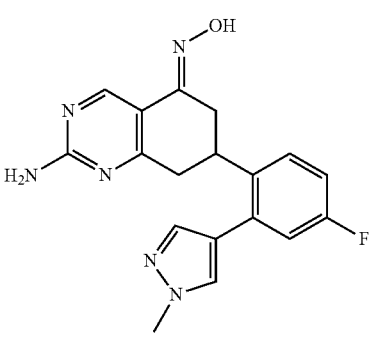 [SMILES: Cn1cc(-c2cc(F)ccc2C2C/C(=N\O)c3cnc(N)nc3C2)cn1]

The title compound was prepared from 2-amino-7-[4-fluoro-2-(1-methyl-1H-pyrazol-4-yl)-phenyl]-7,8-dihydro-6H-quinazolin-5-one from stage 1, following the procedure describing the synthesis of 2-amino-7-(4-fluoro-2-pyridin-3-yl-phenyl)-7,8-dihydro-6H-quinazolin-5-one oxime (example 4/a stage 2).

Mass spectrum (ES-MS (+ve)) 353 [MH]$^+$, Retention time 3.25 min, 90% UV.

g. 2-Amino-7,2-(1H-indol-7-yl)-phenyl'-7,8-dihydro-6H-quinazolin-5-one

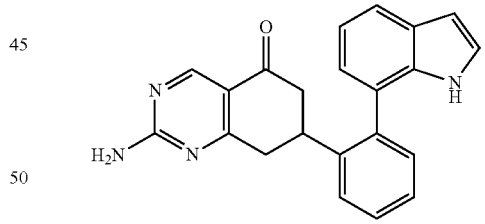

The title compound was prepared from 2-amino-7-(2-bromo-phenyl)-7,8-dihydro-6H-quinazolin-5-one (example 2/h stage 2), following the procedure describing the synthesis of 2-amino-7-(4-fluoro-2-pyridin-3-yl-phenyl)-7,8-dihydro-6H-quinazolin-5-one (example 4/a stage 1) using 7-boronic acid-1H-indole instead of 3-pyridyl boronic acid.

Mass spectrum (ES-MS (+ve)) 355 [MH]$^+$, Retention time 3.94 min, 84% UV.

1H NMR (360 MHz, DMSO-d$_6$) δ ppm 10.71 (1H, d), 8.52 (1H, s), 7.47-7.74 (3H, m), 7.33-7.44 (3H, m), 7.20-7.30 (2H, m), 7.05 (1H, t), 6.86-6.96 (1H, m), 6.47 (1H, br. s), 3.11-3.26 (1H, m), 2.97-3.09 (1H, m), 2.83-2.96 (1H, m), 2.59-2.81 (2H, m).

h. 2-Amino-7-[2-(1H-indol-4-yl)-phenyl]-7,8-dihydro-6H-quinazolin-5-one

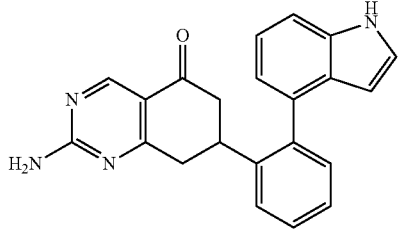 [SMILES: Nc1ncc2c(n1)CC(c1ccccc1-c1cccc3[nH]ccc13)CC2=O]

The title compound was prepared from 2-amino-7-(2-bromo-phenyl)-7,8-dihydro-6H-quinazolin-5-one (example 2/h stage 2), following the procedure describing the synthesis of 2-amino-7-(4-fluoro-2-pyridin-3-yl-phenyl)-7,8-dihydro-6H-quinazolin-5-one using 4-boronic acid-1H-indole instead of 3-pyridyl boronic acid.

Mass spectrum (ES-MS (+ve)) 355 [MH]$^+$, Retention time 3.87 min, 96% UV.

1H NMR (250 MHz, DMSO-d$_6$) δ ppm 11.22 (1H, br. s), 8.51 (1H, d), 7.65 (1H, dd), 7.56 (2H, br. s), 7.44 (1H, td), 7.28-7.39 (4H, m), 7.16-7.26 (1H, m), 7.12 (1H, t), 6.84 (1H, dd), 2.72-3.18 (2H, m), 2.29-2.68 (3H, m).

General procedures for the synthesis of 2-amino-7-biaryl-2-yl-4-methyl-7,8-dihydro-6H-quinazolin-5-one oxime derivatives

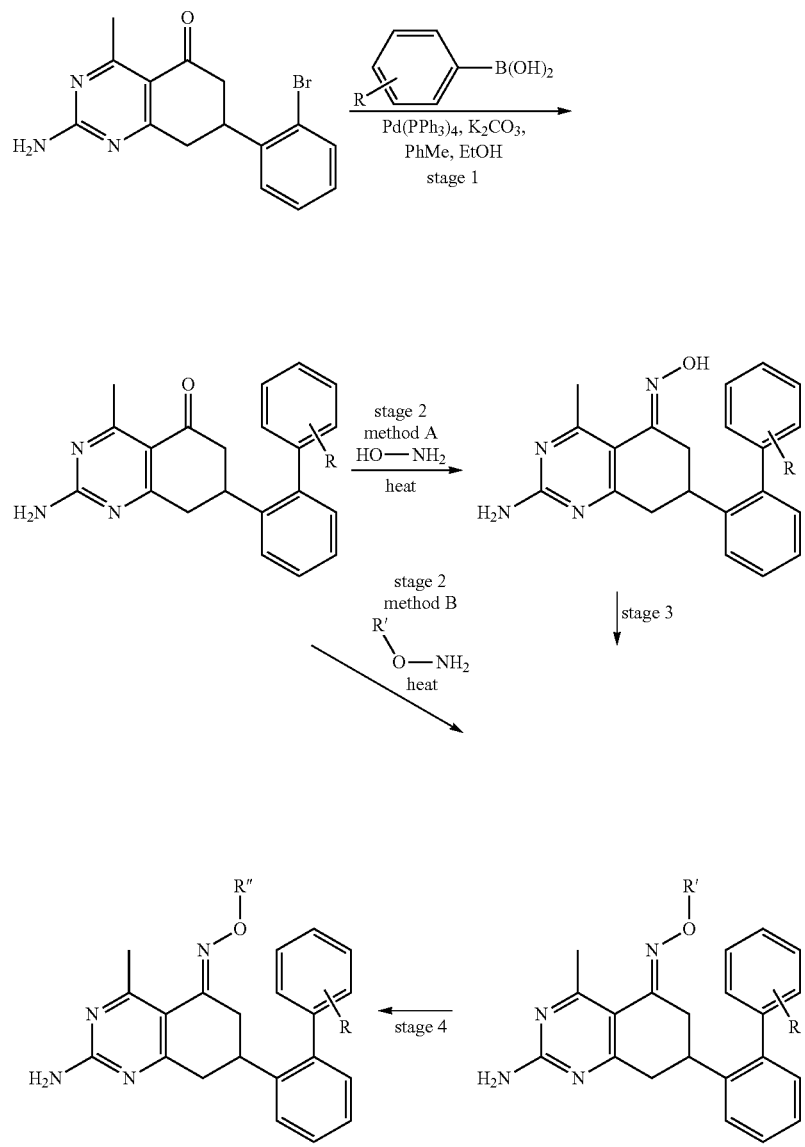

Scheme 5

The stage 2 method A derivatives can be further alkylated with an R' group (stage 3). The stage 3 derivatives where R'≠H can also be further functionalized with an R" group (stage 4).

EXAMPLE 5

Synthesis of Compounds of General Formula (V) using Scheme 5 a. 2-Amino-7-biphenyl-2-yl-4-methyl-7,8-dihydro-6H-quinazolin-5-one oxime and 2-amino-7-biphenyl-2-yl-4-methyl-7,8-dihydro-6H-quinazolin-5-one O-methyl-oxime (Compounds 66 and 67)

Stage 1: 2-Amino-7-biphenyl-2-yl-4-methyl-7,8-dihydro-6H-quinazolin-5-one

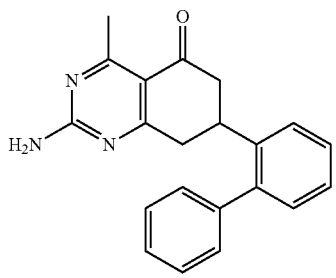 [SMILES: Cc1nc(N)nc2c1C(=O)CC(c1ccccc1-c1ccccc1)C2]

Pd(dppf)$_2$Cl$_2$.CH$_2$Cl$_2$ (52 mg, 0.0629 mmol), was added to a solution of 2-amino-7(-2-bromo-phenyl)-4-methyl-7,8-dihydro-6H-quinazolin-5-one (250 mg, 0.753 mmol), example 3/i stage 2/3, phenylboronic acid (192 mg, 1.57 mmol) and potassium carbonate (0.629 ml, 1.26 mmol, 2M in water) in N,N-dimethylacetamide (5 ml). The reaction mixture was heated in a CEM microwave at 150° C. for 10 min under N$_2$. The reaction mixture was diluted with EtOAc and the resulting solution successively washed with saturated sodium metabisulphite solution and brine. The organic phase was dried with Na$_2$SO$_4$ and filtered. The solvent was removed under reduced pressure. The solid precipitate was washed with diethyl ether. The desired compound was dried under air suction.

Yield: 114 mg (44%)

5. Mass spectrum (ES-MS (+ve)) 330 [MH]$^+$, Retention time 1.96 min, 95% UV

1H NMR (250 MHz, DMSO-d$_6$) δ ppm 7.56-7.63 (1H, m), 7.25-7.48 (9H, m), 7.13-7.20 (1H, m), 3.35-3.43 (1H, m), 3.05-3.24 (1H, m), 2.83-3.00 (1H, m), 2.60-2.80 (1H, m), 2.38-2.58 (1H, m), 2.48-2.50 (3H, m).

Stage 2

Method A—2-Amino-7-biphenyl-2-yl-4-methyl-7,8-dihydro-6H-quinazolin-5-one oxime (Compound 66)

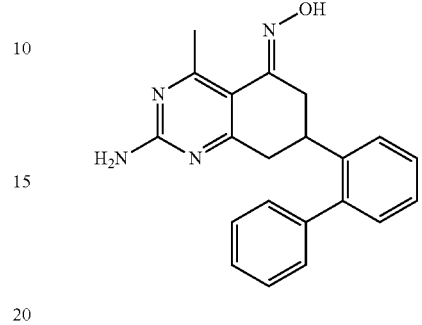

To a stirred solution of 2-amino-7-biphenyl-2-yl-4-methyl-7,8-dihydro-6H-quinazolin-5-one (100 mg, 0.304 mmol), from stage 1, in pyridine (1 ml) was added hydroxylamine hydrochloride (84 mg, 1.22 mmol). The reaction mixture was heated at 60° C. for 1 h. The reaction mixture was cooled to ambient temperature and allowed to stir for 16 h. Water (5 ml) was added and the resulting precipitate was filtered and washed further with water. The desired compound was dried under air suction.

Yield: 95 mg (91%)

Mass spectrum (ES-MS (+ve)) 345 [MH]$^+$, Retention time 1.57 min, 93% UV.

1H NMR (250 MHz, DMSO-d$_6$) δ ppm 10.93 (1H, s), 7.58 (1H, d), 7.21-7.46 (7H, m), 7.17 (1H, d), 6.66 (2H, br. s), 2.82-3.20 (4H, m), 2.51-2.69 (1H, m), 2.43 (3H, s).

Stage 2

Method B—2-Amino-7-biphenyl-2-yl-4-methyl-7,8-dihydro-6H-quinazolin-5-one O-methyl-oxime (Compound 67)

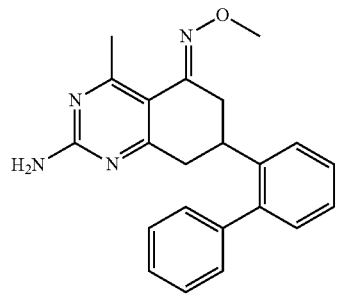

The title compound was prepared from 2-amino-7-biphenyl-2-yl-4-methyl-7,8-dihydro-6H-quinazolin-5-one from stage 1, following the procedure describing the synthesis of 2-amino-7-biphenyl-2-yl-4-methyl-7,8-dihydro-6H-quinazolin-5-one oxime (example 5/a stage 2—method A), except that O-methoxylamine was used instead of hydroxylamine.

Mass spectrum (ES-MS (+ve)) 359 [MH]+, Retention time 4.51 min, 99% UV.

1H NMR (400 MHz, DMSO-d6) δ ppm 7.56 (1H, d), 7.34-7.42 (3H, m), 7.2-7.33 (4H, m), 7.11-7.17 (1H, m), 6.77 (2H, br. s), 3.79 (3H, s), 2.91-3.03 (3H, m), 2.49-2.62 (2H, m), 2.41 (3H, s).

The following compounds were also synthesized using a route equivalent to that described above with appropriately chosen starting materials:

Stage 2

Method B—2-Amino-7-biphenyl-2-yl-4-methyl-7,8-dihydro-6H-quinazolin-5-one O-ethyl-oxime (Compound 68)

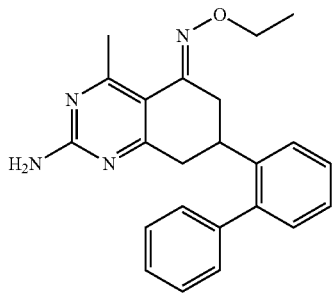 [SMILES: CCO/N=C1\CC(c2ccccc2-c2ccccc2)Cc2nc(N)nc(C)c21]

The title compound was prepared from 2-amino-7-biphenyl-2-yl-4-methyl-7,8-dihydro-6H-quinazolin-5-one from stage 1, following the procedure describing the synthesis of 2-amino-7-biphenyl-2-yl-4-methyl-7,8-dihydro-6H-quinazolin-5-one oxime (example 5/a stage 2—method A), except that O-ethyl hydroxylamine was used instead of hydroxylamine.

Mass spectrum (ES-MS (+ve)) 373 [MH]+, Retention time 4.78 min, 97% UV.

1H NMR (400 MHz, DMSO-d6) δ ppm 7.60 (1H, d), 7.36-7.46 (3H, m), 7.22-7.37 (4H, m), 7.17 (1H, d), 6.78 (2H, br. s), 4.07 (2H, q), 2.94-3.07 (3H, m), 2.52-2.65 (2H, m), 2.44 (3H, s), 1.21 (3H, t).

Stage 2

Method B—(2-Amino-7-biphenyl-2-yl-4-methyl-7,8-dihydro-6H-quinazolin-5-ylideneaminooxy)-acetic acid (Compound 69)

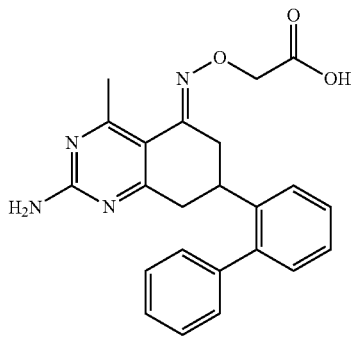

The title compound was prepared from 2-amino-7-biphenyl-2-yl-4-methyl-7,8-dihydro-6H-quinazolin-5-one from stage 1, following the procedure describing the synthesis of 2-amino-7-biphenyl-2-yl-4-methyl-7,8-dihydro-6H-quinazolin-5-one oxime (example 5/a stage 2—method A), except that aminooxy-acetic acid was used instead of hydroxylamine.

Mass spectrum (ES-MS (+ve)) 403 [MH]+, Retention time 3.78 min, 97% UV.

1H NMR (360 MHz, DMSO-d6) δ ppm 7.70 (1H, d), 7.29-7.51 (8H, d), 6.86 (2H, br. s), 4.46 (2H, br. s), 3.53 (1H, br. s), 2.99-3.30 (4H, m), 2.70-2.88 (1H, m), 2.50 (3H, br. s).

Stage 4: 2-Amino-7-biphenyl-2-yl-4-methyl-7,8-dihydro-6H-quinazolin-5-one O-(2-morpholin-4-yl-2-oxo-ethyl)-oxime (Compound 70)

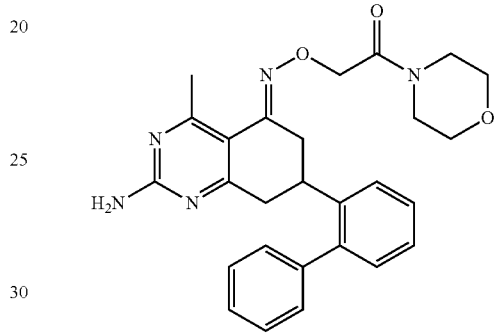

The title compound was prepared from (2-amino-7-biphenyl-2-yl-4-methyl-7,8-dihydro-6H-quinazolin-5-ylideneaminooxy)-acetic acid (compound 69) by treating with thionyl chloride followed by amidation using morpholine and triethylamine in DCM.

Mass spectrum (ES-MS (+ve)) 472 [MH]+, Retention time 3.81 min, 100% UV.

1H NMR (360 MHz, DMSO-d6) δ ppm 7.60 (1H, d), 7.25-7.45 (7H, m), 7.18 (1H, d), 6.83 (2H, br. 4.69-4.78 (2H, m), 3.51 (4H, br. s), 3.40-3.42 (4H, m), 3.00-3.13 (3H, m), 2.56-2.69 (2H, m), 2.38 (3H, s).

Stage 2

Method B—2-Amino-7-biphenyl-2-yl-4-methyl-7,8-dihydro-6H-quinazolin-5-one O-propyl-oxime (Compound 71)

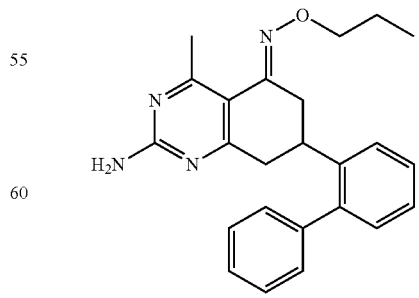

The title compound was prepared from 2-amino-7-biphenyl-2-yl-4-methyl-7,8-dihydro-6H-quinazolin-5-one from stage 1, following the procedure describing the synthesis of 2-amino-7-biphenyl-2-yl-4-methyl-7,8-dihydro-6H-quinazolin-5-one oxime (example 5/a stage 2—method A), except that O-propyl-hydroxylamine was used instead of hydroxylamine.

Mass spectrum (ES-MS (+ve)) 387 [MH]⁺, Retention time 5.07 min, 98% UV.

1H NMR (250 MHz, DMSO-$d_6$) δ ppm 7.58 (1H, d), 7.21-7.45 (7H, m), 7.15 (1H, d), 6.75 (2H, s), 3.97 (2H, t), 3.46 (1H, t), 3.41 (1H, d), 2.94-3.08 (2H, m), 2.57 (1H, s), 2.43 (3H, s), 1.51-1.68 (2H, m), 0.85 (3H, t).

Stage 2

Method B—2-Amino-7-biphenyl-2-yl-4-methyl-7,8-dihydro-6H-quinazolin-5-one O-butyl-oxime (Compound 72)

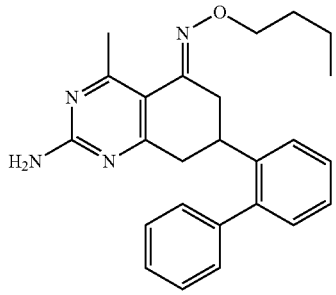

The title compound was prepared from 2-amino-7-biphenyl-2-yl-4-methyl-7,8-dihydro-6H-quinazolin-5-one from stage 1, following the procedure describing the synthesis of 2-amino-7-biphenyl-2-yl-4-methyl-7,8-dihydro-6H-quinazolin-5-one oxime (example 5/a stage 2—method A), except that O-butyl-hydroxylamine was used instead of hydroxylamine.

Mass spectrum (ES-MS (+ve)) 401 [MH]⁺, Retention time 5.39 min, 97% UV.

1H NMR (360 MHz, DMSO-$d_6$) δ ppm 7.61 (1H, d), 7.38-7.47 (3H, m), 7.31-7.38 (2H, m), 7.28 (2H, d), 7.19 (1H, d), 6.79 (2H, s), 4.05 (2H, t), 2.98-3.10 (3H, m), 2.55-2.65 (2H, m), 2.46 (3H, s), 1.54-1.66 (2H, m), 1.29-1.38 (2H, m), 0.90 (3H, t).

Stage 2

Method B—4-(2-Amino-7-biphenyl-2-yl-4-methyl-7,8-dihydro-6H-quinazolin-5-ylideneaminooxy)-butyric acid ethyl ester (Compound 73)

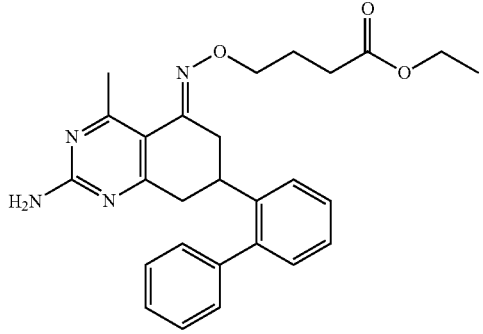 [SMILES: CCOC(=O)CCCO/N=C1\CC(c2ccccc2-c2ccccc2)Cc2nc(N)nc(C)c21]

The title compound was prepared from 2-amino-7-biphenyl-2-yl-4-methyl-7,8-dihydro-6H-quinazolin-5-one from stage 1, following the procedure describing the synthesis of 2-amino-7-biphenyl-2-yl-4-methyl-7,8-dihydro-6H-quinazolin-5-one oxime (example 5/a stage 2—method A), except that 4-aminooxy-butyric acid ethyl ester was used instead of hydroxylamine.

Mass spectrum (ES-MS (+ve)) 459 [MH]⁺, Retention time 4.74 min, 91% UV

1H NMR (360 MHz, DMSO-$d_6$) δ ppm 7.61 (1H, d), 7.38-7.48 (3H, m), 7.25-7.38 (4H, m), 7.19 (1H, d), 6.80 (2H, s), 4.06 (2H, t), 3.99 (2H, q), 2.55-2.67 (2H, m), 2.46 (3H, s), 2.35 (2H, t), 1.89 (2H, t), 1.13 (3H, t).

The 4-aminooxy-butyric acid ethyl ester was prepared by condensation of 4-bromo-butyric acid ethyl ester on N-hydroxyphthalamide followed by standard hydrazine deprotection.

Stage 3: 2-Amino-7-biphenyl-2-yl-4-methyl-7,8-dihydro-6H-quinazolin-5-one O-(3-morpholin-4-yl-propyl)-oxime (Compound 74)

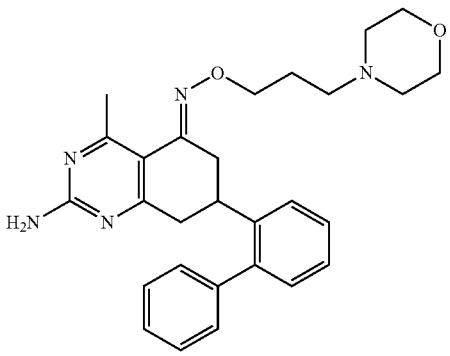 [SMILES: Cc1nc(N)nc2c1/C(=N/OCCCN1CCOCC1)CC(c1ccccc1-c1ccccc1)C2]

The title compound was prepared from 2-amino-7-biphenyl-2-yl-4-methyl-7,8-dihydro-6H-quinazolin-5-one oxime, compound 66, (100 mg, 0.290 mmol), 4-(3-chloro-propyl)-morpholine hydrochloride (70 mg, 0.348 mmol) and sodium hydride (60% dispersion in oil) (37 mg, 0.928 mmol) following the same procedure used for 2-amino-7-(4-fluoro-biphenyl-2-yl)-4-methyl-7,8-dihydro-6H-quinazolin-5-one O-(3-dimethylamino-propyl)-oxime (compound 88) except after addition of water the solvent was removed under reduced pressure. The crude material was taken up in EtOAc (20 ml) and the resulting solution was filtered. The solvent was removed under reduced pressure and the title compound was purified by column chromatography eluting with dichloromethane/methanol (97/3).

Yield=110 mg (80%)

Mass spectrum (ES-MS (+ve)) 472 [MH]⁺, Retention time 2.98 min, 91% UV.

1H NMR (250 MHz, CHLOROFORM-d) δ ppm 7.13-7.44 (9H, m), 5.19 (2H, br. s.), 4.08 (2H, t), 3.64 (4H, t), 3.09-3.13 (2H, m), 2.76-2.93 (1H, m), 2.60-2.76 (1H, m), 2.47-2.54 (1H, m), 2.50 (3H, s), 2.34-2.36 (6H, m), 1.74-1.85 (2H, m). The O-(2-morpholin-4-yl-ethyl)-hydroxylamine was prepared by condensation of 4-(2-bromo-ethyl)-morpholine on N-hydroxyphthalamide followed by standard hydrazine deprotection.

Stage 3: 2-Amino-7-biphenyl-2-yl-4-methyl-7,8-dihydro-6H-quinazolin-5-one O-[3-(4-methyl-piperazin-1-yl)-propyl]-oxime (Compound 75)

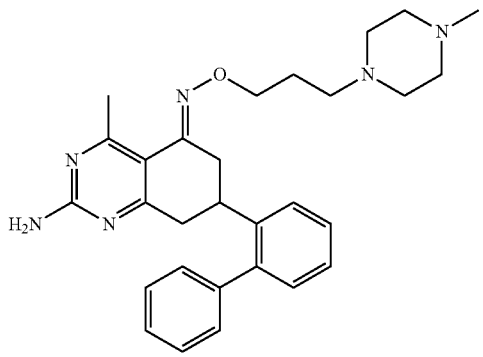 [SMILES: Cc1nc(N)nc2c1/C(=N/OCCCN1CCN(C)CC1)CC(c1ccccc1-c1ccccc1)C2]

The title compound was prepared from 2-amino-7-biphenyl-2-yl-4-methyl-7,8-dihydro-6H-quinazolin-5-one oxime, compound 66, (100 mg, 0.290 mmol), 1-(3-chloro-propyl)-4-methyl-piperazine dihydrochloride (87 mg, 0.348 mmol) and sodium hydride (60% dispersion in oil) (52 mg, 1.31 mmol), following the same procedure used for 2-amino-7-(4-fluoro-biphenyl-2-yl)-4-methyl-7,8-dihydro-6H-quinazolin-5-one O-(3-dimethylamino-propyl)-oxime (compound 88), except after addition of water the solvent was removed under reduced pressure. The crude material was taken up in ethylacetate (20 ml) and the resulting solution was filtered. The solvent was removed under reduced pressure and the title compound was purified by column chromatography eluting with dichloromethane/methanol (90/10).

Yield=25.8 mg (18%)

Mass spectrum (ES-MS (+ve)) 485 [MH]$^+$, Retention time 2.84 min, 95% UV.

1H NMR (250 MHz, CHLOROFORM-d) δ ppm 7.28-7.46 (7H, m), 7.20-7.26 (2H, m), 5.07 (2H, br. s), 4.14 (2H, t), 3.16-3.25 (2H, m), 3.09-3.15 (3H, m), 2.98-3.04 (4H, m), 2.87-2.95 (1H, m), 2.80-2.86 (1H, m), 2.70-2.77 (1H, m), 2.62-2.68 (4H, m), 2.65 (3H, s), 2.55-2.58 (1H, m), 2.57 (3H, s), 1.90-2.04 (2H, m).

Stage 3: 2-Amino-7-biphenyl-2-yl-4-methyl-7,8-dihydro-6H-quinazolin-5-one O-(2-(4-methyl-piperazin-1-yl)-ethyl)-oxime (Compound 76)

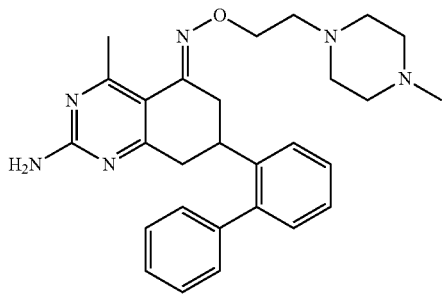

The title compound was prepared from 2-amino-7-biphenyl-2-yl-4-methyl-7,8-dihydro-6H-quinazolin-5-one oxime, compound 66, (100 mg, 0.290 mmol), 1-(2-chloro-ethyl)-4-methyl-piperazine dihydrochloride (82 mg, 0.348 mmol) and sodium hydride (60% dispersion in oil) (52 mg, 1.31 mmol), following the same procedure used for 2-amino-7-(4-fluoro-biphenyl-2-yl)-4-methyl-7,8-dihydro-6H-quinazolin-5-one O-(3-dimethylamino-propyl)-oxime (compound 88), except after addition of water the solvent was removed under reduced pressure. The crude material was taken up in ethylacetate (20 ml) and the resulting solution was filtered. The solvent was removed under reduced pressure and the title compound was purified by column chromatography eluting with dichloromethane/methanol (90/10).

Yield=4.8 mg (3.5%)

Mass spectrum (ES-MS (+ve)) 471 [MH]$^+$, Retention time 2.85 min, 96% UV.

1H NMR (250 MHz CHLOROFORM-d) δ ppm 7.28-7.46 (7H, m), 7.20-7.26 (2H, m), 5.08 (2H, br. s), 4.26 (2H, t), 3.09-3.26 (2H, m), 2.92 (1H, t), 2.79-2.82 (1H, m), 2.73 (2H, t), 2.49-2.67 (9H, m), 2.58 (3H, s), 2.35 (3H, s).

Stage 3: 2-Amino-7-biphenyl-2-yl-4-methyl-7,8-dihydro-6H-quinazolin-5-one O-(3-dimethylamino-propyl)-oxime (Compound 77)

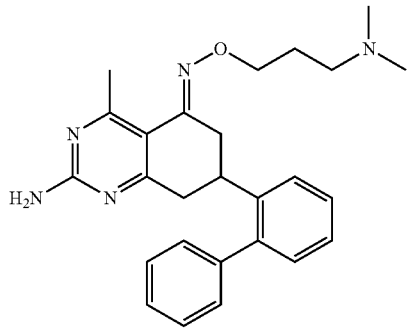 [SMILES: Cc1nc(N)nc2c1/C(=N/OCCCN(C)C)CC(c1ccccc1-c1ccccc1)C2]

The title compound was prepared from 2-amino-7-biphenyl-2-yl-4-methyl-7,8-dihydro-6H-quinazolin-5-one oxime, compound 66, (30 mg, 0.087 mmol), 3-dimethyl-aminopropyl chloride hydrochloride (16 mg, 0.105 μmol) and sodium hydride (60% dispersion in oil) (11 mg, 0.278 mmol), following the same procedure used for 2-amino-7-(4-fluoro-biphenyl-2-yl)-4-methyl-7,8-dihydro-6H-quinazolin-5-one O-(3-dimethylamino-propyl)-oxime (compound 88).

Yield=26 mg (71%)

Mass spectrum (ES-MS (+ve)) 430 [MH]$^+$, Retention time 2.98 min, 88% UV.

1H NMR (360 MHz, DMSO-d$_6$) δ ppm 7.59 (1H, d), 7.23-7.45 (7H, m), 7.17 (1H, d), 6.79 (2H, s), 4.04 (2H, t), 2.93-3.08 (3H, m), 2.53-2.65 (2H, m), 2.44 (3H, s), 2.23 (2H, t), 2.09 (6H, s), 1.66-1.80 (2H, m).

Stage 3: 2-Amino-7-biphenyl-2-yl-4-methyl-7,8-dihydro-6H-quinazolin-5-one O-(2-pyrrolidin-1-yl-ethyl)-oxime (Compound 78)

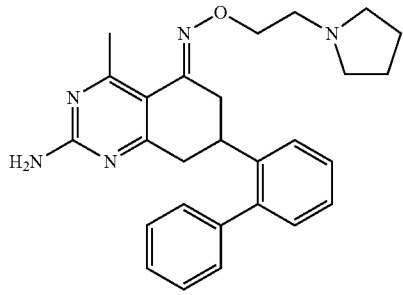 [SMILES: Cc1nc(N)nc2c1/C(=N/OCCN1CCCC1)CC(c1ccccc1-c1ccccc1)C2]

The title compound was prepared from 2-amino-7-biphenyl-2-yl-4-methyl-7,8-dihydro-6H-quinazolin-5-one oxime, compound 66, (30 mg, 0.087 mmol), N-(2-chloroethyl)-pyrrolidine hydrochloride (30 mg, 0.176 mmol) and sodium hydride (60% dispersion in oil) (18 mg, 0.470 mmol), following the same procedure used for 2-amino-7-(4-fluoro-biphenyl-2-yl)-4-methyl-7,8-dihydro-6H-quinazolin-5-one O-(3-dimethylamino-propyl)-oxime (compound 88).

Mass spectrum (ES-MS (+ve)) 442 [MH]$^+$, Retention time 3.03 min, 91% UV.

1H NMR (360 MHz, DMSO-$d_6$) δ ppm 7.59 (1H, d), 7.23-7.43 (7H, m), 7.17 (1H, d), 6.80 (2H, br. s), 4.12 (2H, t), 2.96-3.10 (3H, m), 2.53-2.69 (4H, m), 2.40-2.46 (7H, m), 1.60-1.68 (4H, m).

Stage 3: 2-Amino-7-biphenyl-2-yl-4-methyl-7,8-dihydro-6H-quinazolin-5-one O-(2-morpholin-4-yl-ethyl)-oxime (Compound 79)

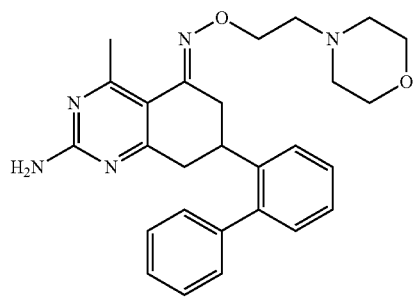 [SMILES: Cc1nc(N)nc2c1/C(=N/OCCN1CCOCC1)CC(c1ccccc1-c1ccccc1)C2]

The title compound was prepared from 2-amino-7-biphenyl-2-yl-4-methyl-7,8-dihydro-6H-quinazolin-5-one oxime, compound 66, (30 mg, 0.087 mmol), 2-(chloro-ethyl)-morpholine hydrochloride (32 mg, 0.214 mmol) and sodium hydride (60% dispersion in oil) (18 mg, 0.470 mmol), following the same procedure used for 2-amino-7-(4-fluoro-biphenyl-2-yl)-4-methyl-7,8-dihydro-6H-quinazolin-5-one O-(3-dimethylamino-propyl)-oxime (compound 88).

Mass spectrum (ES-MS (+ve)) 458 [MH]$^+$, Retention time 2.98 min, 97% UV.

1H NMR (360 MHz, DMSO-$d_6$) δ ppm 7.58 (1H, d), 7.23-7.43 (7H, m), 7.17 (1H, d), 4.14 (2H, t), 3.50-3.57 (4H, m), 2.93-3.07 (3H, m), 2.57 (4H, t), 2.44 (3H, s), 2.35-2.41 (4H, m).

Stage 3: 2-Amino-7-biphenyl-2-yl-4-methyl-7,8-dihydro-6H-quinazolin-5-one O-(2-diethylamino-ethyl)-oxime (Compound 80)

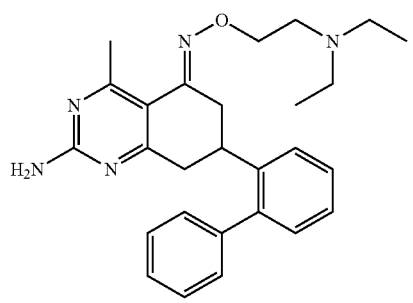 [SMILES: CCN(CC)CCO/N=C1\CC(c2ccccc2-c2ccccc2)Cc2nc(N)nc(C)c21]

The title compound was prepared from 2-amino-7-biphenyl-2-yl-4-methyl-7,8-dihydro-6H-quinazolin-5-one oxime, compound 66, (30 mg, 0.087 mmol), 2-diethylaminoethyl-chloride hydrochloride (30 mg, 0.221 mmol) and sodium hydride (60% dispersion in oil) (18 mg, 0.470 mmol) following the same procedure used for 2-amino-7-(4-fluoro-biphenyl-2-yl)-4-methyl-7,8-dihydro-6H-quinazolin-5-one O-(3-dimethylamino-propyl)-oxime (compound 88).

Mass spectrum (ES-MS (+ve)) 444 [MH]$^+$, Retention time 3.04 min, 100% UV.

1H NMR (360 MHz, DMSO-$d_6$) δ ppm 7.58 (1H, d), 7.22-7.44 (7H, m), 7.16 (1H, d), 6.80 (2H, s), 4.06 (2H, t), 2.91-3.11 (3H, m), 2.53-2.69 (4H, m), 2.43-2.48 (7H, m), 0.90 (6H, t).

Stage 3: 2-Amino-7-biphenyl-2-yl-4-methyl-7,8-dihydro-6H-quinazolin-5-one O-(2-dimethylamino-ethyl)-oxime (Compound 81)

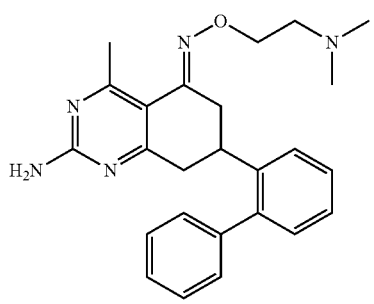 [SMILES: Cc1nc(N)nc2c1/C(=N/OCCN(C)C)CC(c1ccccc1-c1ccccc1)C2]

The title compound was prepared from 2-amino-7-biphenyl-2-yl-4-methyl-7,8-dihydro-6H-quinazolin-5-one oxime, compound 66, (50 mg, 0.145 mmol), 2-dimethylaminoethyl-chloride hydrochloride (25 mg, 0.174 mmol) and sodium hydride (60% dispersion in oil) (18 mg, 0.465 mmol) following the same procedure used for 2-amino-7-(4-fluoro-biphenyl-2-yl)-4-methyl-7,8-dihydro-6H-quinazolin-5-one O-(3-dimethylamino-propyl)-oxime (compound 88).

Yield=34 mg (56%)

Mass spectrum (ES-MS (+ve)) 416 [MH]$^+$, Retention time 2.93 min, 94% UV.

1H NMR (250 MHz, DMSO-$d_6$) δ ppm 7.59 (1H, d), 7.12-7.45 (8H, m), 6.80 (2H, s), 4.10 (2H, t), 2.94-3.09 (4H, m), 2.55-2.66 (3H, m), 2.44 (3H, s), 2.14 (6H, s).

Stage 3: 2-Amino-7-biphenyl-2-yl-4-methyl-7,8-dihydro-6H-quinazolin-5-one O-(3-piperazin-1-yl-propyl)-oxime (Compound 82)

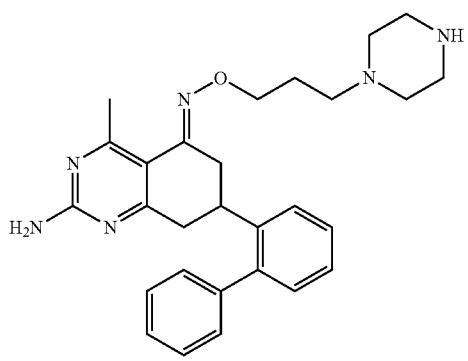 [SMILES: Cc1nc(N)nc2c1/C(=N/OCCCN1CCNCC1)CC(c1ccccc1-c1ccccc1)C2]

The title compound was prepared from 2-amino-7-biphenyl-2-yl-4-methyl-7,8-dihydro-6H-quinazolin-5-one oxime, compound 66, (100 mg, 0.290 mmol), 1-(3-chloro-propyl)-piperazine dihydrochloride (82 mg, 0.350 mmol) and sodium hydride (60% dispersion in oil) (18 mg, 465 mmol), following the same procedure used for 2-amino-7-(4-fluoro-biphenyl-2-yl)-4-methyl-7,8-dihydro-6H-quinazolin-5-one O-(3-dimethylamino-propyl)-oxime (compound 88), except after addition of water the solvent was removed under reduced pressure. The crude material was taken up in methanol (20 ml) and the resulting solution was filtered. The solvent was removed under reduced pressure. The title compound was purified by preparative HPLC (UV directed fraction collection).

Yield=22.6 mg (16%)

Mass spectrum (ES-MS (+ve)) 471 [MH]$^+$, Retention time 2.65 min, 99% UV.

1H NMR (500 MHz, MeOD-d$_4$) δ ppm 7.52 (1H, d), 7.39-7.46 (3H, m), 7.35 (2H, t), 7.28 (2H, d), 7.24 (1H, d), 4.27 (2H, td), 3.44 (4H, t), 3.12-3.26 (7H, m), 3.01 (2H, t), 2.84-2.92 (1H, m), 2.71 (3H, s), 2.70-2.74 (1H, m), 2.05-2.13 (2H, m).

Stage 3: 2-Amino-7-biphenyl-2-yl-4-methyl-7,8-dihydro-6H-quinazolin-5-one O-hex-5-ynyl-oxime (Compound 83)

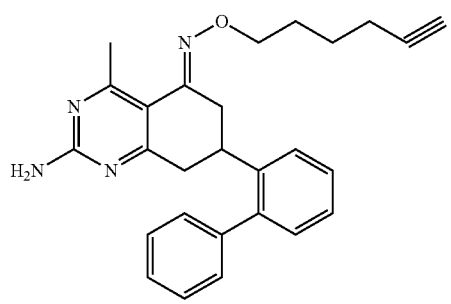 [SMILES: C#CCCCCO/N=C1\CC(c2ccccc2-c2ccccc2)Cc2nc(N)nc(C)c21]

The title compound was prepared from 2-amino-7-biphenyl-2-yl-4-methyl-7,8-dihydro-6H-quinazolin-5-one oxime, compound 66, (50 mg, 0.145 mmol), 6-chloro-1-hexyne (21 μl, 0.174 mmol) and sodium hydride (60% dispersion in oil) (11 mg, 0.465 mmol), following the same procedure used for 2-amino-7-(4-fluoro-biphenyl-2-yl)-4-methyl-7,8-dihydro-6H-quinazolin-5-one O-(3-dimethylamino-propyl)-oxime (compound 88), except after addition of water the solvent was removed under reduced pressure. The crude material was taken up in methanol (20 ml) and the resulting solution was filtered. The solvent was removed under reduced pressure. The title compound was purified by preparative HPLC (mass directed fraction collection).

Mass spectrum (ES-MS (+ve)) 425 [MH]$^+$, Retention time 4.93 min, 100% UV.

1H NMR (250 MHz, MeOD-d$_4$) δ ppm 7.20-7.48 (9H, m), 4.18 (2H, t), 3.14-3.24 (3H, m), 2.83-2.88 (1H, m), 2.69 (3H, s), 2.54-2.68 (1H, m), 2.20-2.24 (2H, m), 2.22 (1H, s), 1.79-1.84 (2H, m), 1.55-1.61 (2H, m).

b. 2-Amino-4-methyl-7-(2-pyridin-3-yl-phenyl)-7,8-dihydro-6H-quinazolin-5-one oxime (Compound 84)

Stage 1: 2-Amino-4-methyl-7-(2-pyridin-3-yl-phenyl)-7,8-dihydro-6H-quinazolin-5-one

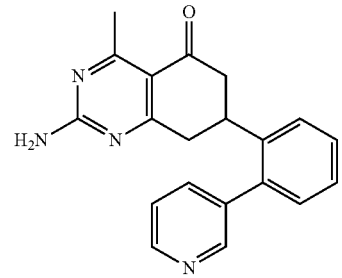 [SMILES: Cc1nc(N)nc2c1C(=O)CC(c1ccccc1-c1cccnc1)C2]

The title compound was prepared from 2-amino-4-methyl-7-(2-bromo-phenyl)-4-methyl-7,8-dihydro-6H-quinazolin-5-one (example 3/i stage 2/3) and pyridin-3-ylboronic acid, following the procedure describing the synthesis of 2-amino-7-biphenyl-2-yl-4-methyl-7,8-dihydro-6H-quinazolin-5-one (example 5/a stage 1).

Mass spectrum data: (ES-MS (+ve)) 331 [MH]$^+$, Retention time 2.76 min, 100% UV.

1H NMR (360 MHz, DMSO-d$_6$) δ ppm 8.62 (2H, d), 7.67 (1H, d), 7.47-7.53 (1H, m), 7.43 (2H, s), 7.34-7.40 (3H, m), 7.22 (1H, dd), 3.31-3.35 (1H, m), 3.13-3.23 (1H, m), 2.95 (1H, dd), 2.66-2.76 (1H, m), 2.51 (3H, s), 2.45-2.50 (1H, m).

Stage 2: 2-Amino-4-methyl-7-(2-pyridin-3-yl-phenyl)-7,8-dihydro-6H-quinazolin-5-one oxime (Compound 84)

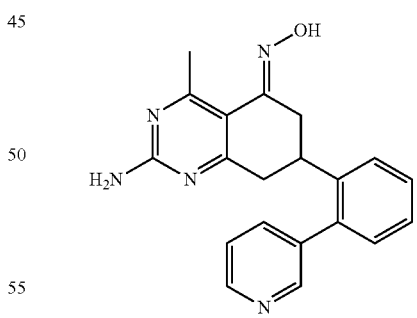

The title compound was prepared from 2-amino-4-methyl-7-(2-pyridin-3-yl-phenyl)-7,8-dihydro-6H-quinazolin-5-one from stage 1, following the procedure describing the synthesis of 2-amino-7-biphenyl-2-yl-4-methyl-7,8-dihydro-6H-quinazolin-5-one oxime (example 5/a stage 2—method A).

Mass spectrum (ES-MS (+ve)) 346 [MH]$^+$, Retention time 2.55 min, 99% UV.

1H NMR (250 MHz, DMSO-d$_6$) δ ppm 10.93 (1H, s), 8.46-8.56 (2H, m), 7.72 (1H, d), 7.62 (1H, d), 7.39-7.50 (2H, m), 7.33 (1H, t), 7.20 (1H, d), 6.68 (2H, br. s), 2.81-3.12 (4H, m), 2.56 (1H, d), 2.43 (3H, s).

c. 2-Amino-4-methyl-7-(2-pyridin-4-yl-phenyl)-7,8-dihydro-6H-quinazolin-5-one oxime (Compound 85)

Stage 1: 2-Amino-4-methyl-7-(2-pyridin-4-yl-phenyl)-7,8-dihydro-6H-quinazolin-5-one

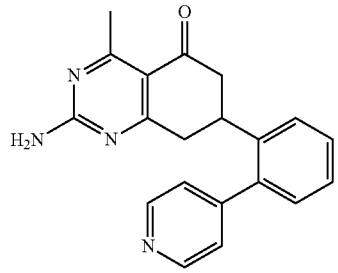 [SMILES: Cc1nc(N)nc2c1C(=O)CC(c1ccccc1-c1ccncc1)C2]

The title compound was prepared from 2-amino-4-methyl-7-(2-bromo-phenyl), 4-methyl-7,8-dihydro-6H-quinazolin-5-one (example 3/i) and pyridin-4-yl-boronic acid, following the procedure describing the synthesis of 2-amino-7-biphenyl-2-yl-4-methyl-7,8-dihydro-6H-quinazolin-5-one (example 5/a stage 1).

Mass spectrum (ES-MS (+ve)) 331 [MH]$^+$, Retention time 2.63 min, 100% UV.

1H NMR (360 MHz, DMSO-d$_6$) δ ppm 8.51-8.61 (2H, m), 7.75-7.83 (1H, m), 7.67 (1H, d), 7.33-7.53 (5H, m), 7.20-7.28 (1H, m), 3.27-3.35 (1H, m), 3.11-3.23 (1H, m), 2.95 (1H, dd), 2.65-2.78 (1H, m), 2.51 (3H, s), 2.47-2.50 (1H, m).

Stage 2: 2-Amino-4-methyl-7-(2-pyridin-4-yl-phenyl)-7,8-dihydro-6H-quinazolin-5-one oxime (Compound 85)

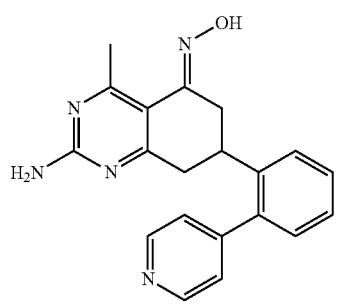

The title compound was prepared from 2-amino-4-methyl-7-(2-pyridin-4-yl-phenyl)-7,8-dihydro-6H-quinazolin-5-one from stage 1, following the procedure describing the synthesis of 2-amino-7-biphenyl-2-yl-4-methyl-7,8-dihydro-6H-quinazolin-5-one oxime (example 5/a stage 2—method A).

Mass spectrum (ES-MS (+ve)) 346 [MH]$^+$, Retention time 2.45 min, 100% UV.

1H NMR (250 MHz, DMSO-d$_6$) δ ppm 10.93 (1H, s), 8.57 (2H, d), 7.58-7.69 (1H, m), 7.46 (1H, t), 7.30-7.38 (3H, m), 7.18 (1H, d), 6.67 (2H, s), 2.86-3.12 (4H, m), 2.56 (1H, d), 2.43 (3H, s).

d. 2-Amino-4-methyl-7-(2-pyridin-2-yl-phenyl)-7,8-dihydro-6H-quinazolin-5-one oxime (Compound 86)

Stage 1: 2-Amino-4-methyl-7-(2-pyridin-2-yl-phenyl)-7,8-dihydro-6H-quinazolin-5-one

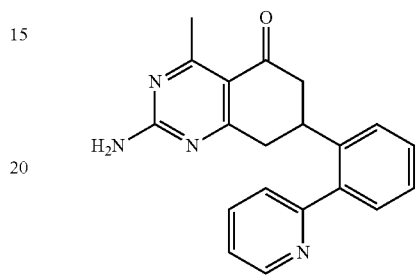

The title compound was prepared from 2-amino-4-methyl-7-(2-bromo-phenyl)-4-methyl-7,8-dihydro-6H-quinazolin-5-one (example 3/i stage 2/3) and pyridin-2-ylboronic acid, following the procedure describing the synthesis of 2-amino-7-biphenyl-2-yl-4-methyl-7,8-dihydro-6H-quinazolin-5-one (example 5/a stage 1).

Mass spectrum (ES-MS (+ve)) 331 [MH], Retention time 2.89 min, 98% UV.

1H NMR (250 MHz, DMSO-d$_6$) δ ppm 8.54-8.65 (1H, m), 7.81-7.95 (1H, m), 7.56-7.65 (1H, m), 7.27-7.54 (7H, m), 3.51-3.73 (1H, m), 3.04-3.24 (1H, m), 2.71-3.00 (2H, m), 2.53-2.59 (1H, m), 2.40-2.58 (3H, s).

Stage 2: 2-Amino-4-methyl-7-(2-pyridin-2-yl-phenyl)-7,8-dihydro-6H-quinazolin-5-one oxime (Compound 86)

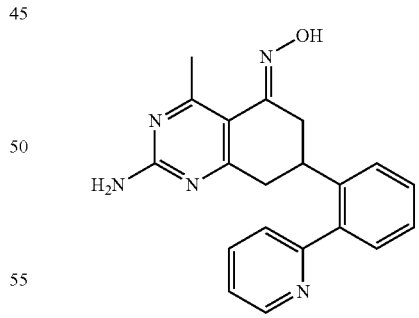

The title compound was prepared from 2-amino-4-methyl-7-(2-pyridin-2-yl-phenyl)-7,8-dihydro-6H-quinazolin-5-one from stage 1, following the procedure describing the synthesis of 2-amino-7-biphenyl-2-yl-4-methyl-7,8-dihydro-6H-quinazolin-5-one oxime (example 5/a stage 2—method A).

Mass spectrum (ES-MS (+ve)) 346 [MH]$^+$, Retention time 2.61 min, 94% UV.

1H NMR (360 MHz, DMSO-d$_6$) δ ppm 8.60 (1H, d), 7.82-7.93 (1H, m), 7.62 (1H, d), 7.44-7.52 (2H, m), 7.29-7.39

(3H, m), 6.70 (2H, s), 3.10-3.27 (3H, m), 2.97 (1H, dd), 2.57-2.72 (1H, m), 2.47 (3H, s).

e. 2-Amino-7-(5-fluoro-biphenyl-2-yl)-4-methyl-7,8-dihydro-6H-quinazolin-5-one oxime and 2-amino-7-(4-fluoro-biphenyl-2-yl)-4-methyl-7,8-dihydro-6H-quinazolin-5-one O-(3-dimethylamino-propyl)-oxime (Compounds 87 and 88)

Preparation of the 2-amino-7-(2-bromo-4-fluoro-phenyl-2-yl)-4-methyl-7,8-dihydro-6H-quinazolin-5-one Scheme 6

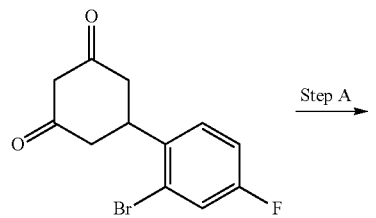

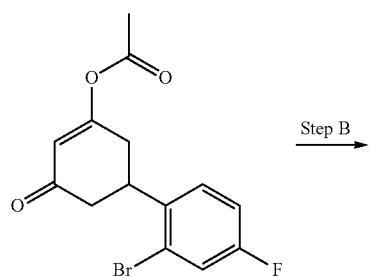

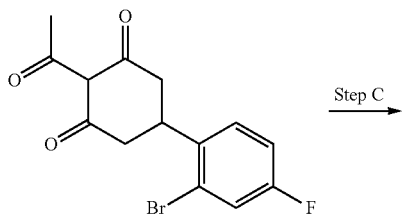

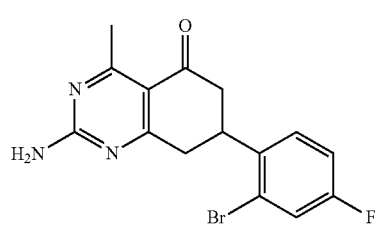

The 2-amino-7-(2-bromo-4-fluoro-phenyl-2-yl)-4-methyl-7,8-dihydro-6H-quinazolin-5-one precursor was prepared following the amended procedure described in scheme 6.

Step A: Acetic acid 5-(2-bromo-4-fluoro-phenyl)-3-oxo-cyclohex-1-enyl ester

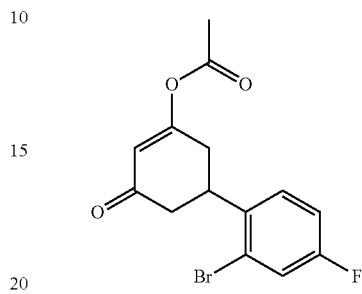

The title compound was prepared reacting 5-(2-bromo-4-fluoro-phenyl)-cyclohexane-1,3-dione (example 1/f stage 2) (5 g, 17.4 mmol) and sodium acetate (1.42 g, 17.4 mmol) in neat acetic anhydride (30 ml). The reaction mixture was heated for 2 h at 100° C. and allowed to cool to ambient temperature whereupon water (60 ml) was added. The mixture was extracted with EtOAc (2×80 ml) and the combined organic layers washed with sat aq sodium bicarbonate until the pH was neutral. Then the organics were dried over sodium sulphate, filtered, and the solvent removed in vacuo.

The isolated compound was used without any further purification.

Yield: 5.7 g (100%)

Mass spectrum (ES-MS (+ve)) no[MH]$^+$, Retention time 2.05 min, 85% UV.

1H NMR (500 MHz, CHLOROFORM-d) δ ppm 7.36 (1H, dd), 7.28 (1H, dd), 7.07 (1H, td), 6.05 (1H, s), 3.84-3.94 (1H, m), 2.74-2.81 (2H, m), 2.66-2.75 (1H, m), 2.58-2.66 (1H, m), 2.24 (3H, s).

Step B: 2-Acetyl-5-(2-bromo-4-fluoro-phenyl)-cyclohexane-1,3-dione

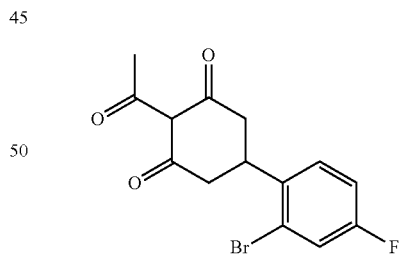

The title compound was prepared by reacting acetic acid 5-(2-bromo-4-fluoro-phenyl)-3-oxo-cyclohex-1-enyl ester (162 mg, 0.49 mmol) from step A, with potassium cyanide (6.5 mg, 0.10 mmol) and triethylamine (77 µl) in acetonitrile (3 ml). The reaction mixture was stirred for 12 h at ambient temperature. The acetonitrile was then removed in vacuo, the crude product taken up in EtOAc (5 ml) then washed with 1M HCl (10 ml) [care: HCN likely to be generated], followed by water (2×10 ml) and brine (10 ml). The organics were then dried over sodium sulphate, filtered, and the solvent removed in vacuo. The isolated compound was used without any further purification.

Yield: 114 mg (70%)

Mass spectrum (ES-MS (+ve)) 328 [MH]+, Retention time 2.19 min, 93% UV.

1H NMR (250 MHz, CHLOROFORM-d) δ ppm 7.28 (1H, dd), 7.13 (1H, dd), 6.99 (1H, dd), 3.62-3.80 (1H, m), 2.81-2.95 (1H, m), 2.63-2.80 (2H, m), 2.58 (3H, s), 2.46-2.55 (1H, m).

Step C: 2-amino-7-(2-bromo-4-fluoro-phenyl-2-yl)-4-methyl-7,8-dihydro-6H-quinazolin-5-one

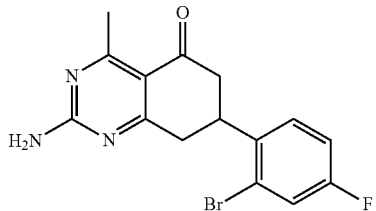 [SMILES: Cc1nc(N)nc2c1C(=O)CC(c1ccc(F)cc1Br)C2]

To a stirred solution of 2-acetyl-5-(2-bromo-4-fluoro-phenyl)-cyclohexane-1,3-dione (4.5 g, 13.8 mmol) from step B, in chloroform (130 ml) was added pyrrolidine (1.36 ml, 16.6 mmol). The reaction mixture was stirred at ambient temperature and monitored by TLC. The reaction mixture was concentrated to dryness under reduced pressure. To a stirred solution of this solid in 1,4-dioxane (200 ml) was added guanidine carbonate (8.9 g, 55 mmol). The mixture was heated at 10° C. and stirred for 16 h. The excess of guanidine carbonate was removed by filtration and the solvent was evaporated under reduced pressure. Water (50 ml) was added and the resulting precipitate was filtered, washed with water followed by heptane and air dried.

Yield: 1.78 g (37%)

Mass spectrum (ES-MS (+ve)) 351 [MH]+, Retention time 1.82 min, 87% UV.

1H NMR (250 MHz, DMSO-d$_6$) δ ppm 7.61 (1H, dd), 7.53 (1H, dd), 7.31 (1H, dd), 3.59-3.78 (1H, m), 3.12 (1H, dd), 2.77-2.97 (2H, m), 2.60-2.69 (1H, m).

Stage 1: 2-Amino-7-(4-fluoro-biphenyl-2-yl)-4-methyl-7,8-dihydro-6H-quinazolin-5-one

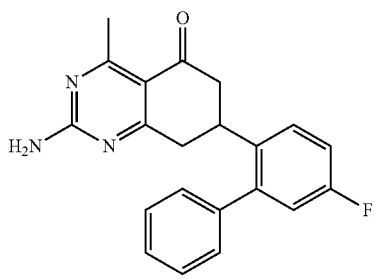 [SMILES: Cc1nc(N)nc2c1C(=O)CC(c1ccc(F)cc1-c1ccccc1)C2]

To a solution of 2-amino-7-(2-bromo-4-fluoro-phenyl-2yl)-4-methyl-7,8-dihydro-6H-quinazolin-5-one (500 mg, 1.43 mmol) from step C, tetrakis(triphenylphosphine)palladium (83 mg, 5 mol %) and potassium carbonate (493 mg, 3.57 mmol) in degassed toluene:ethanol (2:1, 10 ml) was added phenylboronic acid (21 mg, 0.171 mmol). The reaction mixture was heated in a microwave at 150° C. for 30 min. The reaction mixture was filtered through celite and the cake washed with methanol. The solvent was removed under reduced pressure. The title compound was purified by column chromatography using ethyl acetate/heptane (1/1).

Yield: 16 mg (32%)

Mass spectrum (ES-MS (+ve)) 347 [MH]+, Retention time 1.99 min, 100% UV.

1H NMR (500 MHz, MeOD-d$_4$) δ ppm 7.45 (1H, dd), 7.28-7.34 (2H, m), 7.23-7.28 (1H, m), 7.14-7.20 (2H, m), 7.01-7.08 (1H, m), 0.85 (1H, dd), 3.29-3.41 (1H, m), 2.97-3.08 (1H, m), 2.67-2.82 (2H, m), 2.43-2.50 (4H, m).

Stage 2: 2-Amino-7-(5-fluoro-biphenyl-2-yl)-4-methyl-7,8-dihydro-6H-quinazolin-5-one oxime (Compound 87)

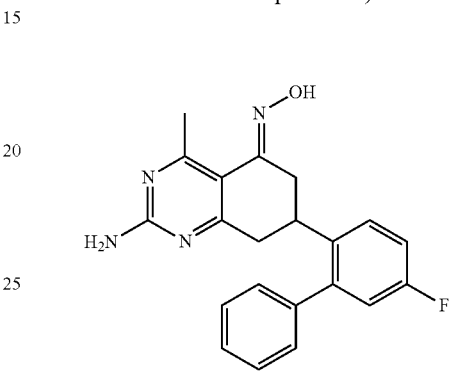

The title compound was prepared from 2-amino-7-(4-fluoro-biphenyl-2-yl)-4-methyl-7,8-dihydro-6H-quinazolin-5-one (16 mg, 0.046 mmol) from stage 1, following the procedure describing the synthesis of 2-amino-7-biphenyl-2-yl-4-methyl-7,8-dihydro-6H-quinazolin-5-one oxime (example 5/a stage 2—method A).

Mass spectrum (ES-MS (+ve)) 363 [MH]+, Retention time 3.68 min, 99% UV.

1H NMR (500 MHz, DMSO-d$_6$) δ ppm 10.95 (1H, s), 7.64 (1H, dd), 7.39-7.46 (2H, m), 7.33-7.37 (1H, m), 7.22-7.31 (3H, m), 7.00 (1H, dd), 6.72 (2H, br. s), 2.89-3.08 (3H, m), 2.52-2.58 (2H, m), 2.44 (3H, s).

Stage 3: 2-Amino-7-(4-fluoro-biphenyl-2-yl)-4-methyl-7,8-dihydro-6H-quinazolin-5-one O-(3-dimethylamino-propyl)-oxime (Compound 88)

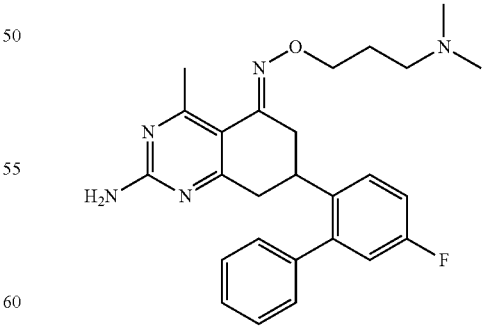

In a seal tube a stirred solution of 2-amino-7-(5-fluoro-biphenyl-2-yl)-4-methyl-7,8-dihydro-6H-quinazolin-5-one oxime, compound 87, (100 mg, 0.276 mmol) in DMF (4 ml) had 3-dimethyl-aminopropyl chloride hydrochloride (52.6 mg, 0.331 mmol), and sodium hydride (60% dispersion in oil)

(35.3 mg, 0.883 mmol) added. The reaction mixture was stirred at ambient temperature for 5 min and then heated at 80° C. for 17 h. The reaction mixture was cooled to ambient temperature and quenched with water (4 ml). The title compound precipitated out and was filtered and washed with water.

Yield: 70.3 mg (57%)

Mass spectrum (ES-MS (+ve)) 448 [MH]$^+$, Retention time 3.07 min, 93% UV.

1H NMR (500 MHz, DMSO-d$_6$) δ ppm 7.64 (1H, dd), 7.33-7.45 (3H, m), 7.22-7.32 (3H, m), 7.00 (1H, dd), 6.77 (2H, br. s), 4.04 (2H, t), 2.90-3.05 (3H, m), 2.53-2.66 (2H, m), 2.44 (3H, s), 2.22 (2H, t), 2.09 (6H, s), 1.73 (2H, quin).

f. 2-Amino-7-(4-fluoro-2-pyridin-3-yl-phenyl)-4-methyl-7,8-dihydro-6H-quinazolin-5-one oxime and 2-amino-7-(4-fluoro-2-pyridin-3-yl-phenyl)-4-methyl-7,8-dihydro-6H-quinazolin-5-one O-(3-dimethylamino-propyl)-oxime (Compounds 89 and 90

Stage 1: 2-Amino-7-(4-fluoro-2-pyridin-3-yl-phenyl)-4-methyl-7,8-dihydro-6H-quinazolin-5-one

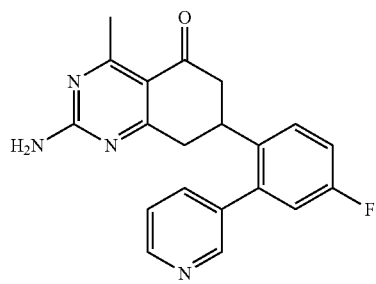 [SMILES: Cc1nc(N)nc2c1C(=O)CC(c1ccc(F)cc1-c1cccnc1)C2]

The title compound was prepared from 2-amino-7-(2-bromo-4-fluoro-phenyl-2-yl)-4-methyl-7,8-dihydro-6H-quinazolin-5-one (example 5/e step c) (500 mg, 1.43 mmol) and pyridine-3-boronic acid (211 mg, 1.71 mmol) following the same procedure describing the synthesis of 2-amino-7-biphenyl-2-yl-4-methyl-7,8-dihydro-6H-quinazolin-5-one (example 5/a stage 1).

Mass spectrum (ES-MS (+ve)) 348 [MH]$^+$, Retention time 1.34 min, 99% UV.

1H NMR (500 MHz, MeOD-d$_4$) δ ppm 8.49-8.61 (2H, m), 7.84 (1H, d), 7.58-7.69 (1H, m), 7.48-7.55 (1H, m), 7.20-7.28 (1H, m), 7.00-7.09 (1H, m), 3.35-3.42 (1H, m), 3.11-3.21 (1H, m), 2.81-2.97 (2H, m), 2.54-2.64 (4H, m).

Stage 2: 2-Amino-7-(4-fluoro-2-pyridin-3-yl-phenyl)-4-methyl-7,8-dihydro-6H-quinazolin-5-one oxime (Compound 89)

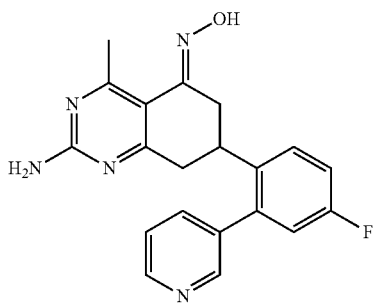 [SMILES: Cc1nc(N)nc2c1/C(=N/O)CC(c1ccc(F)cc1-c1cccnc1)C2]

The title compound was prepared from 2-amino-7-(4-fluoro-biphenyl-2-yl)-4-methyl-7,8-dihydro-6H-quinazolin-5-one (16 mg, 0.046 mmol) stage 1, following the procedure describing the synthesis of 2-amino-7-biphenyl-2-yl-4-methyl-7,8-dihydro-6H-quinazolin-5-one oxime (example 5/a stage 2—method A).

Yield: 250 mg (73%)

Mass spectrum (ES-MS (+ve)) 364 [MH]$^+$, Retention time 2.64 min, 94% UV.

1H NMR (500 MHz, DMSO-d$_6$) δ ppm 10.98 (1H, s), 8.58 (1H, dd), 8.54 (1H, s), 7.79 (1H, d), 7.68 (1H, dd), 7.47 (1H, dd), 7.32 (1H, td), 7.11 (1H, dd), 6.77 (2H, br. s), 2.96-3.10 (2H, m), 2.82-2.91 (1H, m), 2.52-2.62 (2H, m), 2.45 (3H, s).

Stage 3: 2-Amino-7-(4-fluoro-2-pyridin-3-yl-phenyl)-4-methyl-7,8-dihydro-6H-quinazolin-5-one O-(3-dimethylamino-propyl)-oxime (Compound 90)

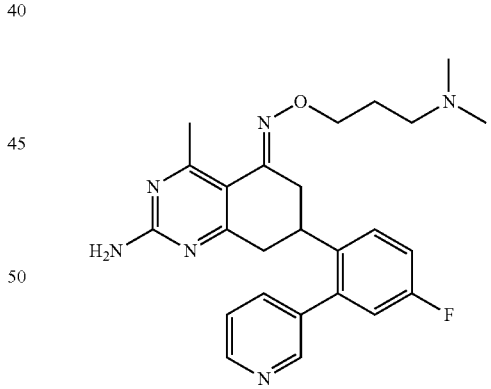

The title compound was prepared from 2-amino-7-(4-fluoro-2-pyridin-3-yl-phenyl)-4-methyl-7,8-dihydro-6H-quinazolin-5-one oxime, compound 89, (100 mg, 0.275 mmol), 3-dimethyl-aminopropyl chloride hydrochloride (52 mg, 0.330 mmol) and sodium hydride (60% dispersion in oil) (35 mg, 0.881 mmol) following the same procedure used for 2-amino-7-(4-fluoro-biphenyl-2-yl)-4-methyl-7,8-dihydro-6H-quinazolin-5-one O-(3-dimethylamino-propyl)-oxime (compound 88) except after addition of water the solvent was removed under reduced pressure. The crude material was then extracted with ethyl acetate (20 ml), filtered and the resulting organic phase was concentrated under reduced pressure. The resulting material was washed with diethyl ether yielding the title compound.

Yield=84.5 mg (69%)

Mass spectrum (ES-MS (+ve)) 449 [MH]+, Retention time 2.47 min, 90% UV.

1H NMR (500 MHz, DMSO-d6) δ ppm 8.59 (1H, d), 8.53 (1H, s), 7.77 (1H, d), 7.68 (1H, dd), 7.45 (1H, dd), 7.32 (1H, td), 7.11 (1H, dd), 6.79 (2H, br. s), 4.06 (2H, t), 2.96-3.09 (2H, m), 2.84-2.94 (1H, m), 2.55-2.65 (3H, m), 2.45 (4H, s), 2.25 (6H, br.s), 1.75-1.84 (2H, m).

g. 2-Amino-7-[2-(1H-indol-4-10)-phenyl]-4-methyl-7,8-dihydro-6H-quinazolin-5-one

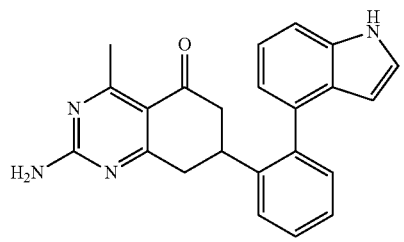 [SMILES: Cc1nc(N)nc2c1C(=O)CC(c1ccccc1-c1cccc3[nH]ccc13)C2]

The title compound was prepared from 2-amino-7-(2-bromo-phenyl)-4-methyl-7,8-dihydro-6H-quinazolin-5-one (example 3/i stage 2/3), following the procedure describing the synthesis of 2-amino-7-biphenyl-2-yl-4-methyl-7,8-dihydro-6H-quinazolin-5-one (example 5/a stage 1) using 4-boronic acid-1H-indole instead of phenyl-boronic acid.

Mass spectrum (ES-MS (+ve)) 369 [MH]+, Retention time 3.97 min, 99% UV.

1H NMR (250 MHz, DMSO-d6) δ ppm 11.22 (1H, br.s), 7.63 (1H, dd), 7.26-7.51 (6H, m), 7.17-7.24 (1H, m), 7.05-7.16 (1H, m), 6.83 (1H, d), 5.97 (1H, br. s), 2.53-3.29 (5H, m), 2.43 (3H, s).

h. 2-Amino-7-[2-(1H-indol-7-yl)-phenyl]-4-methyl-7,8-dihydro-6H-quinazolin-5-one

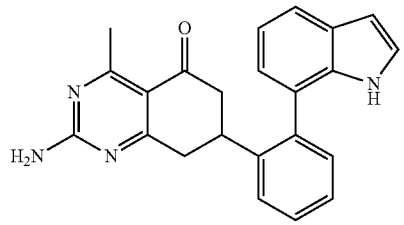 [SMILES: Cc1nc(N)nc2c1C(=O)CC(c1ccccc1-c1cccc3cc[nH]c13)C2]

The title compound was prepared from 2-amino-7-(2-bromo-phenyl)-4-methyl-7,8-dihydro-6H-quinazolin-5-one (example 3/i stage 2/3), following the procedure describing the synthesis of 2-amino-7-biphenyl-2-yl-4-methyl-7,8-dihydro-6H-quinazolin-5-one (example 5/a stage 1) using 7-boronic acid-1H-indole instead of phenyl-boronic acid.

Mass spectrum (ES-MS (+ve)) 369 [MH]+, Retention time 4.07 min, 86% UV.

1H NMR (360 MHz, DMSO-d6) δ ppm 10.70 (1H, d), 7.68 (1H, br. s), 7.32-7.58 (5H, m), 7.25 (2H, d), 7.05 (1H, br. s), 6.91 (1H, d), 6.47 (1H, br. s), 2.97-3.22 (3H, m), 2.63-2.91 (2H, m), 2.44 (3H, br. s).

General procedure for the Synthesis of 2-amino-4-ethyl-7-phenyl-7,8-dihydro-6H-quinazolin-5-one oxime

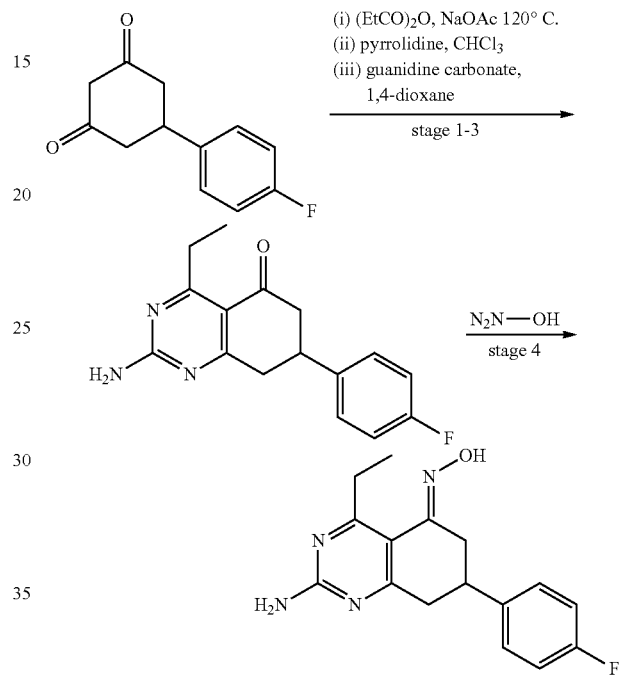

EXAMPLE 6

Synthesis of 2-Amino-4-ethyl-7-(4-fluoro-phenyl)-7,8-dihydro-6H-quinazolin-5-one oxime using Scheme 7

2-Amino-4-ethyl-7-(4-fluoro-phenyl)-7,8-dihydro-6H-quinazolin-5-one oxime (Compound 91)

Stage 1-3: 2-Amino-4-ethyl-7-(4-fluoro-phenyl)-7,8-dihydro-6H-quinazolin-5-one

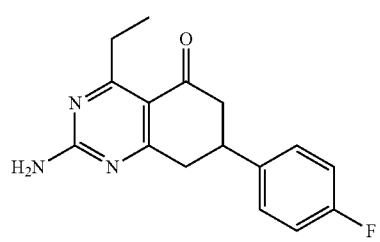 [SMILES: CCc1nc(N)nc2c1C(=O)CC(c1ccc(F)cc1)C2]

The title compound was prepared from 5-(4-fluoro-phenyl)-cyclohexane-1,3-dione, following the procedure describing the synthesis of 2-amino-7-(4-fluoro-phenyl)-4- methyl-7,8-dihydro-6H-quinazolin-5-one (example 3/a stage 1, 2 and 3). Propionic anhydride was used instead of acetic anhydride in stage 1.

Mass spectrum (ES-MS (+ve)) 286 [MH]$^+$, Retention time 2.83 min, 83% UV

1H NMR (250 MHz, DMSO-d$_6$) δ ppm 7.42 (2H, br. s), 7.38 (2H, dd), 7.14 (2H, t), 3.41 (1H, br. s), 3.03-3.18 (1H, m), 2.96 (2H, q), 2.78-2.91 (2H, m), 2.53-2.66 (1H, m), 1.11 (3H, t).

Stage 4: 2-Amino-4-ethyl-7-(4-fluoro-phenyl)-7,8-dihydro-6H-quinazolin-5-one oxime (Compound 91)

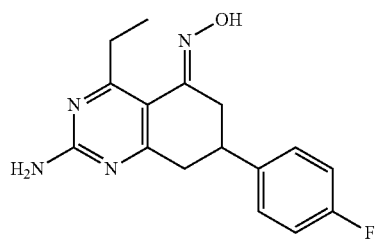 [SMILES: CCc1nc(N)nc2c1/C(=N/O)CC(c1ccc(F)cc1)C2]

The title compound was prepared from 2-amino-4-ethyl-7-(4-fluoro-phenyl)-7,8-dihydro-6H-quinazolin-5-one from stage 3, following the procedure describing the synthesis of 2-amino-7-(4-fluoro-phenyl)-4-methyl-7,8-dihydro-6H-quinazolin-5-one oxime (example 3/a stage 4).

Mass spectrum (ES-MS (+ve)) 301 [MH]$^+$, Retention time 3.33 min, 91% UV

1H NMR (360 MHz, DMSO-d$_6$) δ ppm 11.23 (1H, br. s), 6.74-7.74 (4H, m), 2.90-3.33 (5H, m), 2.78 (2H, d), 1.19 (3H, t).

EXAMPLE 7

Assay for Determining Hsp90 Inhibitory Activity

The representative assay for determining Hsp90 inhibitory activity has been described in detail (Development and implementation of a highly miniaturized confocal 2D-FIDA based high throughput screening assay to search for active site modulators of the human Heat Shock Protein 90β. *J. Biomol. Screen.* 2004, 9, 569-577; Development of a fluorescence polarization assay for the molecular chaperone Hsp90. *J. Biomol. Screen.* 2004, 9, 375-381). In the present case a Tamra-Geldanamycin ligand was used as a fluorescent tracer for the Hsp90 ATPase domain whereby small molecule inhibitors of the Hsp90 ATPase function displace the ligand out of its binding site. This displacement is measured by fluorescence changes. An alternative assay setup directly measures the inhibition of the catalytic ATPase function of Hsp90 by molecules such as those disclosed herein and others (High throughput screening assay for inhibitors of heat-shock protein 90 ATPase activity. *Anal. Biochem.* 2004, 327, 176-183). ATPase inhibition is a prerequisite for the therapeutic application of the inhibitors.

Using these assay formats the following typical inhibition data were recorded and are shown in Table 1.

TABLE 1

| Compound | Name | Structure | Geldanamycin binding assay |
|---|---|---|---|
| 1 | 2-Amino-7-(4-chloro-phenyl)-7,8-dihydro-6H-quinazolin-5-one oxime | 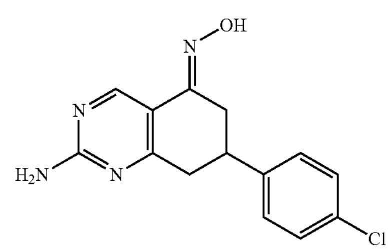 [SMILES: Nc1ncc2c(n1)CC(c1ccc(Cl)cc1)C/C2=N\O] | B |
| 2 | 2-Amino-7-(4-chloro-phenyl)-7,8-dihydro-6H-quinazolin-5-one O-methyl-oxime | 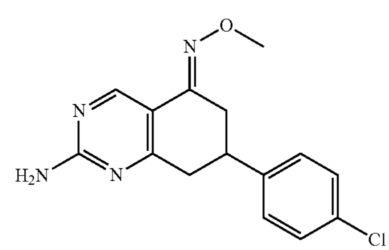 [SMILES: CO/N=C1\CC(c2ccc(Cl)cc2)Cc2nc(N)ncc21] | B |
| 3 | 2-Amino-7-phenyl-7,8-dihydro-6H-quinazolin-5-one oxime | 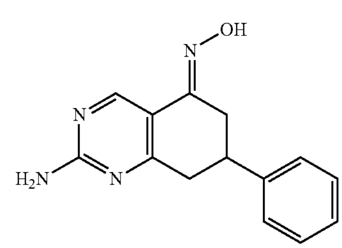 [SMILES: Nc1ncc2c(n1)CC(c1ccccc1)C/C2=N\O] | B |

TABLE 1-continued

| Compound | Name | Structure | Geldanamycin binding assay |
|---|---|---|---|
| 4 | 2-Amino-7-phenyl-7,8-dihydro-6H-quinazolin-5-one O-methyl-oxime | 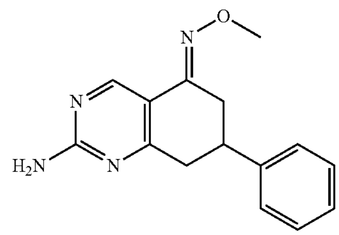 [SMILES: CO/N=C1\CC(c2ccccc2)Cc2nc(N)ncc21] | B |
| 5 | 2-Amino-7-phenyl-7,8-dihydro-6H-quinazolin-5-one oxime-O-acetyl | 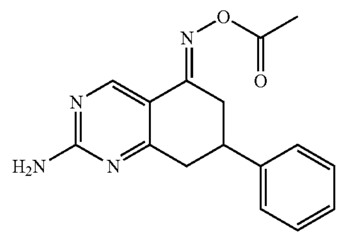 [SMILES: CC(=O)O/N=C1\CC(c2ccccc2)Cc2nc(N)ncc21] | C |
| 6 | 2-Amino-7-(4-fluoro-phenyl)-7,8-dihydro-6H-quinazolin-5-one oxime | 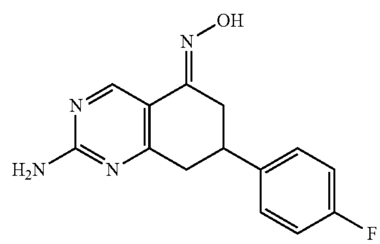 [SMILES: Nc1ncc2c(n1)CC(c1ccc(F)cc1)C/C2=N\O] | B |
| 7 | 2-Amino-7-(4-fluoro-phenyl)-7,8-dihydro-6H-quinazolin-5-one O-methyl-oxime | 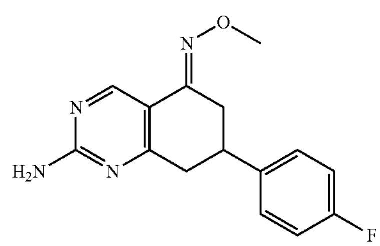 [SMILES: CO/N=C1\CC(c2ccc(F)cc2)Cc2nc(N)ncc21] | B |
| 8 | 2-Amino-7-(4-fluoro-phenyl)-7,8-dihydro-6H-quinazolin-5-one O-ethyl-oxime | 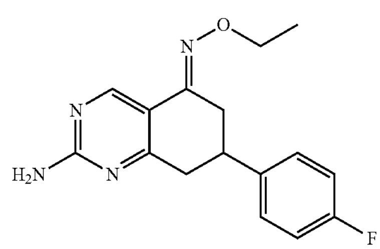 [SMILES: CCO/N=C1\CC(c2ccc(F)cc2)Cc2nc(N)ncc21] | B |
| 9 | [2-Amino-7-(4-fluoro-phenyl)-7,8-dihydro-6H-quinazolin-5-ylideneaminooxy]-acetic acid | 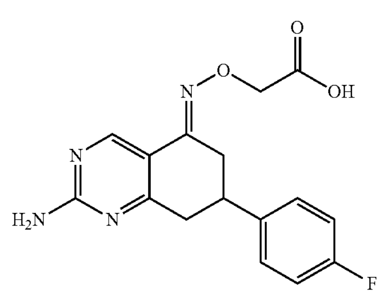 [SMILES: Nc1ncc2c(n1)CC(c1ccc(F)cc1)C/C2=N\OCC(=O)O] | B |

TABLE 1-continued

| Compound | Name | Structure | Geldanamycin binding assay |
|---|---|---|---|
| 10 | 2-Amino-7-(4-fluoro-phenyl)-7,8-dihydro-6H-quinazolin-5-one O-(2-morpholin-4-yl-2-oxo-ethyl)-oxime | 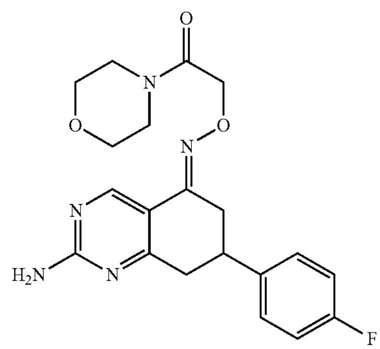 [SMILES: Nc1ncc2c(n1)CC(c1ccc(F)cc1)C/C2=N\OCC(=O)N1CCOCC1] | C |
| 11 | 2-Amino-7-(4-fluoro-phenyl)-7,8-dihydro-6H-quinazolin-5-one O-propyl-oxime | 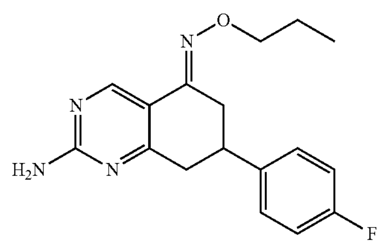 [SMILES: CCCO/N=C1\CC(c2ccc(F)cc2)Cc2nc(N)ncc21] | B |
| 12 | 2-Amino-7-(4-fluoro-phenyl)-7,8-dihydro-6H-quinazolin-5-one O-butyl-oxime | 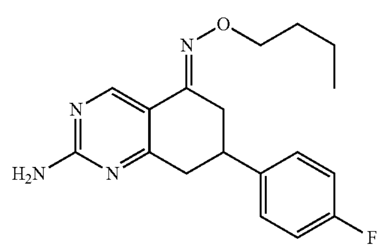 [SMILES: CCCCO/N=C1\CC(c2ccc(F)cc2)Cc2nc(N)ncc21] | C |
| 13 | 4-[2-Amino-7-(4-fluoro-phenyl)-7,8-dihydro-6H-quinazolin-5-ylideneaminooxy]-butyric acid ethyl ester | 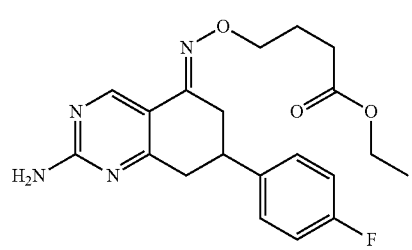 [SMILES: CCOC(=O)CCCO/N=C1\CC(c2ccc(F)cc2)Cc2nc(N)ncc21] | B |
| 14 | 4-[2-Amino-7-(4-fluoro-phenyl)-7,8-dihydro-6H-quinazolin-5-ylideneaminooxy]-butyric acid | 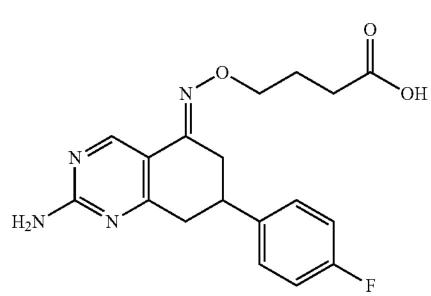 [SMILES: Nc1ncc2c(n1)CC(c1ccc(F)cc1)C/C2=N\OCCCC(=O)O] | B |

TABLE 1-continued

| Compound | Name | Structure | Geldanamycin binding assay |
|---|---|---|---|
| 15 | 2-Amino-7-(4-fluoro-phenyl)-7,8-dihydro-6H-quinazolin-5-one O-(2-morpholin-4-yl-ethyl)-oxime | 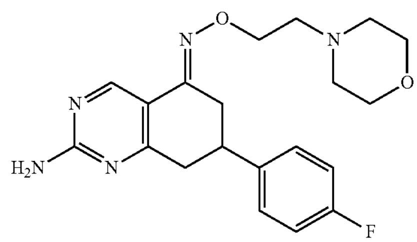 [SMILES: Nc1ncc2c(n1)CC(c1ccc(F)cc1)C/C2=N\OCCN1CCOCC1] | C |
| 16 | 2-Amino-7-(2-methoxy-phenyl)-7,8-dihydro-6H-quinazolin-5-one oxime | 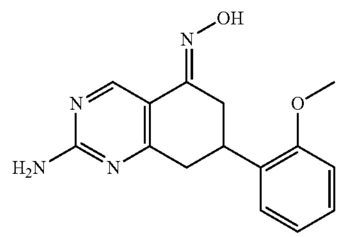 [SMILES: COc1ccccc1C1C/C(=N\O)c2cnc(N)nc2C1] | B |
| 17 | 2-Amino-7-(2-methoxy-phenyl)-7,8-dihydro-6H-quinazolin-5-one O-methyl-oxime | 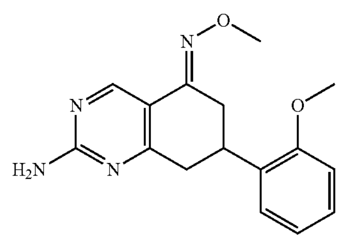 [SMILES: CO/N=C1\CC(c2ccccc2OC)Cc2nc(N)ncc21] | B |
| 18 | 2-Amino-7-thien-2-yl-7,8-dihydro-6H-quinazolin-5-one oxime | 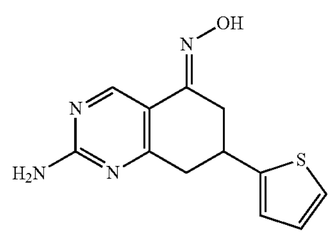 [SMILES: Nc1ncc2c(n1)CC(c1cccs1)C/C2=N\O] | B |
| 19 | 2-Amino-7-thien-2-yl-7,8-dihydro-6H-quinazolin-5-one O-methyl-oxime | 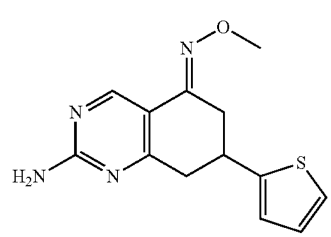 [SMILES: CO/N=C1\CC(c2cccs2)Cc2nc(N)ncc21] | C |
| 20 | 2-Amino-7-(2-fluoro-phenyl)-7,8-dihydro-6H-quinazolin-5-one oxime | 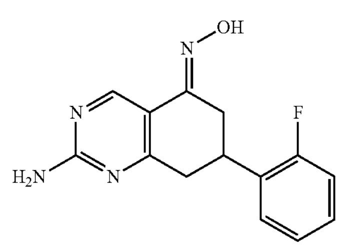 [SMILES: Nc1ncc2c(n1)CC(c1ccccc1F)C/C2=N\O] | C |

TABLE 1-continued

| Compound | Name | Structure | Geldanamycin binding assay |
|---|---|---|---|
| 21 | 2-Amino-7-(2-fluoro-phenyl)-7,8-dihydro-6H-quinazolin-5-one O-methyl-oxime | 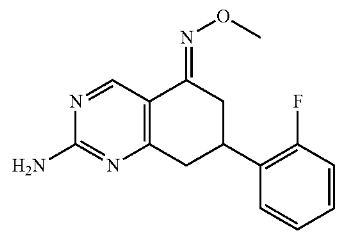 [SMILES: CO/N=C1\CC(c2ccccc2F)Cc2nc(N)ncc21] | C |
| 22 | 2-Amino-7-p-tolyl-7,8-dihydro-6H-quinazolin-5-one oxime | 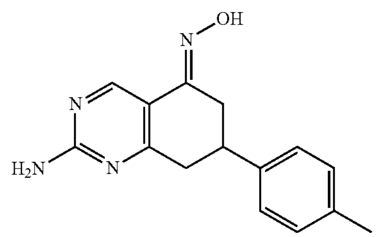 [SMILES: Cc1ccc(C2C/C(=N\O)c3cnc(N)nc3C2)cc1] | B |
| 23 | 2-Amino-7-p-tolyl-7,8-dihydro-6H-quinazolin-5-one O-methyl-oxime | 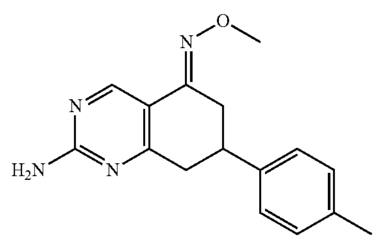 [SMILES: CO/N=C1\CC(c2ccc(C)cc2)Cc2nc(N)ncc21] | B |
| 24 | 2-Amino-7-(2-bromo-phenyl)-7,8-dihydro-6H-quinazolin-5-one oxime | 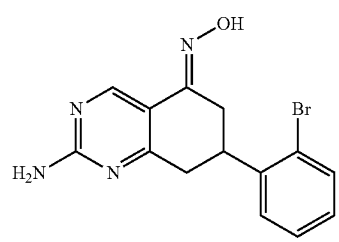 [SMILES: Nc1ncc2c(n1)CC(c1ccccc1Br)C/C2=N\O] | C |
| 25 | 2-Amino-7-(2-bromo-4-fluoro-phenyl)-7,8-dihydro-6H-quinazolin-5-one oxime | 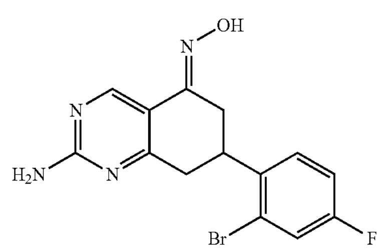 [SMILES: Nc1ncc2c(n1)CC(c1ccc(F)cc1Br)C/C2=N\O] | C |
| 26 | 2-Amino-7-(2,4-difluoro-phenyl)-7,8-dihydro-6H-quinazolin-5-one oxime | 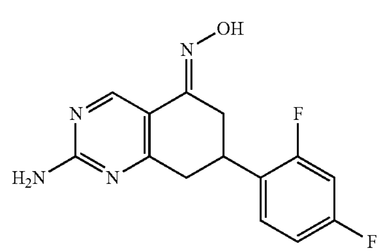 [SMILES: Nc1ncc2c(n1)CC(c1ccc(F)cc1F)C/C2=N\O] | C |

TABLE 1-continued

| Compound | Name | Structure | Geldanamycin binding assay |
|---|---|---|---|
| 27 | 2-Amino-7-(2,6-dimethoxy-phenyl)-7,8-dihydro-6H-quinazolin-5-one oxime | 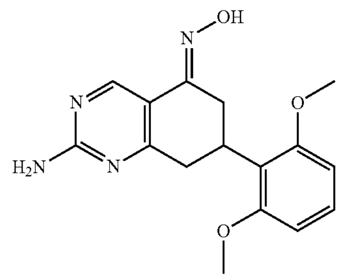 [SMILES: COc1cccc(OC)c1C1C/C(=N\O)c2cnc(N)nc2C1] | C |
| 28 | 2-Amino-7-benzo[1,3]dioxol-4-yl-7,8-dihydro-6H-quinazolin-5-one oxime | 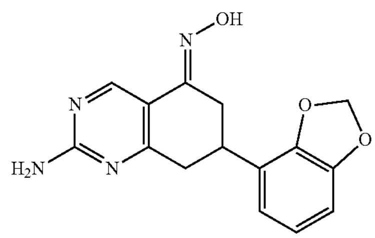 [SMILES: Nc1ncc2c(n1)CC(c1cccc3c1OCO3)C/C2=N\O] | B |
| 29 | 2-Amino-7-(2-morpholin-4-yl phenyl)-7,8-dihydro-6H-quinazolin-5-one oxime | 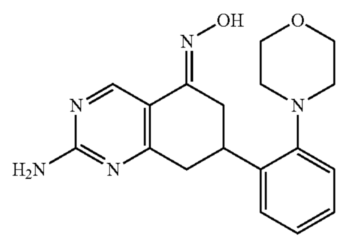 [SMILES: Nc1ncc2c(n1)CC(c1ccccc1N1CCOCC1)C/C2=N\O] | B |
| 30 | 2-Amino-7-(4-fluoro-phenyl)-4-methyl-7,8-dihydro-6H-quinazolin-5-one oxime | 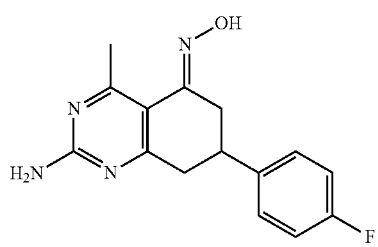 [SMILES: Cc1nc(N)nc2c1/C(=N/O)CC(c1ccc(F)cc1)C2] | A |
| 31 | 2-Amino-7-(4-fluoro-phenyl)-4-methyl-7,8-dihydro-6H-quinazolin-5-one O-methyl-oxime | 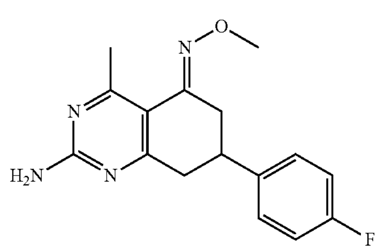 [SMILES: CO/N=C1\CC(c2ccc(F)cc2)Cc2nc(N)nc(C)c21] | B |
| 32 | 2-Amino-7-(4-fluoro-phenyl)-4-methyl-7,8-dihydro-6H-quinazolin-5-one O-(2-dimethylamino-ethyl)-oxime | 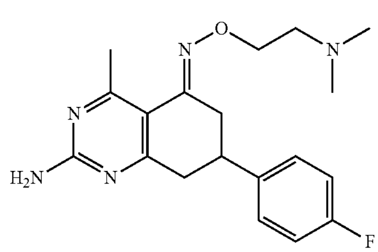 [SMILES: Cc1nc(N)nc2c1/C(=N/OCCN(C)C)CC(c1ccc(F)cc1)C2] | B |

TABLE 1-continued

| Compound | Name | Structure | Geldanamycin binding assay |
|---|---|---|---|
| 33 | 2-Amino-7-furan-2-yl-4-methyl-7,8-dihydro-6H-quinazolin-5-one oxime | 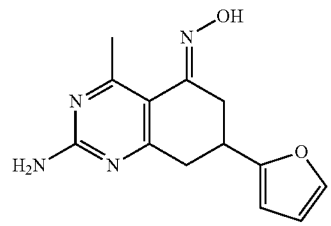 [SMILES: Cc1nc(N)nc2c1/C(=N/O)CC(c1ccco1)C2] | C |
| 34 | 2-Amino-7-furan-2-yl-4-methyl-7,8-dihydro-6H-quinazolin-5-one O-methyl-oxime | 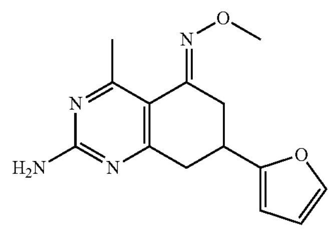 [SMILES: CO/N=C1\CC(c2ccco2)Cc2nc(N)nc(C)c21] | C |
| 35 | 2-Amino-7-furan-2-yl-4-methyl-7,8-dihydro-6H-quinazolin-5-one O-(2-dimethylamino-ethyl)-oxime | 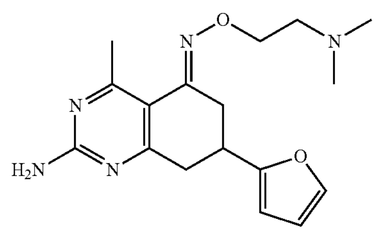 [SMILES: Cc1nc(N)nc2c1/C(=N/OCCN(C)C)CC(c1ccco1)C2] | C |
| 36 | 2-Amino-4-methyl-7-phenyl-7,8-dihydro-6H-quinazolin-5-one oxime | 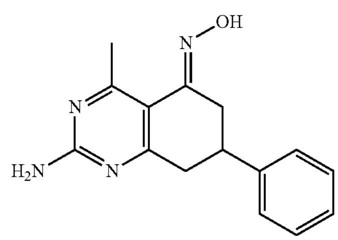 [SMILES: Cc1nc(N)nc2c1/C(=N/O)CC(c1ccccc1)C2] | C |
| 37 | 2-Amino-4-methyl-7-phenyl-7,8-dihydro-6H-quinazolin-5-one O-methyl-oxime | 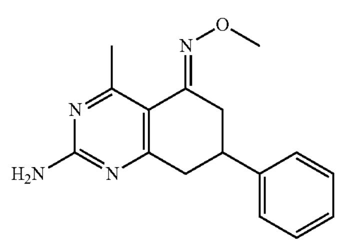 [SMILES: CO/N=C1\CC(c2ccccc2)Cc2nc(N)nc(C)c21] | B |
| 38 | 2-Amino-7-thien-2-yl-4-methyl-7,8-dihydro-6H-quinazolin-5-one oxime | 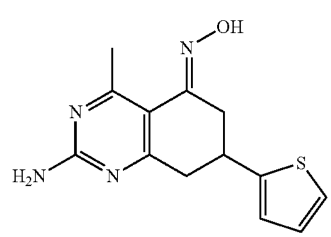 [SMILES: Cc1nc(N)nc2c1/C(=N/O)CC(c1cccs1)C2] | B |

TABLE 1-continued

| Compound | Name | Structure | Geldanamycin binding assay |
|---|---|---|---|
| 39 | 2-Amino-7-thien-2-yl-4-methyl-7,8-dihydro-6H-quinazolin-5-one O-methyl-oxime | 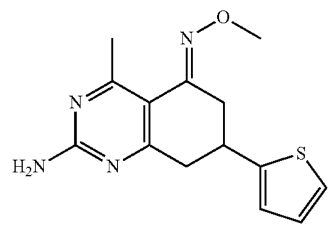 [SMILES: CO/N=C1\CC(c2cccs2)Cc2nc(N)nc(C)c21] | B |
| 40 | 2-Amino-4-methyl-7-p-tolyl-7,8-dihydro-6H-quinazolin-5-one oxime | 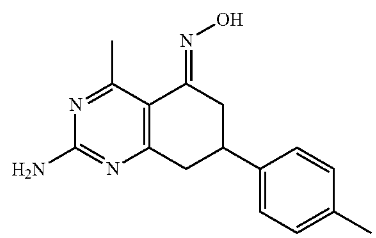 [SMILES: Cc1ccc(C2C/C(=N\O)c3c(C)nc(N)nc3C2)cc1] | C |
| 41 | 2-Amino-4-methyl-7-p-tolyl-7,8-dihydro-6H-quinazolin-5-one O-methyl-oxime | 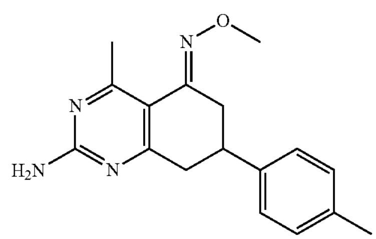 [SMILES: CO/N=C1\CC(c2ccc(C)cc2)Cc2nc(N)nc(C)c21] | B |
| 42 | 2-Amino-7-(2-methoxy-phenyl)-4-methyl-7,8-dihydro-6H-quinazolin-5-one oxime | 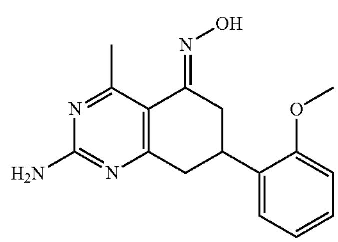 [SMILES: COc1ccccc1C1C/C(=N\O)c2c(C)nc(N)nc2C1] | C |
| 43 | 2-Amino-7-(2-methoxy-phenyl)-4-methyl-7,8-dihydro-6H-quinazolin-5-one O-methyl-oxime | 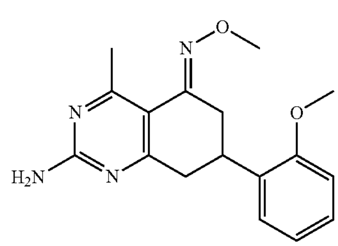 [SMILES: CO/N=C1\CC(c2ccccc2OC)Cc2nc(N)nc(C)c21] | B |
| 44 | 2-Amino-7-(3-fluoro-phenyl)-4-methyl-7,8-dihydro-6H-quinazolin-5-one oxime | 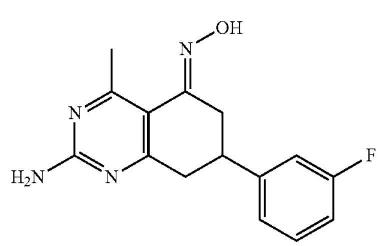 [SMILES: Cc1nc(N)nc2c1/C(=N/O)CC(c1cccc(F)c1)C2] | C |

TABLE 1-continued

| Compound | Name | Structure | Geldanamycin binding assay |
|---|---|---|---|
| 45 | 2-Amino-7-(3-fluoro-phenyl)-4-methyl-7,8-dihydro-6H-quinazolin-5-one O-methyl-oxime | 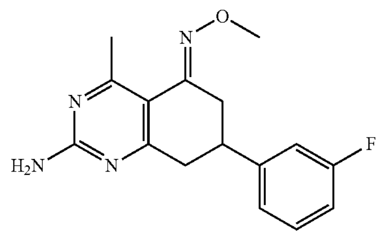 [SMILES: CO/N=C1\CC(c2cccc(F)c2)Cc2nc(N)nc(C)c21] | B |
| 46 | 2-Amino-7-(2-fluoro-phenyl)-4-methyl-7,8-dihydro-6H-quinazolin-5-one oxime | 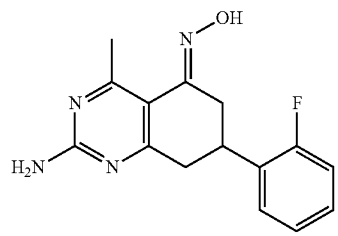 [SMILES: Cc1nc(N)nc2c1/C(=N/O)CC(c1ccccc1F)C2] | C |
| 47 | 2-Amino-7-(2-fluoro-phenyl)-4-methyl-7,8-dihydro-6H-quinazolin-5-one O-methyl-oxime | 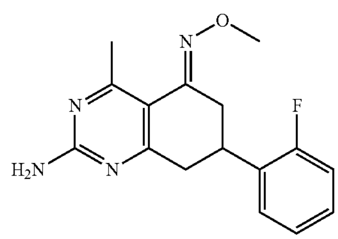 [SMILES: CO/N=C1\CC(c2ccccc2F)Cc2nc(N)nc(C)c21] | B |
| 48 | 2-Amino-7-(2-bromo-phenyl)-4-methyl-7,8-dihydro-6H-quinazolin-5-one oxime | 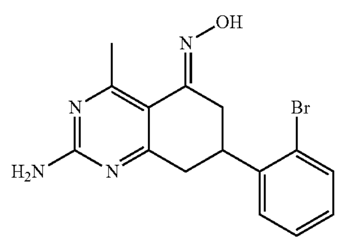 [SMILES: Cc1nc(N)nc2c1/C(=N/O)CC(c1ccccc1Br)C2] | C |
| 49 | 2-Amino-7-(2,6-dimethoxy-phenyl)-4-methyl-7,8-dihydro-6H-quinazolin-5-one oxime | 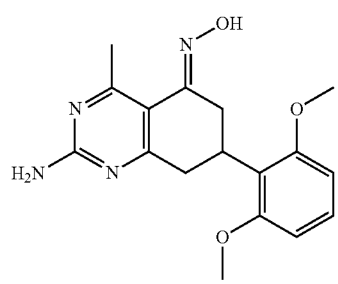 [SMILES: COc1cccc(OC)c1C1C/C(=N\O)c2c(C)nc(N)nc2C1] | B |
| 50 | 2-Amino-7-benzo[1,3]dioxol-4-yl-4-methyl-7,8-dihydro-6H-quinazolin-5-one oxime | 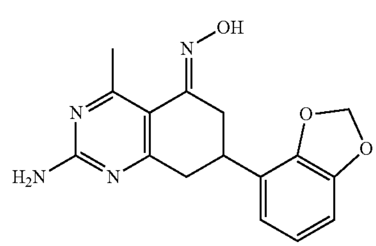 [SMILES: Cc1nc(N)nc2c1/C(=N/O)CC(c1cccc3c1OCO3)C2] | B |

TABLE 1-continued

| Compound | Name | Structure | Geldanamycin binding assay |
|---|---|---|---|
| 51 | 2-Amino-7-(4-fluoro-2-pyridin-3-yl-phenyl)-7,8-dihydro-6H-quinazolin-5-one oxime | 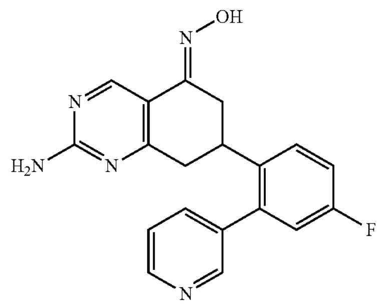 [SMILES: Nc1ncc2c(n1)CC(c1ccc(F)cc1-c1cccnc1)C/C2=N\O] | A |
| 52 | 2-Amino-7-biphenyl-2-yl-7,8-dihydro-6H-quinazolin-5-one oxime | 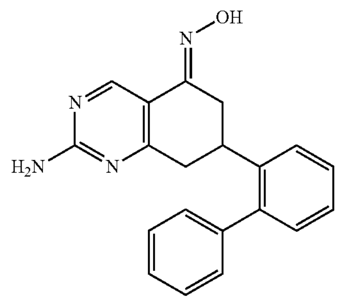 [SMILES: Nc1ncc2c(n1)CC(c1ccccc1-c1ccccc1)C/C2=N\O] | A |
| 53 | 2-Amino-7-biphenyl-2-yl-7,8-dihydro-6H-quinazolin-5-one O-methyl-oxime | 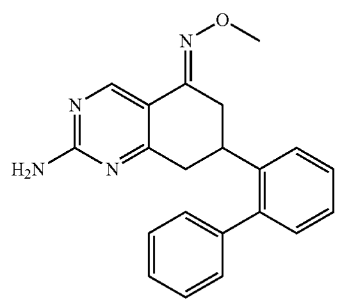 [SMILES: CO/N=C1\CC(c2ccccc2-c2ccccc2)Cc2nc(N)ncc21] | A |
| 54 | (2-Amino-7-biphenyl-2-yl-7,8-dihydro-6H-quinazolin-5-ylideneaminooxy)-acetic acid | 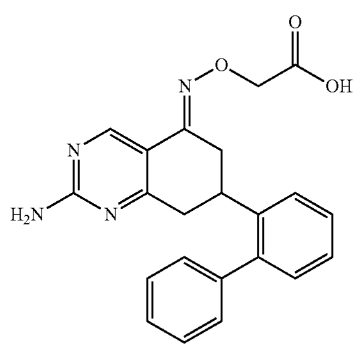 [SMILES: Nc1ncc2c(n1)CC(c1ccccc1-c1ccccc1)C/C2=N\OCC(=O)O] | A |
| 55 | 2-Amino-7-biphenyl-2-yl-7,8-dihydro-6H-quinazolin-5-one O-(2-morpholin-4-yl-2-oxo-ethyl)-oxime | 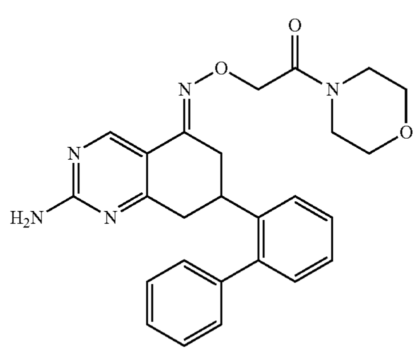 [SMILES: Nc1ncc2c(n1)CC(c1ccccc1-c1ccccc1)C/C2=N\OCC(=O)N1CCOCC1] | A |

TABLE 1-continued

| Compound | Name | Structure | Geldanamycin binding assay |
|---|---|---|---|
| 56 | 2-Amino-7-biphenyl-2-yl-7,8-dihydro-6H-quinazolin-5-one O-ethyl-oxime | 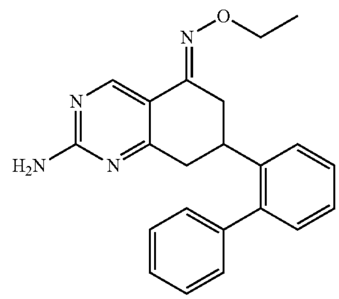 [SMILES: CCO/N=C1\CC(c2ccccc2-c2ccccc2)Cc2nc(N)ncc21] | B |
| 57 | 2-Amino-7-biphenyl-2-yl-7,8-dihydro-6H-quinazolin-5-one O-propyl-oxime | 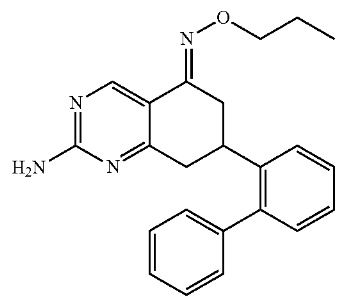 [SMILES: CCCO/N=C1\CC(c2ccccc2-c2ccccc2)Cc2nc(N)ncc21] | B |
| 58 | 2-Amino-7-biphenyl-2-yl-7,8-dihydro-6H-quinazolin-5-one O-butyl-oxime | 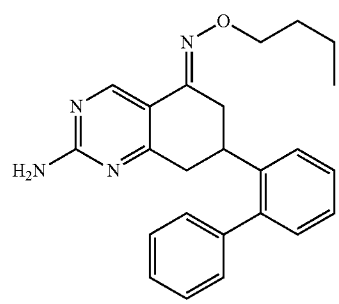 [SMILES: CCCCO/N=C1\CC(c2ccccc2-c2ccccc2)Cc2nc(N)ncc21] | B |
| 59 | 4-(2-Amino-7-biphenyl-2-yl-7,8-dihydro-6H-quinazolin-5-ylideneaminooxy)-butyric acid ethyl ester | 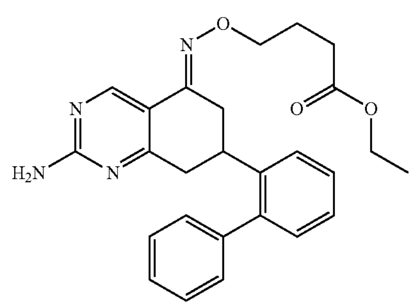 [SMILES: CCOC(=O)CCCO/N=C1\CC(c2ccccc2-c2ccccc2)Cc2nc(N)ncc21] | B |
| 60 | 4-(2-Amino-7-biphenyl-2-yl-7,8-dihydro-6H-quinazolin-5-ylideneaminooxy)-butyric acid | 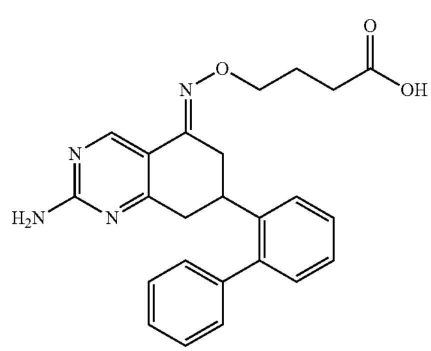 [SMILES: Nc1ncc2c(n1)CC(c1ccccc1-c1ccccc1)C/C2=N\OCCCC(=O)O] | B |

TABLE 1-continued

| Compound | Name | Structure | Geldanamycin binding assay |
|---|---|---|---|
| 61 | 2-Amino-7-biphenyl-2-yl-7,8-dihydro-6H-quinazolin-5-one O-(2-morpholin-4-yl-ethyl)-oxime | 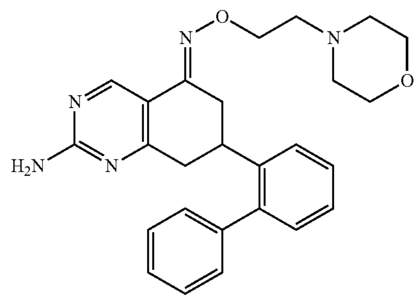 [SMILES: Nc1ncc2c(n1)CC(c1ccccc1-c1ccccc1)C/C2=N\OCCN1CCOCC1] | B |
| 62 | 2-Amino-7-(2-pyridin-2-yl-phenyl)-7,8-dihydro-6H-quinazolin-5-one oxime | 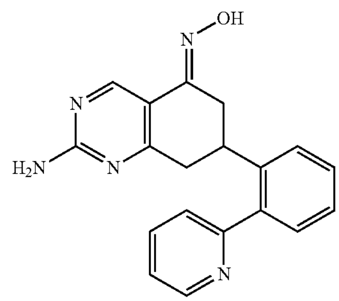 [SMILES: Nc1ncc2c(n1)CC(c1ccccc1-c1ccccn1)C/C2=N\O] | A |
| 63 | 2-Amino-7-(2-pyridin-3-yl-phenyl)-7,8-dihydro-6H-quinazolin-5-one oxime | 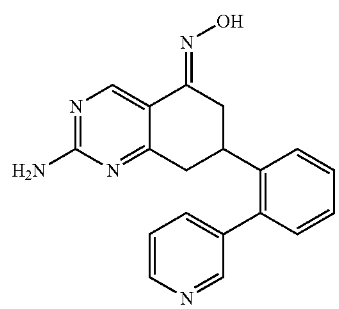 [SMILES: Nc1ncc2c(n1)CC(c1ccccc1-c1cccnc1)C/C2=N\O] | A |
| 64 | 2-Amino-7-(2-pyridin-4-yl-phenyl)-7,8-dihydro-6H-quinazolin-5-one oxime | 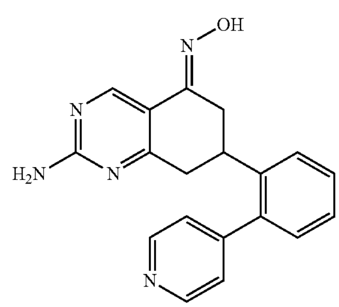 [SMILES: Nc1ncc2c(n1)CC(c1ccccc1-c1ccncc1)C/C2=N\O] | B |
| 65 | 2-Amino-7-[4-fluoro-2-(1-methyl-1H-pyrazol-4-yl)-phenyl]-7,8-dihydro-6H-quinazolin-5-one oxime | 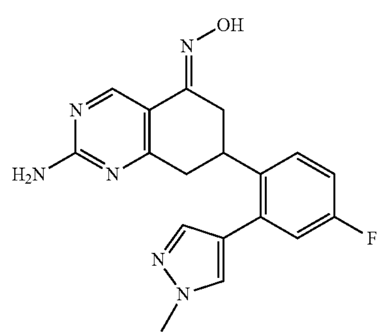 [SMILES: Cn1cc(-c2cc(F)ccc2C2C/C(=N\O)c3cnc(N)nc3C2)cn1] | A |

TABLE 1-continued

| Compound | Name | Structure | Geldanamycin binding assay |
|---|---|---|---|
| 66 | 2-Amino-7-biphenyl-2-yl-4-methyl-7,8-dihydro-6H-quinazolin-5-one oxime | 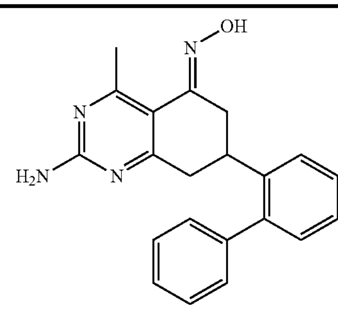 | A |
| 67 | 2-Amino-7-biphenyl-2-yl-4-methyl-7,8-dihydro-6H-quinazolin-5-one O-methyl-oxime | 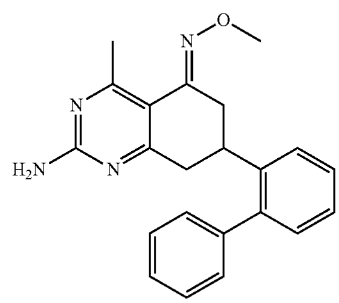 [SMILES: CO/N=C1\CC(c2ccccc2-c2ccccc2)Cc2nc(N)nc(C)c21] | B |
| 68 | 2-Amino-7-biphenyl-2-yl-4-methyl-7,8-dihydro-6H-quinazolin-5-one O-ethyl-oxime | 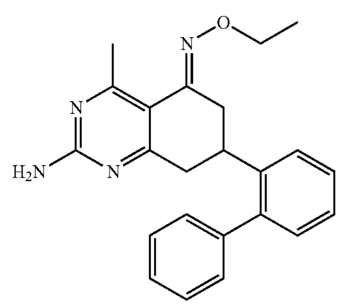 [SMILES: CCO/N=C1\CC(c2ccccc2-c2ccccc2)Cc2nc(N)nc(C)c21] | C |
| 69 | (2-Amino-7-biphenyl-2-yl-4-methyl-7,8-dihydro-6H-quinazolin-5-ylideneaminooxy)-acetic acid | 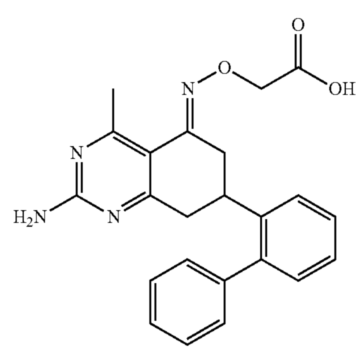 [SMILES: Cc1nc(N)nc2c1/C(=N/OCC(=O)O)CC(c1ccccc1-c1ccccc1)C2] | A |
| 70 | 2-Amino-7-biphenyl-2-yl-4-methyl-7,8-dihydro-6H-quinazolin-5-one O-(2-morpholin-4-yl-2-oxo-ethyl)-oxime | 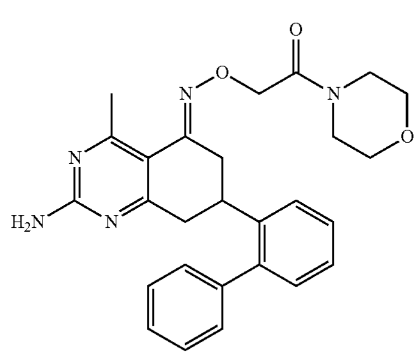 [SMILES: Cc1nc(N)nc2c1/C(=N/OCC(=O)N1CCOCC1)CC(c1ccccc1-c1ccccc1)C2] | A |

TABLE 1-continued

| Compound | Name | Structure | Geldanamycin binding assay |
|---|---|---|---|
| 71 | 2-Amino-7-biphenyl-2-yl-4-methyl-7,8-dihydro-6H-quinazolin-5-one O-propyl-oxime | 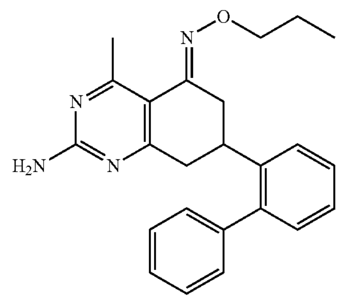 [SMILES: CCCO/N=C1\CC(c2ccccc2-c2ccccc2)Cc2nc(N)nc(C)c21] | B |
| 72 | 2-Amino-7-biphenyl-2-yl-4-methyl-7,8-dihydro-6H-quinazolin-5-one O-butyl-oxime | 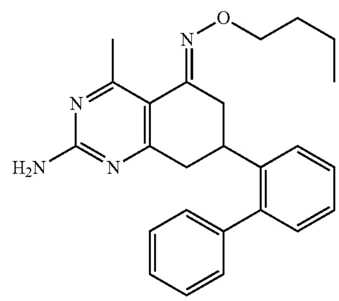 [SMILES: CCCCO/N=C1\CC(c2ccccc2-c2ccccc2)Cc2nc(N)nc(C)c21] | C |
| 73 | 4-(2-Amino-7-biphenyl-2-yl-4-methyl-7,8-dihydro-6H-quinazolin-5-ylideneaminooxy)-butyric acid ethyl ester | 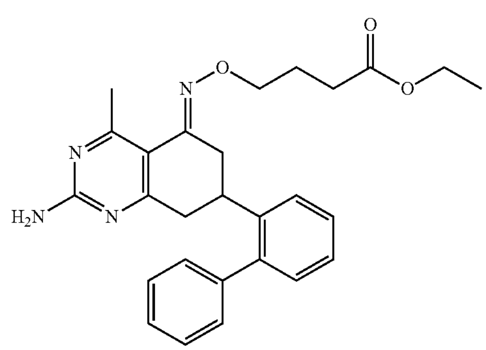 [SMILES: CCOC(=O)CCCO/N=C1\CC(c2ccccc2-c2ccccc2)Cc2nc(N)nc(C)c21] | C |
| 74 | 2-Amino-7-biphenyl-2-yl-4-methyl-7,8-dihydro-6H-quinazolin-5-one O-(3-morpholin-4-yl-propyl)-oxime | 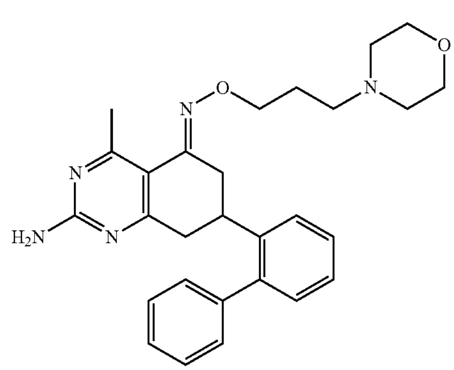 [SMILES: Cc1nc(N)nc2c1/C(=N/OCCCN1CCOCC1)CC(c1ccccc1-c1ccccc1)C2] | A |

TABLE 1-continued

| Compound | Name | Structure | Geldanamycin binding assay |
|---|---|---|---|
| 75 | 2-Amino-7-biphenyl-2-yl-4-methyl-7,8-dihydro-6H-quinazolin-5-one O-[3-(4-methyl-piperazin-1-yl)-propyl]-oxime | 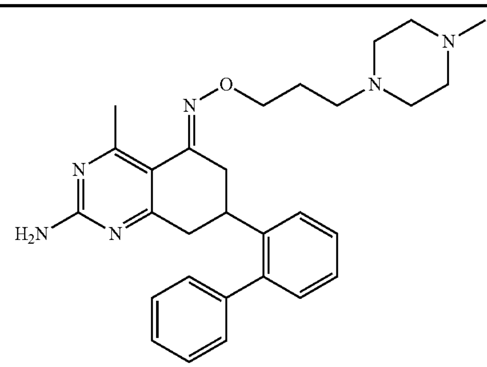 | A |
| 76 | 2-Amino-7-biphenyl-2-yl-4-methyl-7,8-dihydro-6H-quinazolin-5-one O-[2-(4-methyl-piperazin-1-yl)-ethyl]-oxime | 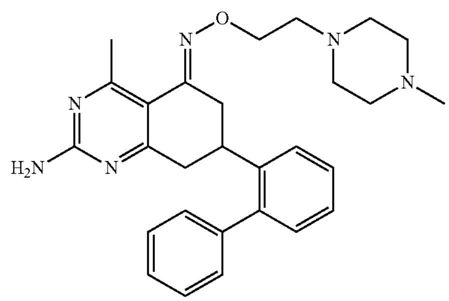 [SMILES: Cc1nc(N)nc2c1/C(=N/OCCN1CCN(C)CC1)CC(c1ccccc1-c1ccccc1)C2] | A |
| 77 | 2-Amino-7-biphenyl-2-yl-4-methyl-7,8-dihydro-6H-quinazolin-5-one O-(3-dimethylamino-propyl)-oxime | 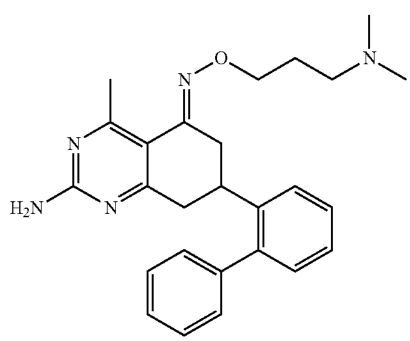 | A |
| 78 | 2-Amino-7-biphenyl-2-yl-4-methyl-7,8-dihydro-6H-quinazolin-5-one O-(2-pyrrolidin-1-yl-ethyl)-oxime | 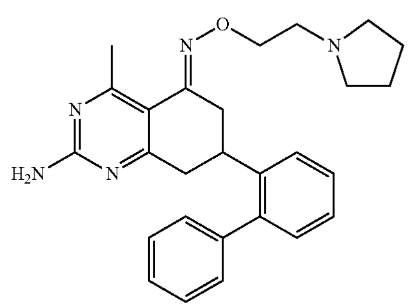 [SMILES: Cc1nc(N)nc2c1/C(=N/OCCN1CCCC1)CC(c1ccccc1-c1ccccc1)C2] | A |
| 79 | 2-Amino-7-biphenyl-2-yl-4-methyl-7,8-dihydro-6H-quinazolin-5-one O-(2-morpholin-4-yl-ethyl)-oxime | 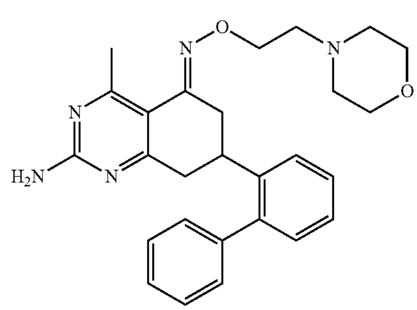 [SMILES: Cc1nc(N)nc2c1/C(=N/OCCN1CCOCC1)CC(c1ccccc1-c1ccccc1)C2] | A |

TABLE 1-continued

| Compound | Name | Structure | Geldanamycin binding assay |
|---|---|---|---|
| 80 | 2-Amino-7-biphenyl-2-yl-4-methyl-7,8-dihydro-6H-quinazolin-5-one O-(2-diethylamino-ethyl)-oxime | 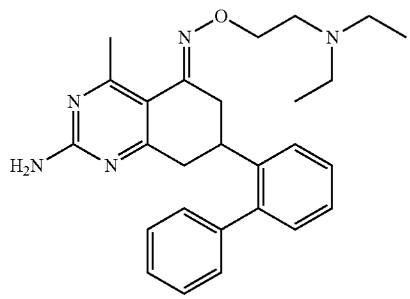 [SMILES: CCN(CC)CCO/N=C1\CC(c2ccccc2-c2ccccc2)Cc2nc(N)nc(C)c21] | A |
| 81 | 2-Amino-7-biphenyl-2-yl-4-methyl-7,8-dihydro-6H-quinazolin-5-one O-(2-dimethylamino-ethyl)-oxime | 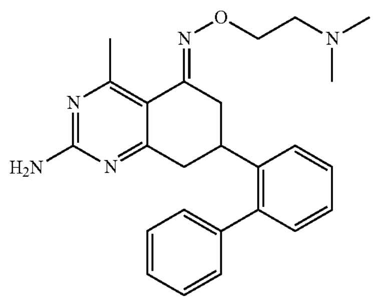 [SMILES: Cc1nc(N)nc2c1/C(=N/OCCN(C)C)CC(c1ccccc1-c1ccccc1)C2] | A |
| 82 | 2-Amino-7-biphenyl-2-yl-4-methyl-7,8-dihydro-6H-quinazolin-5-one O-(3-piperazin-1-yl-propyl)-oxime | 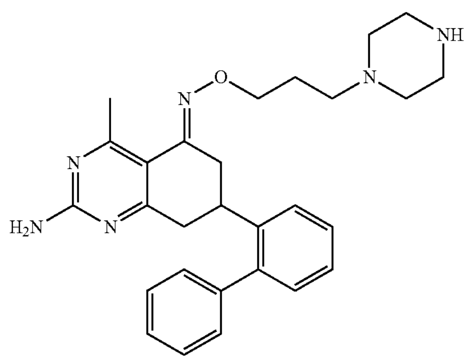 [SMILES: Cc1nc(N)nc2c1/C(=N/OCCCN1CCNCC1)CC(c1ccccc1-c1ccccc1)C2] | A |
| 83 | 2-Amino-7-biphenyl-2-yl-4-methyl-7,8-dihydro-6H-quinazolin-5-one O-hex-5-ynyl-oxime | 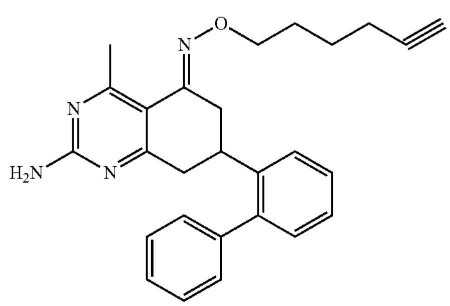 [SMILES: C#CCCCCO/N=C1\CC(c2ccccc2-c2ccccc2)Cc2nc(N)nc(C)c21] | B |
| 84 | 2-Amino-4-methyl-7-(2-pyridin-3-yl-phenyl)-7,8-dihydro-6H-quinazolin-5-one oxime | 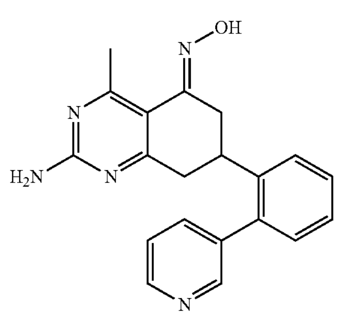 [SMILES: Cc1nc(N)nc2c1/C(=N/O)CC(c1ccccc1-c1cccnc1)C2] | A |

TABLE 1-continued

| Compound | Name | Structure | Geldanamycin binding assay |
|---|---|---|---|
| 85 | 2-Amino-4-methyl-7-(2-pyridin-4-yl-phenyl)-7,8-dihydro-6H-quinazolin-5-one oxime | 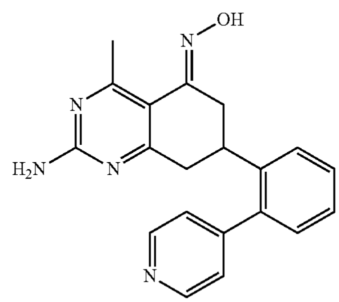 [SMILES: Cc1nc(N)nc2c1/C(=N/O)CC(c1ccccc1-c1ccncc1)C2] | B |
| 86 | 2-Amino-4-methyl-7-(2-pyridin-2-yl-phenyl)-7,8-dihydro-6H-quinazolin-5-one oxime | 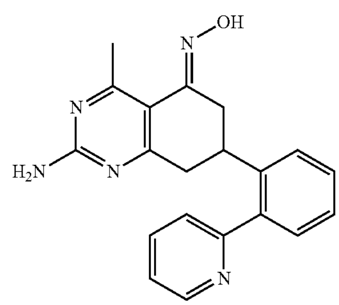 [SMILES: Cc1nc(N)nc2c1/C(=N/O)CC(c1ccccc1-c1ccccn1)C2] | A |
| 87 | 2-Amino-7-(5-fluoro-biphenyl-2-yl)-4-methyl-7,8-dihydro-6H-quinazolin-5-one oxime | 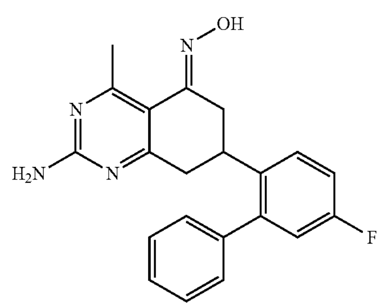 [SMILES: Cc1nc(N)nc2c1/C(=N/O)CC(c1ccc(F)cc1-c1ccccc1)C2] | |
| 88 | 2-Amino-7-(4-fluoro-biphenyl-2-yl)-4-methyl-7,8-dihydro-6H-quinazolin-5-one O-(3-dimethylamino-propyl)-oxime | 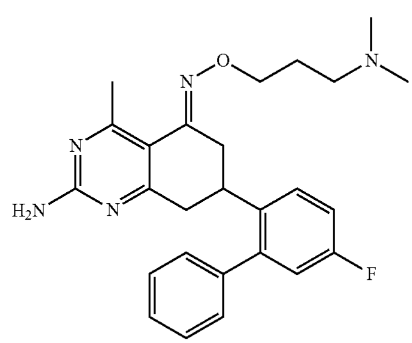 [SMILES: Cc1nc(N)nc2c1/C(=N/OCCCN(C)C)CC(c1ccc(F)cc1-c1ccccc1)C2] | |
| 89 | 2-Amino-7-(4-fluoro-2-pyridin-3-yl-phenyl)-4-methyl-7,8-dihydro-6H-quinazolin-5-one oxime | 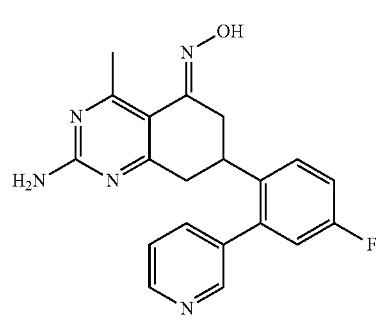 [SMILES: Cc1nc(N)nc2c1/C(=N/O)CC(c1ccc(F)cc1-c1cccnc1)C2] | |

TABLE 1-continued

| Compound | Name | Structure | Geldanamycin binding assay |
|---|---|---|---|
| 90 | 2-Amino-7-(4-fluoro-2-pyridin-3-yl-phenyl)-4-methyl-7,8-dihydro-6H-quinazolin-5-one O-(3-dimethylamino-propyl)-oxime | 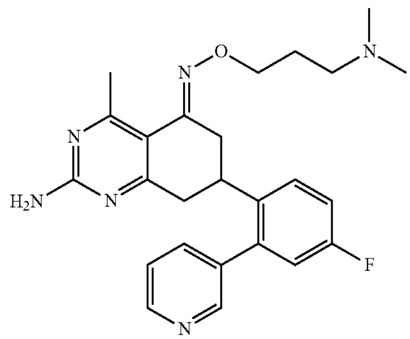 [SMILES: Cc1nc(N)nc2c1/C(=N/OCCCN(C)C)CC(c1ccc(F)cc1-c1cccnc1)C2] | |
| 91 | 2-Amino-4-ethyl-7-(4-fluoro-phenyl)-7,8-dihydro-6H-quinazolin-5-one oxime | 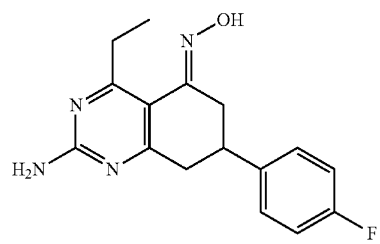 [SMILES: CCc1nc(N)nc2c1/C(=N/O)CC(c1ccc(F)cc1)C2] | B |

Categories of inhibition: A, $IC_{50}$ less than 1 µM; B, $IC_{50}$ between 1 and 10 µM; C, $IC_{50}$ higher than 10 µM; D, full inhibition of ATPase function at 5 µM.

The invention claimed is:
1. A compound of general formula (I):

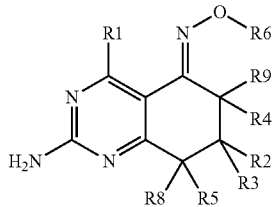

or a stereoisomer, tautomer, pharmaceutically acceptable salt, or prodrug thereof, wherein:
R1 is selected from hydrogen, halogen, hydroxyl, amino, thiol, $C_{1-6}$ alkoxy, $C_1$-$C_6$ alkylthiol, $C_1$-$C_{10}$ alkyl, $C_1$-$C_6$ alkylamino, arylamino, aryl($C_{1-6}$ alkyl)amino, aryl, heteroaryl, $C_3$-$C_7$ cycloalkyl, or $C_3$-$C_7$ heterocyclyl, any of which may optionally be substituted;
R2 and R3 are each independently hydrogen, halogen, $C_1$-$C_{10}$ alkyl, $C_2$-$C_{10}$ alkenyl, $C_2$-$C_{10}$ alkynyl, $C_3$-$C_7$ cycloalkyl, $C_5$-$C_7$ cycloalkenyl, aryl, heteroaryl, or $C_3$-$C_7$ heterocyclyl, any of which may optionally be substituted; R2 and R3 may also form a 3 to 6 membered Spiro ring system; and wherein one of R2 and R3 are hydrogen;
R4, R5, R8 and R9 are each independently selected from hydrogen, halogen, $C_1$-$C_6$ alkyl, —OR7, —SR7, —NR7R7', —OC(O)R7', —N(R7)C(O)R7', or —N(R7)SO$_2$R7'; R4 and R9 and/or R5 and R8 may also form a Spiro ring system;
R7 and R7' are each independently hydrogen, $C_{1-6}$ alkyl, $C_2$-$C_5$ alkenyl, $C_2$-$C_5$ alkynyl, $C_3$-$C_7$ cycloalkyl, $C_5$-$C_7$ cycloalkenyl, aryl, heteroaryl, or $C_3$-$C_7$ heterocyclyl, any of which may optionally be substituted;
or
when R4, R5, R8 or R9 is —OC(O)R7', —N(R7)C(O)R7', or —N(R7)SO$_2$R7', R7' may additionally be NR10R11, where R10 and R11 are each independently hydrogen or $C_1$-$C_6$ alkyl;
and
R6 is hydrogen, halogen, $C_{1-5}$ alkyl, $C_2$-$C_5$ alkenyl, $C_2$-$C_5$ alkynyl, $C_3$-$C_7$ cycloalkyl, $C_5$-$C_7$ cycloalkenyl, aryl, heteroaryl, or $C_3$-$C_7$ heterocyclyl, any of which may optionally be substituted.

2. The compound as claimed in claim 1, wherein, R8 is H; or R9 is H; or R8 and R9 is H.
3. The compound as claimed in claim 1, wherein R1 is hydrogen or $C_1$-$C_6$ alkyl, which may optionally be substituted with halo.
4. The compounds as claimed in claim 3, wherein R1 is hydrogen or $C_1$-$C_3$ alkyl.
5. The compound as claimed in claim 4, wherein R1 is hydrogen, methyl or ethyl.
6. The compound as claimed in claim 1, wherein R4 and R5 are hydrogen.
7. The compound as claimed in claim 1, wherein one of R2 and R3 is aryl, heteroaryl, $C_3$-$C_7$ cycloalkyl, $C_3$-$C_7$ heterocyclyl or $C_{1-6}$ alkyl; any of which may optionally be substituted with one or more substituents selected from the group consisting of halogen, OH, $C_1$-$C_6$ alkoxy, O—$C_3$-$C_7$ cycloalkyl, aryl, methyl substituted aryl, halo substituted aryl, heteroaryl, methyl substituted heteroaryl, halo substituted heteroaryl, $C_3$-$C_7$ heterocyclyl, O—$C_3$-$C_7$ heterocyclyl, O-aryl, O-heteroaryl moieties and $C_1$-$C_6$ alkyl moieties, wherein R2 or R3 is other than $C_1$-$C_6$ alkyl substituted alkyl.
8. The compound as claimed in claim 1, wherein R2 is hydrogen and R3 is furanyl, thienyl, phenyl or, any of which may be substituted by one or more halo, methyl, methoxy, hydroxyl or phenyl, pyridyl, pyrazole, indolyl, or morpholino groups, any of which may optionally be substituted.

9. The compound as claimed in claim 8, wherein R3 is 2-methoxyphenyl, 2-fluorophenyl, 4-methylphenyl, 3-fluorophenyl, 4-fluorophenyl, 4-chlorophenyl, phenyl, 2,6-dimethoxyphenyl, 2,6-difluorophenyl, or 1-(2-phenoxyethanol).

10. The compound as claimed in claim 1, wherein R6 is hydrogen; or R6 is $C_1$-$C_5$ alkyl, $C_2$-$C_5$ alkenyl, $C_2$-$C_5$ alkynyl, or aryl, any of which may optionally be substituted.

11. The compound as claimed in claim 10, wherein R6 is hydrogen, methyl, ethyl, n-propyl, iso-propyl, t-butyl, phenyl, or dimethylaminomethyl.

12. The compound of claim 1 which is:
2-Amino-7-(4-chloro-phenyl)-7,8-dihydro-6H-quinazolin-5-one oxime;
2-Amino-7-(4-chloro-phenyl)-7,8-dihydro-6H-quinazolin-5-one O-methyl-oxime;
2-Amino-7-phenyl-7,9-dihydro-6H-quinazolin-5-one oxime;
2-Amino-7-phenyl-7,8-dihydro-6H-quinazolin-5-one O-methyl-oxime;
2-Amino-7-(4-fluoro-phenyl)-7,8-dihydro-6H-quinazolin-5-one oxime;
2-Amino-7-(4-fluoro-phenyl)-7,8-dihydro-6H-quinazolin-5-one O-methyl-oxime;
2-Amino-7-(2-methoxy-phenyl)-7,8-dihydro-6H-quinazolin-5-one oxime;
2-Amino-7-(2-methoxy-phenyl)-7,8-dihydro-6H-quinazolin-5-one O-methyl-oxime;
2-Amino-7-thien-2-yl-7,8-dihydro-6H-quinazolin-5-one oxime;
2-Amino-7-thien-2-yl-7,8-dihydro-6H-quinazolin-5-one O-methyl-oxime;
2-Amino-7-(2-fluoro-phenyl)-7,8-dihydro-6H-quinazolin-5-one oxime;
2-Amino-7-(2-fluoro-phenyl)-7,8-dihydro-6H-quinazolin-5-one O-methyl-oxime;
2-Amino-7-p-tolyl-7,8-dihydro-6H-quinazolin-5-one oxime;
2-Amino-7-p-tolyl-7,8-dihydro-6H-quinazolin-5-one O-methyl-oxime;
2-Amino-7-(4-fluoro-phenyl)-4-methyl-7,8-dihydro-6H-quinazolin-5-one oxime;
2-Amino-7-(4-fluoro-phenyl)-4-methyl-7,8-dihydro-6H-quinazolin-5-one O-methyl-oxime;
2-Amino-7-(4-fluoro-phenyl)-4-methyl-7,8-dihydro-6H-quinazolin-5-one O-(2-dimethylamino-ethyl)-oxime;
2-Amino-7-furan-2-yl-4-methyl-7,8-dihydro-6H-quinazolin-5-one oxime;
2-Amino-7-furan-2-yl-4-methyl-7, -dihydro-6H-quinazolin-5-one O-methyl-oxime;
2-Amino-4-methyl-7-phenyl-7,8-dihydro-6H-quinazolin-5-one oxime;
2-Amino-4-methyl-7-phenyl-7,8-dihydro-6H-quinazolin-5-one O-methyl-oxime;
2-Amino-7-thien-2-yl-4-methyl-7,8-dihydro-6H-quinazolin-5-one oxime;
2-Amino-7-thien-2-yl-4-methyl-7,8-dihydro-6H-quinazolin-5-one O-methyl-oxime;
2-Amino-4-methyl-7-p-tolyl-7,8-dihydro-6H-quinazolin-5-one oxime;
2-Amino-4-methyl-7-p-tolyl-7,8-dihydro-6H-quinazolin-5-one O-methyl-oxime;
2-Amino-7-(2-methoxy-phenyl)-4-methyl-7,8-dihydro-6H-quinazolin-5-one oxime;
2-Amino-7-(2-methoxy-phenyl)-4-methyl-7,8-dihydro-6H-quinazolin-5-one O-methyl-oxime;
2-Amino-7-(3-fluoro-phenyl)-4-methyl-7,8-dihydro-6H-quinazolin-5-one oxime;
2-Amino-7-(3-fluoro-phenyl)-4-methyl-7,8-dihydro-6H-quinazolin-5-one O-methyl-oxime;
2-Amino-7-(2-fluoro-phenyl)-4-methyl-7,8-dihydro-6H-quinazolin-5-one oxime;
2-Amino-7-(2-fluoro-phenyl)-4-methyl-7,8-dihydro-6H-quinazolin-5-one O-methyl-oxime;
or a stereoisomer, tautomer, pharmaceutically acceptable salt or prodrug thereof.

13. A pharmaceutical composition comprising a compound as claimed in claim 1 together with a pharmaceutically acceptable excipient.

14. The compounds as claimed in claim 2, wherein R1 is hydrogen or $C_1$-$C_3$ alkyl.

15. The compounds as claimed in claim 14, wherein R1 is hydrogen or $C_1$-$C_3$ alkyl.

16. The compound as claimed in claim 15, wherein 54 and R5 are hydrogen.

17. The compound as claimed in claim 16, wherein one of R2 and R3 is aryl, heteroaryl, $C_3$-$C_7$ cycloalkyl, $C_3$-$C_7$ heterocyclyl or $C_1$-$C_6$ alkyl; any of which may optionally be substituted with one or more substituents selected from the group consisting of halogen, OH, $C_1$-$C_6$ alkoxy, O—$C_3$-$C_7$ cycloalkyl, aryl, methyl substituted aryl, halo substituted aryl, heteroaryl, methyl substituted heteroaryl, halo substituted heteroaryl, $C_3$-$C_7$ heterocyclyl, O—$C_3$-$C_7$ heterocyclyl, O-aryl, O-heteroaryl moieties and $C_1$-$C_6$ alkyl moieties, wherein R2 or R3 is other than $C_1$-$C_6$ alkyl substituted alkyl.

18. The compound of claim 1, wherein R2 is hydrogen and R3 is phenyl, which may optionally be substituted with one or more substituents selected from the group consisting of halogen, unsubstituted aryl and unsubstituted heteroaryl.

19. The compound of claim 18, wherein R3 is 4-fluoro-2-pyridylphenyl.

20. A compound, wherein the compound is:
2-Amino-7-phenyl-7,8-dihydro-6H-quinazolin-5-one oxime-O-acetyl;
2-Amino-7-(4-fluoro-phenyl)-7,8-dihydro-6H-quinazolin-5-one O-ethyl-oxime;
[2-Amino-7-(4-fluoro-phenyl)-7,8-dihydro-6H-quinazolin-5-ylideneaminooxy]-acetic acid;
2-Amino-7-(4-fluoro-phenyl)-7,8-dihydro-6H-quinazolin-5-one O-(2-morpholin-4-yl-2-oxo-ethyl)-oxime;
2-Amino-7-(4-fluoro-phenyl)-7,8-dihydro-6H-quinazolin-5-one O-propyl-oxime;
2-Amino-7-(4-fluoro-phenyl)-7,8-dihydro-60-quinazolin-5-one O-butyl-oxime;
4-[2-Amino-7-(4-fluoro-phenyl)-7,8-dihydro-6H-quinazolin-5-ylideneaminooxy]-butyric acid ethyl ester;
4-[2-Amino-7-(4-fluoro-phenyl)-7,8-dihydro-6H-quinazolin-5-ylideneaminooxy]-butyric acid;
2-Amino-7-(4-fluoro-phenyl)-7,8-dihydro-6H-quinazolin-5-one O-(2-morpholin-4-yl-ethyl)-oxime;
2-Amino-7-(2-bromo-phenyl)-7,8-dihydro-6H-quinazolin-5-one oxime;
2-Amino-7-(2-bromo-4-fluoro-phenyl)-7,8-dihydro-6H-quinazolin-5-one oxime;
2-Amino-7-(2,4-difluoro-phenyl)-7,8-dihydro-6H-quinazolin-5-one oxime;
2-Amino-7-(2,6-dimethoxy-phenyl)-7,8-dihydro-6H-quinazolin-5-one oxime;
2-Amino-7-benzo[1,3]dioxol-4-yl-, -dihydro-6H-quinazolin-5-one oxime;

2-Amino-7-(2-morpholin-4-yl-phenyl)-7,8-dihydro-6H-quinazolin-5-one oxime;
2-Amino-7-furan-2-yl-4-methyl-7,8-dihydro-6H-quinazolin-5-one O-(2-dimethylamino-ethyl)-oxime;
2-Amino-7-(2-bromo-phenyl)-4-methyl-7,8-dihydro-6H-quinazolin-5-one oxime;
2-Amino-7-(2,6-dimethoxy-phenyl)-4-methyl-7,8-dihydro-6H-quinazolin-5-one oxime;
2-Amino-7-benzo[1,3]dioxol-4-yl-4-methyl-7,8-dihydro-6H-quinazolin-5-one oxime;
2-Amino-7-(4-fluoro-2-pyridin-3-yl-phenyl)-7,8-dihydro-6H-quinazolin-5-one oxime;
2-Amino-7-biphenyl-2-yl-7,8-dihydro-6H-quinazolin-5-one oxime;
2-Amino-7-biphenyl-2-yl-7,8-dihydro-6H-quinazolin-5-one O-methyl-oxime;
(2-Amino-7-biphenyl-2-yl-7,8-dihydro-6H-quinazolin-5-ylideneaminooxy)-acetic acid;
2-Amino-7-biphenyl-2-yl-7,8-dihydro-6H-quinazolin-5-one O-(2-morpholin-4-yl-2-oxo-ethyl)-oxime;
2-Amino-7-biphenyl-2-yl-7,8-dihydro-6H-quinazolin-5-one O-ethyl-oxime;
2-Amino-7-biphenyl-2-yl-7,8-dihydro-6H-quinazolin-5-one O-propyl-oxime;
2-Amino-7-biphenyl-2-yl-7,8-dihydro-6H-quinazolin-5-one O-butyl-oxime;
4-(2-Amino-7-biphenyl-2-yl-7,8-dihydro-6H-quinazolin-5-ylideneaminooxy)-butyric acid ethyl ester;
4-(2-Amino-7-biphenyl-2-yl-7,8-dihydro-6H-quinazolin-5-ylideneaminooxy)-butyric acid;
2-Amino-7-biphenyl-2-yl-7,8-dihydro-6H-quinazolin-5-one O-(2-morpholin-4-yl-ethyl)-oxime;
2-Amino-7-(2-pyridin-2-yl-phenyl)-7,8-dihydro-6H-quinazolin-5-one oxime;
2-Amino-7-(2-pyridin-3-yl-phenyl)-7,8-dihydro-6H-quinazolin-5-one oxime;
2-Amino-7-(2-pyridin-4-yl-phenyl)-7,8-dihydro-6H-quinazolin-5-one oxime;
2-Amino-7-[4-fluoro-2-(1-methyl-1H-pyrazol-4-yl)-phenyl]-7,8-dihydro-6H-quinazolin-5-one oxime;
2-Amino-7-biphenyl-2-yl-4-methyl-7,9-dihydro-6H-quinazolin-5-one oxime;
2-Amino-7-biphenyl-2-yl-4-methyl-7,8-dihydro-6H-quinazolin-5-one O-methyl-oxime;
2-Amino-7-biphenyl-2-yl-4-methyl-7,8-dihydro-6H-quinazolin-5-one O-ethyl-oxime;
(2-Amino-7-biphenyl-2-yl-4-methyl-7,8-dihydro-6H-quinazolin-5-ylideneaminooxy)-acetic acid;
2-Amino-7-biphenyl-2-yl-4-methyl-7,8-dihydro-6H-quinazolin-5-one O-(2-morpholin-4-yl-2-oxo-ethyl)-oxime;
2-Amino-7-biphenyl-2-yl-4-methyl-7,8-dihydro-6H-quinazolin-5-one O-propyl-oxime;
2-Amino-7-biphenyl-2-yl-4-methyl-7,8-dihydro-6H-quinazolin-5-one O-butyl-oxime;
4-(2-Amino-7-biphenyl-2-yl-4-methyl-7,8-dihydro-6H-quinazolin-5-ylideneaminooxy)-butyric acid ethyl ester;
2-Amino-7-biphenyl-2-yl-4-methyl-7,8-dihydro-6H-quinazolin-5-one O-(3-morpholin-4-yl-propyl)-oxime;
2-Amino-7-biphenyl-2-yl-4-methyl-7,8-dihydro-6H-quinazolin-5-one O-[3-(4-methyl-piperazin-1-yl)-propyl]-oxime;
2-Amino-7-biphenyl-2-yl-4-methyl-7,8-dihydro-6H-quinazolin-5-one O-[2-(4-methyl-piperazin-1-yl)-ethyl]-oxime;
2-Amino-7-biphenyl-2-yl-4-methyl-7,8-dihydro-6H-quinazolin-5-one O-(3-dimethylamino-propyl)-oxime;
2-Amino-7-biphenyl-2-yl-4-methyl-7,8-dihydro-6H-quinazolin-5-one O-(2-pyrrolidin-1-yl-ethyl)-oxime;
2-Amino-7-biphenyl-2-yl-4-methyl-7,8-dihydro-6H-quinazolin-5-one O-(2-morpholin-4-yl-ethyl)-oxime;
2-Amino-7-biphenyl-2-yl-4-methyl-7,8-dihydro-6H-quinazolin-5-one O-(2-diethylamino-ethyl)-oxime
2-Amino-7-biphenyl-2-yl-4-methyl-7,8-dihydro-6H-quinazolin-5-one O-(2-dimethylamino-ethyl)-oxime;
2-Amino-7-biphenyl-2-yl-4-methyl-7,8-dihydro-6H-quinazolin-5-one O-(3-piperazin-1-yl-propyl)-oxime;
2-Amino-7-biphenyl-2-yl-4-methyl-7,8-dihydro-6H-quinazolin-5-one O-hex-5-ynyl-oxime;
2-Amino-4-methyl-7-(2-pyridin-3-yl-phenyl)-7,8-dihydro-6H-quinazolin-5-one oxime;
2-Amino-4-methyl-7-(2-pyridin-4-yl-phenyl)-7,8-dihydro-6H-quinazolin-5-one oxime;
2-Amino-4-methyl-7-(2-pyridin-2-yl-phenyl)-7,8-dihydro-6H-quinazolin-5-one oxime;
2-Amino-7-(5-fluoro-biphenyl-2-yl)-4-methyl-7,8-dihydro-6H-quinazolin-5-one oxime;
2-Amino-7-(4-fluoro-biphenyl-2-yl)-4-methyl-7,8-dihydro-6H-quinazolin-5-one O-(3-dimethylamino-propyl)-oxime;
2-Amino-7-(4-fluoro-2-pyridin-3-yl-phenyl)-4-methyl-7,8-dihydro-6H-quinazolin-5-one oxime;
2-Amino-7-(4-fluoro-2-pyridin-3-yl-phenyl)-4-methyl-7,8-dihydro-6H-quinazolin-5-one O-(3-dimethylamino-propyl)-oxime;
2-Amino-4-ethyl-7-(4-fluoro-phenyl)-7,8-dihydro-6H-quinazolin-5-one oxime;
or a stereoisomer, tautomer, pharmaceutically acceptable salt or prodrug thereof.

21. The compound of claim 19, wherein the compound is:
2-Amino-7-(4-fluoro-2-pyridin-3-yl-phenyl)-4-methyl-7,8-dihydro-6H-quinazolin-5-one oxime.

* * * * *

UNITED STATES PATENT AND TRADEMARK OFFICE
CERTIFICATE OF CORRECTION

PATENT NO.        : 8,592,430 B2                                        Page 1 of 1
APPLICATION NO.   : 12/599116
DATED             : November 26, 2013
INVENTOR(S)       : Courtney et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 830 days.

Signed and Sealed this
Twenty-second Day of September, 2015

Michelle K. Lee
*Director of the United States Patent and Trademark Office*